(12) United States Patent
Gupte

(10) Patent No.: US 10,621,543 B2
(45) Date of Patent: Apr. 14, 2020

(54) SYSTEM AND METHOD TO ENABLE DELIVERY AND PICK UP OF PACKAGES USING PODS AND UNMANNED VEHICLES

(71) Applicant: Aniruddha Rajendra Gupte, Pune (IN)

(72) Inventor: Aniruddha Rajendra Gupte, Pune (IN)

( * ) Notice: Subject to any disclaimer, the term of this patent is extended or adjusted under 35 U.S.C. 154(b) by 56 days.

(21) Appl. No.: 15/659,641

(22) Filed: Jul. 26, 2017

(65) Prior Publication Data

US 2018/0130017 A1    May 10, 2018

Related U.S. Application Data

(60) Provisional application No. 62/536,992, filed on Jul. 26, 2017.

(30) Foreign Application Priority Data

Jul. 27, 2016 (IN) .............................. 201621025733

(51) Int. Cl.
*G06F 7/00*         (2006.01)
*G06Q 10/08*        (2012.01)
(Continued)

(52) U.S. Cl.
CPC ....... *G06Q 10/0836* (2013.01); *B64C 39/024* (2013.01); *B65G 1/1371* (2013.01);
(Continued)

(58) Field of Classification Search
None
See application file for complete search history.

(56) References Cited

U.S. PATENT DOCUMENTS 9,216,857 B1 * 12/2015 Kalyan ................ G06Q 10/087
2014/0254896 A1 * 9/2014 Zhou ...................... B25J 9/0006
382/124

(Continued)

*Primary Examiner* — Yolanda R Cumbess

(57) ABSTRACT

In one example aspect, device is provided that is useful to allow delivery, storage, and pick up of goods with a drone comprising at least one of: a receptacle; a computing system; a camera; a multiplicity of physical sensors, wherein the multiplicity of physical sensors measure a physical measurement and an environmental measurement, said measurements including: a temperature measurement, a weight measurement, a humidity measurement, one of any other environmental measure measurement, and a motion measurement; a multiplicity of chemical sensors, wherein the multiplicity of chemical sensors detect the presence of a specified chemical; and wherein a set of inputs from the camera, multiplicity of physical sensors and the multiplicity of chemical sensors creates a record of a: a picture, a multiplicity of pictures, a video, a multiplicity of videos, and a data embodying readings from at least a sensor; and a device communicatively coupled to one or more other entities through at least one of a local network and an external network: to perform at least one of the actions of: transmit a set of data to the one or more other entities, receive the set of data from the one or more other entities, transmit a set of commands to the one or more other entities, and receive a set of commands from the one or more other entities, and wherein the one or more entities comprises at least one of a server, an owner device, a user device, a device coupled to an unmanned pickup/delivery agent.

13 Claims, 17 Drawing Sheets

(51) Int. Cl.
*G01D 5/00* (2006.01)
*G01N 33/00* (2006.01)
*B64C 39/02* (2006.01)
*B65G 1/137* (2006.01)
*G06Q 30/06* (2012.01)

(52) U.S. Cl.
CPC .............. *G01D 5/00* (2013.01); *G01N 33/00* (2013.01); *B64C 2201/128* (2013.01); *G06Q 10/0832* (2013.01); *G06Q 30/0619* (2013.01)

(56) References Cited

U.S. PATENT DOCUMENTS

2017/0011340 A1\* 1/2017 Gabbai .............. G06Q 10/0836
2017/0090484 A1\* 3/2017 Obaidi .................. B64C 39/024
2017/0213062 A1\* 7/2017 Jones .................. G06K 7/1417

\* cited by examiner

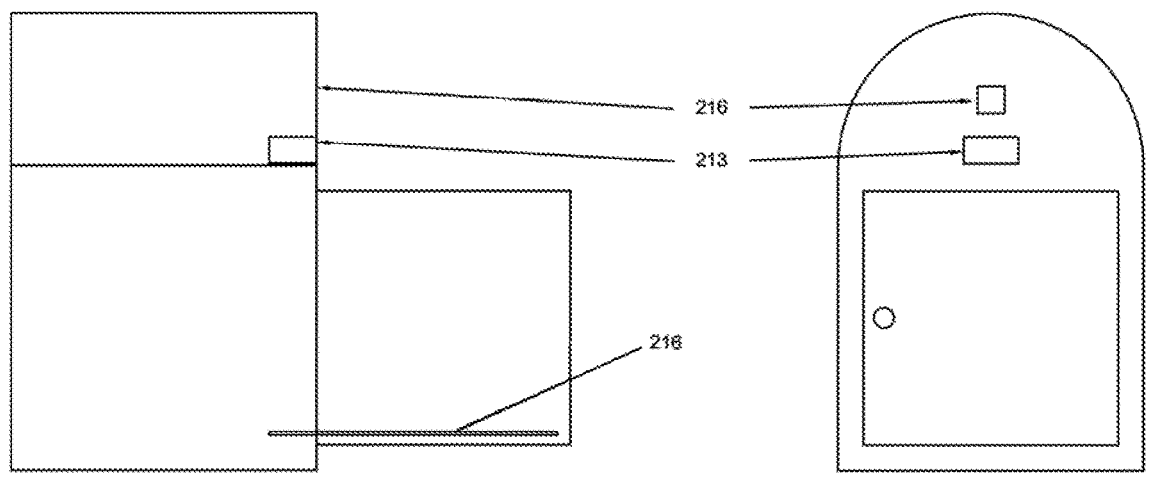
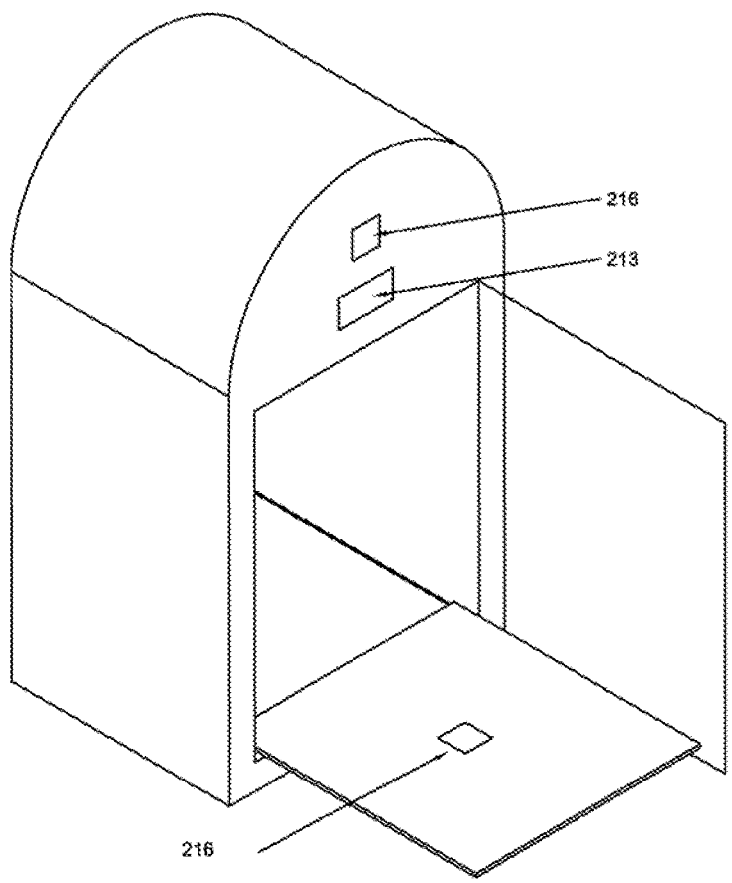
Figure 3A

| Usages Rights 261 | Pod Owner 240 | Pod Owner Delegate | Pod User 250 | Pickup/Delivery Agent 300 | Recipient 103 |
|---|---|---|---|---|---|
| Create/Edit Pod Owners | Yes | Yes | No | No | No |
| Delete Pod Owners | Yes | No | No | No | No |
| Create/Edit/Delete Pod Users | Yes | Yes | Yes | No | No |
| Delete Pod Users Created by Others | Yes | Yes | No | No | No |
| Create/Edit Own Usage Period | Yes | Yes | Yes | No | Yes |
| Edit/Delete Others Usage Period | Yes | Yes | No | No | No |
| Delegate Locking/Unlocking | Yes | Yes | Yes | No | No |
| Lock/Unlock Pod | Yes | Yes | Yes | Yes | No |

FIG. 7

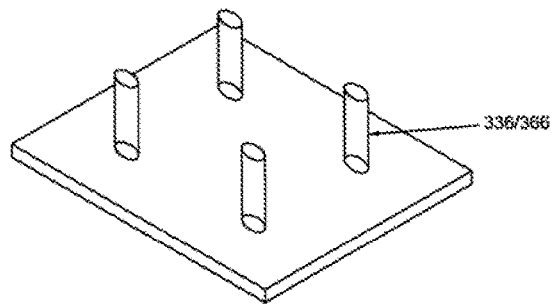 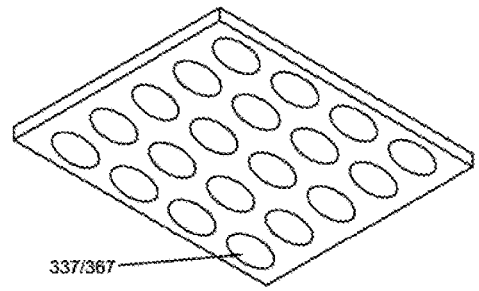
View from Above — View from Below
Figure 8A
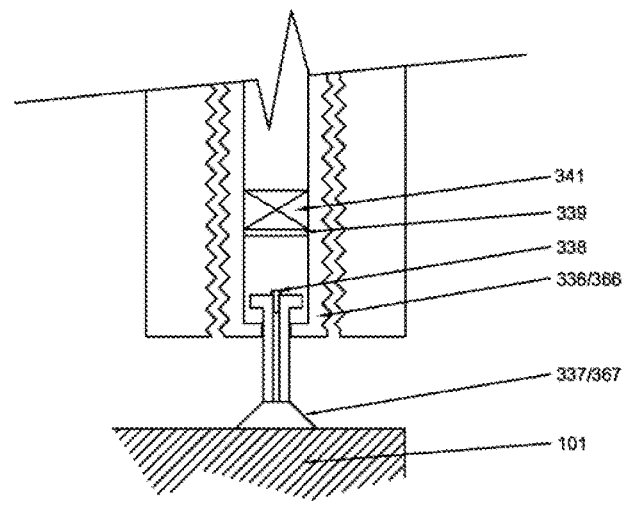
Figure 8B

SYSTEM AND METHOD TO ENABLE DELIVERY AND PICK UP OF PACKAGES USING PODS AND UNMANNED VEHICLES

CROSS-REFERENCE TO RELATED APPLICATIONS

This application claims priority to Indian Provisional Patent Application No. 201621025733, titled SYSTEM AND METHOD TO ENABLE DELIVERY AND PICK UP OF PACKAGES and filed on Jul. 27, 2016. This provisional application is hereby incorporated by reference in its entirety. This application claims priority to U.S. Provisional Patent Application No. 62/536,992, titled SYSTEM AND METHOD TO ENABLE DELIVERY AND PICK UP OF PACKAGES USING PODS AND UNMANNED VEHICLES and filed on Jul. 26, 2017. This provisional application is hereby incorporated by reference in its entirety.

BACKGROUND

1. Field

This description relates to the field of robotics and more specifically to systems and methods to enable delivery and pick up of packages using pods and unmanned vehicles.

2. Related Art

In recent years, E-Commerce has grown rapidly all over the world. In this model, customers place orders using the Internet and in some cases even using voice communication over a phone network. The order is then shipped from the E-Commerce retailer or an intermediary's warehouse to the customer's doorstep using a Common Carrier, a third-party logistics company, or the E-Commerce retailer's own shipping process. Often, the customer, that is, the recipient is not available at the delivery location to receive the product. Additionally, letters and documents that are delivered by Common Carriers and do not fit into normal mailboxes, or those requiring proof of delivery cannot easily be delivered when a recipient is not available at the delivery location to receive it. It has been estimated that worldwide, up to seventeen percent (17%) of deliveries are not completed because a recipient was not available. Redeliveries or even holding packages at brick-and-mortar locations add as much as forty percent (40%) to the shipping company's and therefore eventually the retailer's costs of delivery. This is a significant cost to retailers and can also cause extreme customer dissatisfaction.

More importantly, a number of surveys have found that customers may abandon an online shopping session because of inconvenient delivery options, in particular, uncertain delivery times. Respondents to surveys also confirmed the reverse—that they would be more likely to buy if the delivery time was convenient and predictable. Almost seventy (70%) of respondents said they would be more likely to buy online if the delivery conditions and/or timings were within their control. To serve this need, online retailers have begun to deliver packages at alternate locations such as a brick-and-mortar store where the customer can pick up packages at their convenience. Some common carriers will try to redeliver up to three times and then ask the recipient to pick up from their office or warehouse. However, the preferred location for delivery is and will remain the customer's doorstep or close to it such as a common parking area or lobby of a multi-tenant building. Even picking up at a brick-and-mortar store nearby involves disrupting one's normal commute, the hassle of finding parking and so on.

BRIEF SUMMARY OF THE INVENTION

In one example aspect, device is provided that is useful to allow delivery, storage, and pick up of goods with a drone comprising at least one of: a receptacle; a computing system; a camera; a multiplicity of physical sensors, wherein the multiplicity of physical sensors measure a physical measurement and an environmental measurement, said measurements including: a temperature measurement, a weight measurement, a humidity measurement, one of any other environmental measure measurement, and a motion measurement; a multiplicity of chemical sensors, wherein the multiplicity of chemical sensors detect the presence of a specified chemical; and wherein a set of inputs from the camera, multiplicity of physical sensors and the multiplicity of chemical sensors creates a record of a: a picture, a multiplicity of pictures, a video, a multiplicity of videos, and a data embodying readings from at least a sensor; and a device communicatively coupled to one or more other entities through at least one of a local network and an external network: to perform at least one of the actions of: transmit a set of data to the one or more other entities, receive the set of data from the one or more other entities, transmit a set of commands to the one or more other entities, and receive a set of commands from the one or more other entities, and wherein the one or more entities comprises at least one of a server, an owner device, a user device, a device coupled to an unmanned pickup/delivery agent, and a device carried by a human pickup/delivery agent, and wherein the device is communicatively connected to another device operated by the pickup/delivery agent.

BRIEF DESCRIPTION OF THE DRAWINGS

The present application can be best understood by reference to the following description taken in conjunction with the accompanying figures, in which like parts may be referred to by like numerals.

FIG. 3A shows exemplary views of a Pod.

FIG. 7 shows an example of Usage Roles and Usage Rights.

FIGS. 8A and 8B shows exemplary details of UAV/UTV mechanisms for gripping packages for pick up and delivery.

Figure 1A:
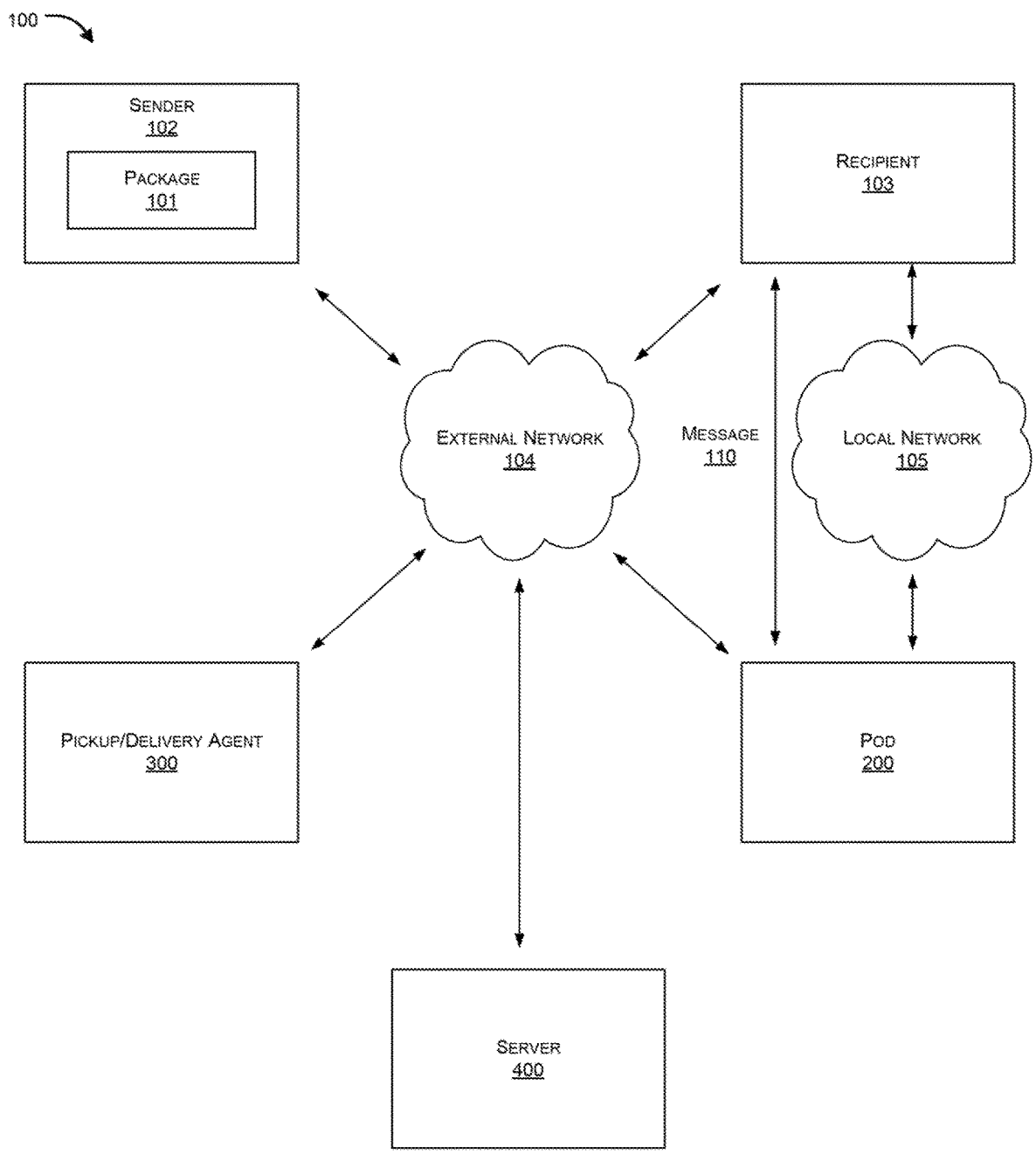
FIGS. 1A to 1F illustrate exemplary architectures of Pick-up/Delivery System showing Sender, Recipient, Pick-up/Delivery Agent, Unmanned Aerial Vehicle Pod, and Server with connections to External Network and Local Network.

The Figures described above are a representative set, and are not an exhaustive with respect to embodying the invention.

DETAILED DESCRIPTION

Disclosed are a system, method, and article of manufacture for enabling delivery and pick up of packages using pods and unmanned vehicles. The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments.

Reference throughout this specification to "one embodiment," "an embodiment," "one example," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, and they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Systems Overview

In the context of the present disclosure, it would be appreciated that there are several situations or relationships where goods are to be picked up or delivered, or left at common locations for shared use. For example, Merchants can deliver to Customers and in some cases pick up from them. A Merchant can include local merchants, hyperlocal merchants, restaurants, and of course online/remote merchants who can deliver goods to Customers. In fact, any organization, including a non-profit organization, service organization, political organization, and/or government agency (e.g. local emergency services and/or citizen initiatives) often implement the delivery of goods or letters to individuals or pick up of such goods/letters (collectively and interchangeably referred to as packages hereinafter) from them. There is therefore a significant market for a service that can deliver or pick up at the convenience of the user and in a cost-efficient manner.

The present disclosure proposes a system that allows easy pick up, delivery and shipping of tangible goods using electronically enabled boxes (hereinafter referred to as "Pods"), Delivery Persons/Agents, Senders, Recipients along with associated devices and manned/unmanned Vehicles (such as Terrestrial or Aerial Vehicles). The proposed system further includes a server (also interchangeably referred to as a "server system") connected to a network such as the Internet, which stores and transmits messages and information to the other parts of the delivery system including to the Devices, Pods and Vehicles.

In one embodiment, the present disclosure relates to a package brought to a Pod using for example an Unmanned Aerial Vehicle, Unmanned Terrestrial Vehicle or Human Carrier, and to reliably deliver or pick up a package. The disclosure further relates to the added security built into the process and also into the Pod to enable intended and efficient use thereof.

In one embodiment, the present disclosure relates to a Pod that can be unlocked by sending a message either from a remote or from a proximal location, wherein the Pod can be enabled to evaluate and decide whether to allow or disallow a delivery agent and/or recipient to unlock the Pod in order to place items in the Pod and/or remove items from the Pod for pick up. Unmanned Aerial Vehicle, Unmanned Terrestrial Vehicle In an exemplary embodiment, a computer-implemented system to automate pick up or delivery of at least one package, wherein the system includes a Pod, wherein the system is configured to receive, at a first computing device associated with a Pick-up/Delivery agent (simply referred to as an agent hereinafter), a first message (e.g. an SMS message, an instant message, an MMS message, etc.) identifying a Pod; and receive, at a second computing device associated with the Pod, a second message (e.g. an SMS message, an instant message, an MMS message, etc.) identifying the Pick-up/Delivery agent or information associated with Pick-up/Delivery agent's device such that, in an exemplary implementation, the Pick-up/Delivery agent contacts (e.g. through an SMS or a phone call or any other appropriate signal, etc.) and unlocks the identified Pod based on at least a part of the first message (e.g., an unlock code that forms part of the first message or even an identity of sender of first message represented for example by the Caller Identification, etc.), and completes the designated action of pick up and/or delivery of the package when at least a part of the second message is complementary to information in the first message. Upon completion of the action, the Pod is relocked and may be rendered unavailable until another/same agent uses another authentic message to unlock the Pod.

In one embodiment, the agent receives the first message, and the Pod receives the second message from any or a combination of a Pod Owner, a Pod User, a Pick-up/Delivery agent and a Pick up and Delivery System Server. In another aspect, the Pick-up/Delivery agent can be any one of or any combination of a human agent, an unmanned vehicle, a manned vehicle.

In one embodiment, the Pick-up/Delivery operation can also include capturing, using a camera mounted in the Pod, or mounted on or carried by the Delivery Agent, a picture or a video of the actual placing of the package into the Pod and the securing and/or closing of the Pod. Such an image/photo/picture/video can be time-stamped and may also take the form of other means (e.g. using sensors) of recording pick up and delivery enabled by the computing resources available. This can then constitute proof of delivery as required by the sender or by law or both. In one embodiment, one or more cameras are positioned on/in the Pod in such a way that the cameras record pictures or video below the package but can be moved out of the way during pick up or delivery.

In one embodiment, the present disclosure provides a multiplicity of methods for locking, unlocking and performing various operations on a Pod in case one fails and/or when a technology is not available either on the Pod or on the operator's device. The present disclosure further relates to an integrated method that uses the same components for Pick up and Delivery.

One may appreciate that the disclosed techniques provide many advantageous technical effects including Pick-up/Delivery of one or more packages, locking/unlocking/use/configuration of pods, configuration of UAV/UTV, among many other technical aspects.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

In the present description of the invention(s), for the purpose of readability, several longer names have been shortened to their acronyms after being articulated one or more times. For example, Unmanned Aerial Vehicle may be shortened to UAV, and Unmanned Terrestrial Vehicle to UTV. In some cases, the longer names are partially "acronymized", for example Unmanned Aerial Vehicle Computing System may be shortened to UAV Computing System and either nomenclature can be used to describe the same entity.

Further, some technical expansions are used in their shorter, ordinary, or everyday use formats and should be taken to represent their expansions and specifications as appropriate. In the current description, wherever any of the above technical terms are encountered, they can be substituted with the corresponding specification and/or description including specifications of sub-protocols. The following are technical terms and their corresponding specifications or expansions:

ATM—Asynchronous Transfer Mode
Bluetooth—IEEE 802.15.1
Ethernet—IEEE 802.3
FTP—File Transfer Protocol
HTTP—Hyper Text Transfer Protocol
GPS—Global Positioning System
IR—Infrared
NFC—Near Field Communication typically based on existing radio-frequency identification (RFID) standards including ISO/IEC 14443 and others as defined by the NFC Forum and others.
RFID—Radio Frequency Identification
SMS—Short Messaging System
Wi-Fi—IEEE 802.11 a/b/g/n and other variants (including, for example WLAN, WiMAX, etc.)

In the description of the present invention, again for the sake of brevity, when describing certain processes, the description often names the whole while actually referring to the part. In other words, when a part of an object performs an operation, we say that the object itself has performed that action. For example, instead of saying " . . . a Message is sent by Pod Computing Application via Pod Communication Module . . . " the description may say that " . . . a Message is sent by Pod . . . . "

Throughout the following discussion, numerous references will be made to devices, servers, services, interfaces, engines, modules, clients, peers, portals, platforms, or other systems formed from computing devices. It should be can include one or more computers/computing devices operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable media or even transitory media (for example that received in real time as a message) storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial transaction protocols, and the like or other electronic information exchange methods. Data exchanges can be conducted over a packet-switched network, the Internet, LAN, WAN, VPN, or any other type of network.

It is assumed that all electronic devices are powered by a battery, an electrical mains connection, other forms and sources of electricity such as solar power, thermal power or any other conceivable power source, and this is not part of the description due to its obviousness.

The present disclosure presents the use of a "Device" or "Devices" for various aspects of the invention. Device may include a display mechanism such as an LCD/LED screen, an input mechanism such as a keyboard or a virtual keyboard on a touchscreen (the latter may be the same as the above-mentioned LCD/LED screen). It should be noted that in addition to the use of any of these devices within the parameters of this invention, said devices may additionally be used for purposes outside the scope of the present invention and this should not be seen as limiting in any way the scope of the present invention, unless specifically mentioned or repugnant to the context based on the understanding of a practitioner versed in the art. As an example, a Pod Owner Device may be a typical Smartphone commonly used by a person, but may have appropriate applications and configurations that additionally allow it to be used as a Pod Owner Device.

Thus, any reference to a "Device" such as Pod User Device or Pod Owner Device or Direct Sender Device should be understood to encompass at least the above description of "Device", including but not limited to the processes and options taught. However, the above description should not be perceived as a limitation in any way unless explicitly stated in the disclosure or repugnant to the context based on the understanding of a practitioner versed in the art.

Typically, a "Device" is enabled with a "Computing System" and it is further to be appreciated that any such Computing System may be implemented as intrinsic to the Device severally or jointly known for example as a conventional computer system, an embedded controller, a laptop, a desktop, a server, a dedicated board, a computer-on-a-chip, a virtual machine, a mobile device, a smartphone, a set-top box, a kiosk, a vehicular computer, a television with one or more processors embedded therein and/or coupled thereto, a customized machine, any other hardware, or any combination or multiplicity thereof, having at least one processor (e.g., ASIC, FPGA, DSP, x86, x64 ARM®, ColdFire®, GPU, etc.) configured to execute software instructions and also including computer readable tangible transitory medium such as Random Access Memory (RAM) and non-transitory data storage such as a hard disk, Read Only Memory (ROM), flash storage or any such component(s). The computing system may be a distributed system configured to function using multiple computing systems interconnected via a data network, a bus system or any combination or multiplicity thereof and may be capable of running an operating system and one or more software applications together termed "Computing Application".

Thus, any reference to a "Computing System" such as Pod Computing System or UAV Computing System should be understood to include the above description of "Computing System", including but not limited to the processes and options taught. However, the above description should not be perceived as a limitation in any way unless explicitly stated in the disclosure or repugnant to the context based on the understanding of a practitioner versed in the art.

Similarly, it is also to be appreciated that a "Communication Module" may be implemented as a set of electronic components including one or more sensors and emitters each of which operate at a known frequency or frequencies and implemented according to a specific protocol, the combination of sensors, emitters and protocols being referred to as a "communication technology". Now to teach, as an example, "Direct Recipient Device Communication Module" (e.g. Customer's device such as mobile phone or smartphone) may implement (for example) a Bluetooth receiver and emitter and other electronics connected to the Bluetooth receiver/emitter now called Bluetooth technology or simply Bluetooth. Other technologies such as GPS, Wi-Fi, Ethernet, RFID or even proprietary protocols may be used, either individually or in combination without prejudice to the intent of the teaching of the operation of "Direct Recipient Device Communication Module" or for that matter any "Communication Module" described in this disclosure. "Communication Module", using such technologies, can initiate, establish, or connect to an External Network or a Local Network or both, the purpose of such connections being to send/receive one more Messages to/from other components of Pick up and Delivery System, or even to devices and systems not included in Pick up and Delivery System. It is also possible that the Direct Recipient Device Communication Module (interpreted to include any other like device module associated with sender, server, Pod, Agent, or Recipient) can receive a Message using one technology and transmit the same Message using the same or a different communication technology. Direct Recipient Device Communication Module is also capable of initiating a connection to the same device using a second communication technology on failure to initiate a connection with said device using a first communication technology.

In an aspect, "Communication Module" (which can be, for instance, be configured to enable a Recipient to communicate one or more messages/calls/packets through computing system) can be capable of receiving at least a message that is optionally encrypted, wherein the message can additionally contain identification information that identifies, for instance, sender of the message and/or the intended recipient, such identification information preferably not being encrypted such that if the message received is not intended for Device, the message can be retransmitted to a different Device designated as a recipient device, directly or through yet another device to the intended recipient. When a message is received by Communication Module from an external source, it is transmitted to a "Computing System" that includes an "Computing Application" and a "Data Storage", the Computing Application being capable of decrypting at least a portion of the Message if at least a portion of it is encrypted. Computing Application further analyzes, interprets, and optionally acts upon the content of the decrypted message or the raw message if not encrypted. Communication Module can also be capable of sending a Message typically initiated by Computing Application, and optionally at least a portion of Message is encrypted.

In an aspect, Direct Recipient Device Communication Module (to include the communication device itself) may include more than one type of communication sensors and emitters with associated protocols. For example, the Direct Recipient Device Communication Module may include Bluetooth as well as Wi-Fi capabilities and either or both may be enabled at any given time, thus allowing receipt and transmission of a Messages and backup or alternate copies of the same Messages simultaneously.

Thus, any reference to a "Communication Module" such as Pod Communication Module or UAV Communication Module can be understood to include the above description of Communication Module, including but not limited to the processes and options taught. However, the above description should not be perceived as a limitation in any way unless explicitly stated in the disclosure or repugnant to the context based on the understanding of a practitioner versed in the art.

Similarly, a Device using a Computing System and enabled with a Communication Module may be further enabled with a "Computing Application" that is capable and configured with an appropriate code and data to activate associated communication module or modules, configure such module(s) with appropriate passwords, identifications, protocols, ports and the like; such configurations capable to send and receive messages through such a module(s). The Computing Application may also be capable of operating certain components of the Device including mechanical parts/assemblies, indicators, sensors and the like as well as receiving information from such components. Further, Computing Application is capable if required, to generate as needed or use previously stored encryption/decryption keys and encryption/decryption algorithms as well as also be capable to convert addresses into 3Dimensional (3D) coordinates where an element of the system is physically located.

Thus, any reference to a "Computing Application" such as Pod Computing Application or UAV Computing Application can be understood to encompass at least the above description of Computing Application, including but not limited to the processes and options taught. However, the above description should not be perceived as a limitation in any way unless explicitly stated in the disclosure or repugnant to the context based on the understanding of a practitioner versed in the art.

In many cases, a device may also include "Data Storage" where aforesaid operating system, software applications and information may be stored in the form of files (including executable files), databases and so on. Data Storage can conceivably store the above named information in a local storage and at least a portion of it in external data storage (for example on a server) using backup, replication, virtualization or any other technique not repugnant to the context. Data Storage may also contain certain algorithms and keys used to encrypt and decrypt data sent to other devices or received from other devices. Data Storage may also contain certain instructions in the form of rules that, when interpreted by Computing Application, prevent a user, another device or a system from performing certain actions, or limiting the scope of certain actions. Such a set of instructions is now designated as Device Meta Instructions.

Thus, any reference to a "Data Storage" such as Pod Data Storage or UAV Data Storage can be understood to include the above description of Data Storage, including but not limited to the processes and options taught. However, the above description should not be perceived as a limitation in any way unless explicitly stated in the disclosure or repugnant to the context based on the understanding of a practitioner versed in the art.

It should be appreciated that although "Device" and its components have been explained with respect to an example or generalized device and generalized descriptions of said device or its components, the structure, construction, module(s), and layout/features of the device and various components of the device, including but not limited to, computing system, communication module, computing application, data storage, and other aspects of said device, can be applied to other like computing devices configured, for instance, with any other entity/component that forms part of the proposed Pick up and Delivery System or is operatively coupled with the proposed Pick up and Delivery System. Although the function of each such device may be contextually different, the basic fundamental functionality of the various components such as of the communication module or of the data storage may be intact, and hence, for brevity of the instant specification, all such modules in such detail will not be explained again for each device, except for the difference in their functionality when compared with the example presented above. It should also be noted that, in the description, we use "Synecdoche" to refer to various aspects of this invention. As an example, we refer to Computing System by referring, for example, to Device and therefore, in this description, any reference to Device "determining", "calculating", "computing", or similar words should be taken to mean Computing System is performing such a task. Similarly, any reference to "connecting", "connects", 'communicating", "communicates", "sending Message", "receiving Message" and similar terms should be taken to mean that Communication Module or at least a component of Communication Module is performing such a task. In this manner, all devices and associated components along with their functions may be referred to, using this abbreviated format. In case of conflict, the specific descriptions that follow will supersede the general descriptions.

Turning now to the drawings, in which like numerals indicate like, but not necessarily identical elements throughout the figures, a system architecture and example embodiments are herein described in detail. With a view to illustrating the purpose of the various components of the system only to enumerate their respective qualities and structure and not the embodiments of the invention we now present a description of an example System Architecture below. Throughout the discussion of system architecture and example embodiments, it should be understood that the terms "data" and "information" are used interchangeably herein to refer to text, images, audio, video, scripts, executables, files or any other form of information that can exist in a computer-based environment and may be stored as files, databases, data structures and any other format or structure used in a computer based environment.

System Architecture

FIG. 1A illustrates an exemplary block diagram depicting a Pick up and Delivery System 100 in accordance with certain example embodiments where the purpose of Pick up and Delivery System 100 is to pick up and/or deliver a Package 101 from a Sender 102 to a Recipient 103. Package 101 may be any item or a multiplicity of items sent by one individual or business to another. As examples, Package 101 may be the fulfillment of an eCommerce order or a local purchase, made either online or in person, a food delivery by a restaurant or any vendor or even a friend, currency left as payment for a vendor or a payment for any purpose, parts or supplies used by an individual or a business, gifts, samples or any other such item or items. Package 101 may also be any object(s) exchanged between two persons such as books, currency, food or any other such item regardless of whether or not any payment occurs. Sender 102 and Recipient 103 may either or both be an individual or a business. For example, a retailer (i.e. Sender 102) who has taken an order from a customer (i.e. Recipient 103) would deliver the order as Package 101 to the Recipient 103 in an expeditious manner, or the opposite i.e. a customer (in this case Sender 102) may return an item to the retailer (in this scenario Recipient 103).

A Third-Party Logistics Provider 104 provides shipping services including one or more of Pick up, Delivery, Logistics Support, Tracking, Pick-up/Delivery Agents and so on. For example, Third Party Logistics Provider 104 may be an owner of a fleet of unmanned vehicles providing Pick up and Delivery Services. Third Party Logistics Provider 104 may initiate Pick-up/Delivery process as a result of a separate eCommerce or other type of transaction in which it is not involved. In some cases, Sender 102, an eCommerce Retailer (or any other merchant) and Third-Party Logistics Provider 104 are the same. Third Party Logistics Provider 104 can also apply to an aggregate of providers who provide the services ascribed to such an entity.

As depicted in FIG. 1A, Pick up and Delivery System 100 may include one or more External Network(s) 105 and Local Network(s) 106 that are configured to allow communication between the various components of the Pick up and Delivery System 100 and even entities or components not a part of the Pick up and Delivery System 100. These networks can be temporary or permanent and can be established by communication modules of various devices, wherein the communication modules may be associated with a computing system and may be under the control of a computing application that is capable and configured with an appropriate code and data to activate associated communication module or modules, configure such module(s) with appropriate passwords, identifications, protocols, ports and the like; such configurations capable to send and receive messages through such a module(s). External Network 105 can include at least one of a local area network ("LAN"), an External Network ("WAN"), an intranet, an Internet, storage area network ("SAN"), a personal area network ("PAN"), a metropolitan area network ("MAN"), a wireless local area network ("WLAN"), a virtual private network ("VPN"), and a cellular or other mobile communication network, using one or more technologies and protocols such as Wi-Fi, Ethernet, Bluetooth, IR, or any other technologies or combination thereof or any other appropriate architecture or system that enables or facilitates the communication of signals, data, and/or messages. The Internet as well as the public telecommunication infrastructure and one or more components of the same are included in this architecture of the Pick up and Delivery System 100. External Network 105 can include, in whole or part, any combination of such networks that connect external devices and systems to any component of the Pick up and Delivery System 100.

External Network 105 may also include a private WAN, VPN or some other such network deployed and/or operated by any entity including but not limited to a logistics company, a retailer (offline, online or combined), a recipient/sender of the package itself or can be another entity/person who owns and manages/controls any portion of the Pick-up/Delivery System 100, a multiplicity of such entities, or any other organization or entity that deploys, or causes to be deployed, and/or operates or causes to be operated such a network usable alone or in combination with other public and private networks. As an example, certain components of Pick up and Delivery System 100 may be enabled with an SMS gateway, enabling SMS communication with internal and external devices through the public telecommunications network.

Local Network 106 can typically be created by and between components of the Pick up and Delivery System 100. Local Network 106 can include any of the aforesaid technologies and configurations described for External Network 105, but may be limited to interactions within the Pick up and Delivery System 100 and between components of the Pick up and Delivery System 100 including both permanent and temporary components and those that are only partially part of the Pick up and Delivery System 100. Thus, Local Network 106 can be useful for enabling or facilitating communication of signals, data, and/or messages within the Pick up and Delivery System 100. It should be noted that components of the Pick up and Delivery System 100 that are ordinarily designed to communicate between each other using Local Network 106 may communicate with each other by using components of External Network 105 that are not part of the Pick up and Delivery System 100, particularly as a fail-over measure i.e. when a temporary or permanent failure to establish communication between components of Pick up and Delivery System 100 occurs, portions of External Network 105 may be used until Local Network 106 can be established or re-established. Also, a component of the Pick up and Delivery System 100 such as an external server may communicate with other components of the Pick up and Delivery System 100 through an External Network 105, a Local Network 106 or a combination of both.

In the process of delivering or picking up a Package 101, or performing other operations of Pick up and Delivery System 100, communication may be established between a multiplicity of components of the Pick up and Delivery System 100 and may include one or more messages, each such message now called Message 110. Messages 110 may be generated, transmitted, and received by the various components of the Pick up and Delivery System 100, and may also be transmitted between components of the Pick up and Delivery System 100 as well as devices, components and systems that are not part of the Pick up and Delivery System 100. Message 110 can be a status message, a control message (a command), a confirmation message and or can be used for any other purpose/function, or even a combination of such. Message 110 may be optionally encrypted at least in part so that it can only be decrypted by a device or person that is meant to receive it and therefore has or can obtain the necessary decryption information such as the decryption algorithm, key, nonce and any other required information and may not be decrypted by a device or person not meant to receive the message and does not have and cannot obtain required decryption information. In some cases, Message 110 may contain no substantive information, but sending or receipt of said Message 110 or even the connection request that is part of sending Message 110 from a first device to a second device may be sufficient to meet a preferred condition and such message may be treated as substantive. As an example, a phone call where the caller's phone number (obtained for example using Caller ID), the time of the call, number of rings and any other conceivable uniquely obtainable identifier, or combinations of these may be treated as a Message. As mentioned, Message 110 may be encrypted at least in part, and a part that is not encrypted, if present, can be used, for instance, for forwarding Message 110 to correct addressee, showing purpose of Message 110, showing sender of Message 110, among other like purposes.

As an example, when a Package 101 is to be sent by Sender 102 (a Retailer, an intermediary such as a third-party shipping/logistics company, an individual or any other type of sender) to a Recipient 103, Sender 102 may send a Message 110 to Recipient 103 with relevant shipping details. Message 110 may be sent in any format and by any means, including but not limited to SMS, Voice, Email, a dedicated app, or a general messaging app such as WhatsApp®, Viber®, Blackberry® and the like. Message 110 may be sent directly to Recipient 103 or via intermediate devices or systems such as a general-purpose server or one owned and operated by Sender 102 or a third party such as a logistics company. Message 110 may be transmitted either via an External Network 105, a Local Network 106 or both using various protocols, such as Ethernet, ATM, HTTP and any other appropriate protocol or combination thereof. In many cases, any of the components of Pick up and Delivery System 100 may attempt to send a Message 110 by one protocol and upon failure may send it via another protocol. In other cases, a Message 110 may be transmitted between a first device and a second device using one protocol, and then transmitted from the second device to a third device using a different protocol. For example, one device may transmit Message 110 via Bluetooth to a second device, and then this second device transmits to a third device using Wi-Fi. Similarly, Message 110 may be sent via External Network 105 from a first device to a second device, and the same message may be transmitted to a third device using Local Network 106; the opposite path may also be taken by Message 110. Message 110 may be sent through any interface including but not limited to a Device in Pick-up/Delivery System 100, the World Wide Web, an independent App, Voice based interaction with a manned or automated customer service entity, Interactive Phone System or any method not repugnant to the context. Messages 110 may also be sent in any format and by any means, all of which are well within the scope of the present disclosure.

In an exemplary implementation, when a Message 110 is received, one or more of the following steps are performed: Message 110 is stored as data to be used later, Message 110 is decrypted, Message 110 is analyzed for instructions, or Message 110 is further transmitted to another device. The above steps may be performed in any order and each may be performed more than once as relevant for a particular operation.

Message 110 may have an encrypted portion and an unencrypted portion and may have a leading flag comprising one or more alphanumeric characters signifying whether it is wholly or partially encrypted. In addition, when a Message 110 is meant to be transmitted from one device to a second device and there are or are expected to be intermediate devices transmitting said messages, then Message 110 may contain an unencrypted portion that includes the addressee. Alternately, the portion containing the addressee may be encrypted with an algorithm and/or key that is known to every component of Pick up and Delivery System 100, so that addressee information may be obtained by intermediate components and said Message 110 can be transmitted to the addressee or to another component in order for it to be forwarded to its ultimate destination.

Message Encryption/Decryption Information 111 saved in components of Pick up and Delivery System 100 contains keys, algorithms and combinations of keys and algorithms that can be used to encrypt and decrypt messages. These components have, stored in their respective Data Storage, certain algorithms and keys, together used for encrypting and decrypting messages sent between devices or to other components of Pick up and Delivery System 100, or even outside Pick-up/Delivery System 100, and named Message Encryption/Decryption Information 111. Device Computing Applications may also generate a key or choose from an existing set of stored keys, and then also choose at least an encryption algorithm from the list of algorithms in the system. Further, keys and algorithms may be obtained from an external source such as a Server or a service to which the device may connect, for example over the Internet and which may be operated by, for example, a third-party provider of keys and algorithms or any other entity. A location of at least one such Server saved as a Fully Qualified Domain Name (FQDN), or IP address, or other means of identifying and locating a server plus authentication information if required to obtain additional Message Encryption/Decryption Information 111 are also saved in Message Encryption/Decryption Information 111 in each device. Also included in Message Encryption/Decryption Information 111 are means of locating additional such Servers and authentication information if required to obtain additional Message Encryption/Decryption Information 111. At intervals, devices obtain additional algorithms and keys and exchange the various combinations of key and algorithm with each other as Messages 110. Henceforth, any messages that pass between these two devices may be encrypted with these new keys/algorithms. A first device may transmit a different combination of key and algorithm to a second device as Message 110. Such a Message 110 may be encrypted using an existing key/algorithm combination, and therefore can be decrypted by second device but includes an instruction to second device to use the new key/algorithm combination henceforth, or for a period of time, or for a certain number of transactions. Second device decrypts the message using the existing key/algorithm combination and then may acknowledge Message 110 with a Message 110$b$, the latter encrypted with the new key/algorithm combination thus making a success acknowledgement. At intervals randomly calculated by a first device based on time, a number of deliveries or any other marker or any combination of these, or when initiated by first device, second device or any other entity, such new key/algorithm combinations may be sent by devices to each other and each combination is used to encrypt and decrypt all communication between devices until it is changed again. Thus, security is considerably enhanced because constantly changing keys and algorithms greatly reduce the possibility of a current combination of keys and algorithms from being discovered and the system therefore effectively secures communication between devices.

Package 101 may also include a Package Information Device 121 which is an electronic device such as a chip or board using a technology such as RFID, Bluetooth, NFC, or any other similar technology, and contains aforementioned information about one or more of Package 101, Sender 102, Recipient 103, Pick-up/Delivery Information, and any other relevant information. Sensors that are part of various components and devices in Pick up and Delivery System 100 (or even outside of such system) read said information from Package Information Device 121 and store it or use as needed.

Package 101 has certain physical dimensions and weight and may have other information associated with the package such as that required for security or handling purposes, taxes, duties, customs, special delivery instructions and so on and these are together and severally called Package and Shipping Information 130. Package and Shipping Information 130 may also include information about linked entities such as Sender 102, Recipient 103 and others as well as information related to the delivery process such as shipping modes, delivery date and so on.

In an aspect, a Package 101 needs to be delivered to a location where n device such as a Pod is available. To facilitate this, Pick-up/Delivery Graphic 131 such as a bar code, QR code, image, graphic or other means that Direct Recipient 150 has been placed on a surface capable of receiving the package. Pick-up/Delivery Graphic 131 may be printed, engraved, displayed on an LED or LCD screen, via a sequence of static or blinking lights, or otherwise displayed on a surface, in a multiplicity of locations and in a multiplicity of ways including any combination of a plurality of alphanumeric characters, a symbol, a plurality of symbols, a bar code, a QR Code, an image, a hologram or any other form of representation available now or in the future and can be read by scanning with a camera, QR Code Reader, Bar Code Reader or any appropriate device, any combination of such devices, or any device that simulates such devices or performs substantially in the same manner as such devices. Pick-up/Delivery Graphic 131, or its representation (graphic, numeric or any other form of representation) can also be stored and transmitted as needed to facilitate Delivery.

In the below descriptions of various embodiments, Messages can include at least a unique number that is incremented whenever a new message such as a reply is sent. For example, if a first entity in this embodiment sends a first Message 110$z$ to a second entity (or simultaneously to a second and third entity), it comprises for example at least the numeric value "1". A reply sent in response by the second entity or by the third entity, as say, Message 110$y$ and Message 110$x$ respectively increments the numeric value of "1" and therefore includes the numeric value "2". Both entities may send a message and in this case, both Message 110$y$ sent by second entity and a Message 110$x$ sent by third entity will comprise said numeric value of "2". Now, if first entity were to respond to either or both entities, with say a Message 110$w$, numeral "3" would be included in said message, which helps to sequence messages and prevent overlaps especially when a message is delayed. Note that the numerals 1, 2 and 3 are shown as examples and any sequential numerals or even alphabetic or other characters that have a recognizable sequence will be appropriate for the purpose. In a preferred aspect, and in particular when more than two devices are communicating as described, the sequence need not have proximal elements. The above example shows for simplicity that the sequence numbers are "1", "2", "3" and so on but a preferred example sequence may be for example use "10", "20", "30" and so on for one device, "10", "20", "30" and so on for the second device and "10", "20", "30" and so on for the third. Also, once pair of devices may use a different system than the other pair. For example, one pair may use alphabetic characters and the other communicating pair may use numbers. More complex sequences and combinations are also possible and the above description should not be seen as limiting the present invention in any way.

Message 110, when sent by a device (for example through its communication module) may also include a unique ID of a device which helps receiving device identify the sending device. This unique ID can be, for example the machine ID (such as found in the chip of the respective computing system) or a MAC Address or it can be an ID assigned by a server which manages various devices or user/device logins and the utility of aid devices or roles of said users within Pick up and Delivery System 100, or any other uniquely identifiable ID that is appropriate.

In an example, Package 101 may contain passive or active electronics or components that emit or respond to and emitter such as RFID, Bluetooth which may be used to accurately locate the package by Pick-up/Delivery Agent 300 or even by systems outside the present invention (i.e. a shipper's logistics systems). These one or more devices are jointly or severally called Package Information Device 121.

Package Information Device 121 includes Package Information Device Computing System 122 which in turn is enabled with Package Information Device Computing Application 123, Package Information Device Data Storage 124 and Package Information Device Communication Module 125 each of which has been generally described above and hence will not be described again for the sake of brevity. Package Locking Mechanism 126, Package Electro-Mechanical System 127 and Package Camera 128 are also similar in scope and function to equivalent elements of other devices and will be further elaborated in the embodiments. In particular, Package 101 may be the result of detaching or converting certain other elements of this invention and their elements correspond to the elements described above.

Package Information Device 121 may include at least a Package and Shipping Information 130 that includes relevant information about Package 101. Package and Shipping Information 130 may be encoded into a Package Graphic 129, and said Package Graphic 129 may also contain other information as necessary such as Pick-up/Delivery Payment 302, Pick up Address 304, Pick up Information 305, Delivery Address 306, Delivery Information 307, and even Pod UID 211 (of a Pod 200 to which a Package 101 is to be delivered) for successful delivery of Package 101. Package Graphic 129 may be printed, engraved, displayed on an LED or LCD screen, via a sequence of static or blinking lights (by attaching enabling hardware to Package 101), or otherwise displayed on Package 101, in a multiplicity of locations and in a multiplicity of ways including any combination of a plurality of alphanumeric characters, a symbol, a plurality of symbols, a bar code, a QR Code, an image, a hologram or any other form of representation available now or in the future. Package Graphic 129 or its representation (graphic, numeric or any other form of representation) can also be stored in Package Information Device Data Storage 124 and may additionally be stored as required by various embodiments in a plurality of servers, devices operated by users and owners of pods and delivery agents amongst others.

Package Information Device 121 may also include a Package Homing Device 120 consisting of a device that sends out a signal using any protocol or technology such as but not limited to an audio signal, a radio frequency signal, a visible signal (for example using one or more LEDs, a small LED/LCD screen and so on), a laser, a message broadcast using for example Bluetooth, Wi-Fi and so on. The signal may be transmitted continuously or at intervals and may be used by other devices to ascertain the location of the package and possibly also compute its distance from said device. Package Homing Device 120 may send out a signal at a time interval determined by at least one of an interval created by default at the time of manufacture and an interval configured by at least one of Sender 102, Recipient 103, Third Party Logistics Provider 104 or any other entity or device authorized and capable of configuring Package Homing Device 120. Package Homing Device 120 may be a complete device in itself, or may be formed from the other components of Package Information Device 121 (for example with a combination of Package Information Device Computing Application 123 and Package Information Device Communication Module 125). In an aspect, the signal broadcast by Package Information Device 120 may include information about Package 101 such as a unique tracking number that can further be linked to Package and Shipping Information 130 via a URL or other means. In another aspect said broadcast signal may include a uniquely recognizable code that can be read and recognized by other devices that are seeking said package. Finally said signal can include both above mentioned information that is a tracking number and a code, each being alternately broadcast. In an example, Package Homing Device 120 has a row of multi-colored lights which flash in a given sequence, portions of said sequence representing an alphanumeric character (for example using Morse code) which can be captured and analyzed by a mobile device, said mobile device equipped with a camera and computing software that can capture at least an image of said lights and analyze their intensity and size at intervals. By determining that the size of the lights is increasing in the frame of the camera said mobile device determines that it is moving towards said lights and therefore towards Package Homing Device 13. Therefore, said mobile device determining that the size of the lights is decreasing with respect to the camera, said mobile device can deduce that it is moving away from said lights. Similarly, image analysis software can determine the intensity of the lights and if intensity is increasing determine that said device is moving toward Package Homing Device 120 and vice versa.

In an exemplary implementation Sender 102 wants to send a Package 101 directly to any recipient and does not have a dedicated, secured location where Package 101 can be picked up. Further, Sender 102 wants to use the Pick-up/Delivery System 100 to transport Package 101 to Recipient 103; hence Sender 102 is now called Direct Sender 140. In another example, a recipient wants to request a Package 101 from Sender 102 and therefore initiates a Pick up. Here too, Recipient 103 does not have access to a dedicated, secured location and is therefore designated Direct Recipient 150.

Direct Sender 140 may possess a device now called Direct Sender Device 141 that may include Direct Sender Device Computing System 142, and at least a Direct Sender Device Communication Module 145. In an aspect, Direct Sender Device 141 may be implemented as described above in the general description of "Device", Direct Sender Device Computing System 142 (DSD Computing System 142) may be implemented as described above in the general description of "Computing System" and may further implement a Direct Sender Device Computing Application 143 (DSD Computing Application 143). Direct Sender Device Communication Module 145 may be implemented as described in the general description of "Communication Module" above. DSD Computing Application 143 may be implemented as described above in the general description of "Computing Application" and may interface with Direct Sender Device Data Storage 144 (DSD Data Storage 144) which in turn may be implemented as described above in the general description of "Data Storage". DSD Data Storage 144 may contain certain instructions as described above in the general description of Meta Instructions and these are now designated as Direct Sender Device Meta Instructions 146. DSD Computing Application 143 is also capable of converting addresses into 3Dimensional (3D) coordinates where Package 101 may be picked up or delivered.

Figure 1B:
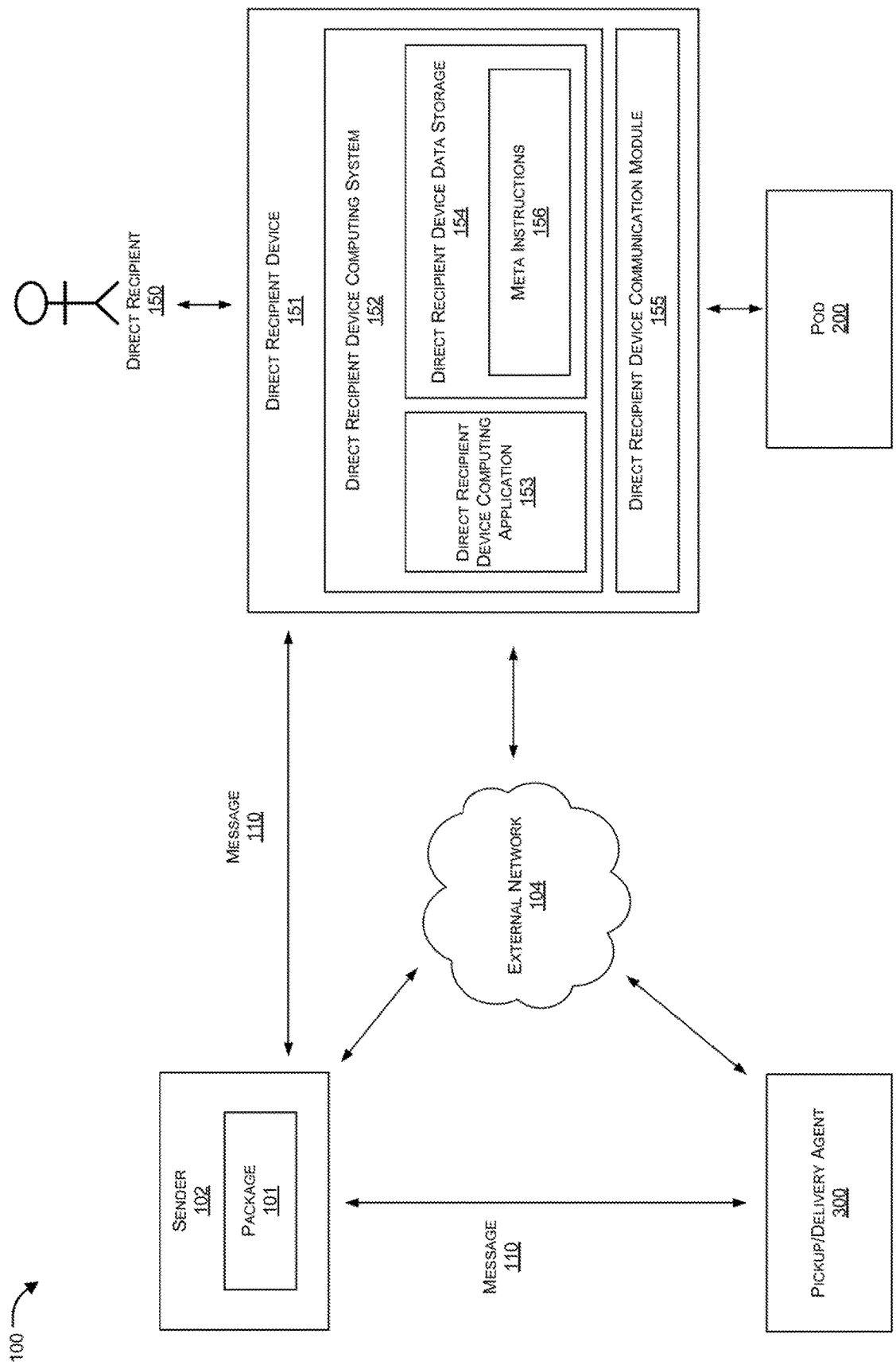

In an exemplary implementation, with reference to FIG. 1B, the present disclosure includes a method of manual pick up and delivery of a package to a Recipient 103, said recipient now called Direct Recipient 150, wherein the Direct Recipient 150 may not own a dedicated, secure delivery location or may own such a location but may choose to receive a specific delivery by this manual method. To communicate with various other parts of the system, for example with Sender 102, Direct Recipient 150 may possess a device now called Direct Recipient Device 151 that may include Direct Recipient Device Computing System 152 (DRD Computing System 152), and at least a Direct Recipient Device Communication Module 155. In an aspect, Direct Recipient Device 151 may be implemented as described above in the general description of "Computing System". Direct Recipient Device Computing System 152 may be implemented as described above in the general description of "Computing System" and further implement a Direct Recipient Device Computing Application 153 (DRD Computing Application 153) as described above in the general description of "Computing Application". DRD Computing System 152 also enables, through data storage ability of the DRD Computing System 152, a Direct Recipient Device Data Storage 154 which may be implemented as described above in the general description of "Data Storage". A set of instructions as described above in the general description of Meta Instructions may be stored in DRD Data Storage 154 and is now designated as Direct Recipient Device Meta Instructions 156 (DRD Meta Instructions 156). Computing Application 153 is capable of converting addresses into 3Dimensional (3D) coordinates where Package 101 may be picked up or delivered. Also implemented in Direct Recipient Device is Direct Recipient Device Communication Module 155, which may be implemented as described in the general description of "Communication Module" above.

DSD Meta Instructions 146 and DRD Meta Instructions 156 may contain for example instructions that do not allow Direct Sender 140 and Direct Recipient 150 respectively to perform certain actions that would be inimical to another device that is part of Pick-up/Delivery System 100. As an example, Direct Sender 140 and Direct Recipient 150 should not be able to control Unmanned Vehicles being used to pick up or deliver a Package 101 until specific conditions such as distance or height relative to Direct Sender Device 141 or Direct Recipient Device 151 are met.

Figure 1C:
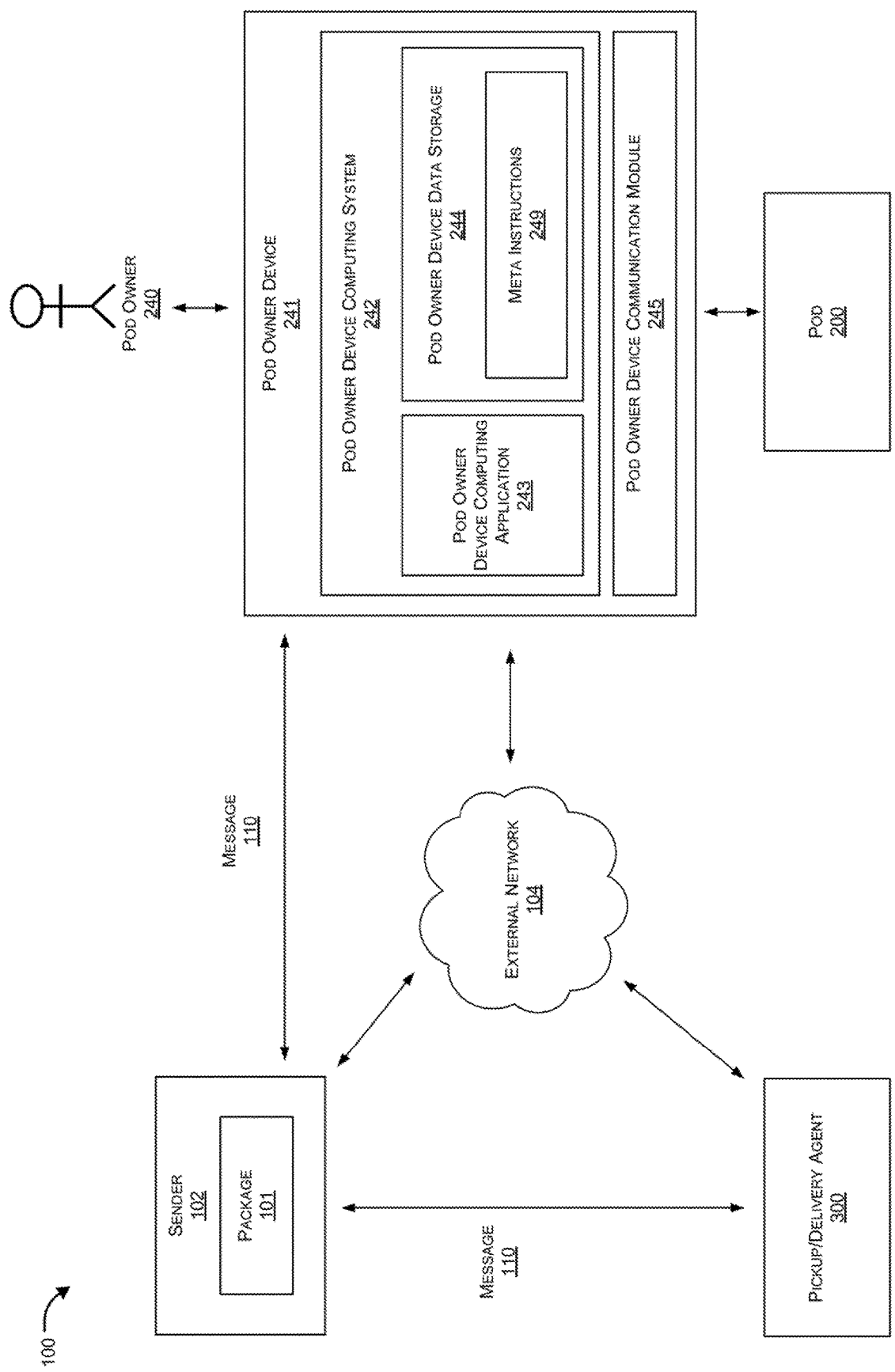
Figure 1D:
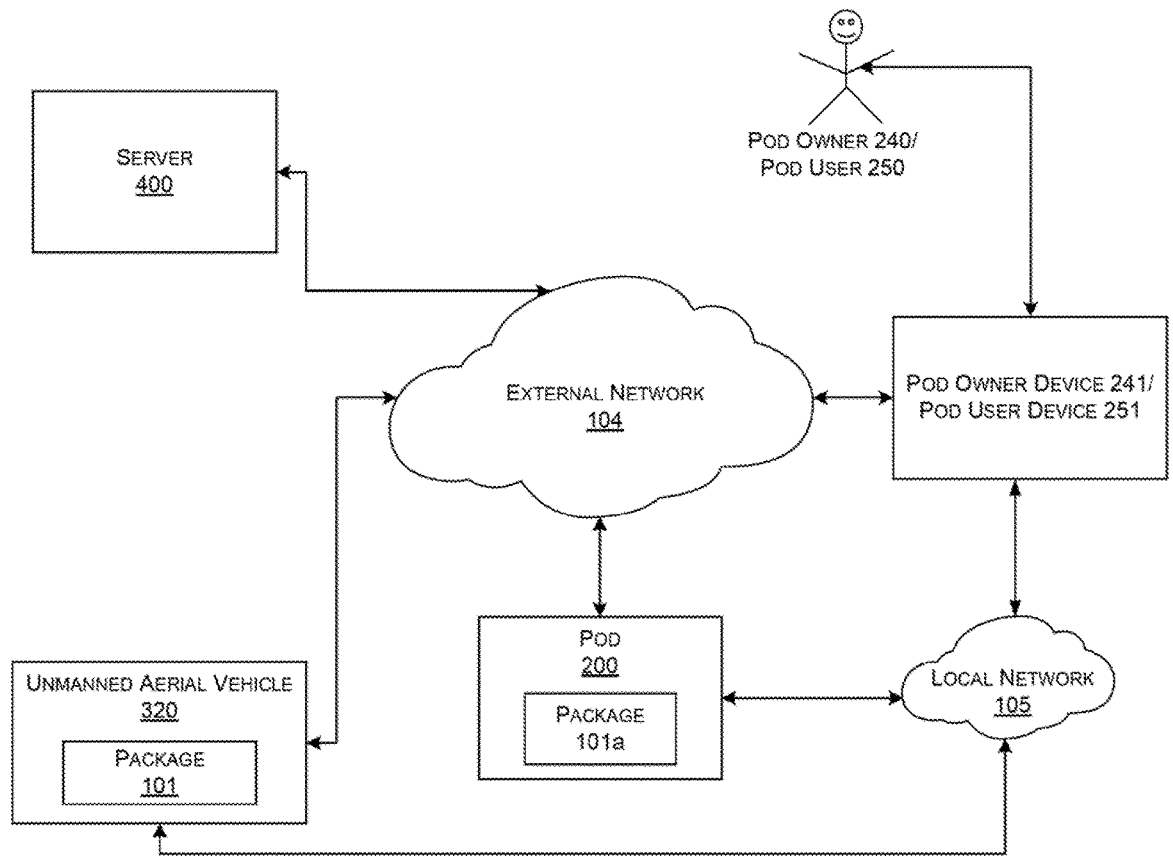
Figure 1E:
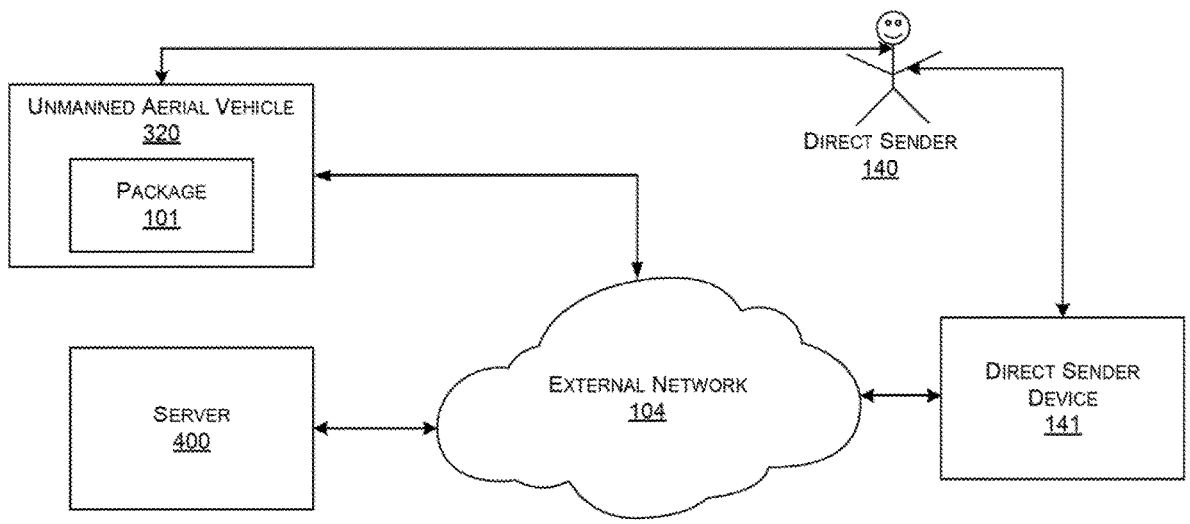
Figure 1F:
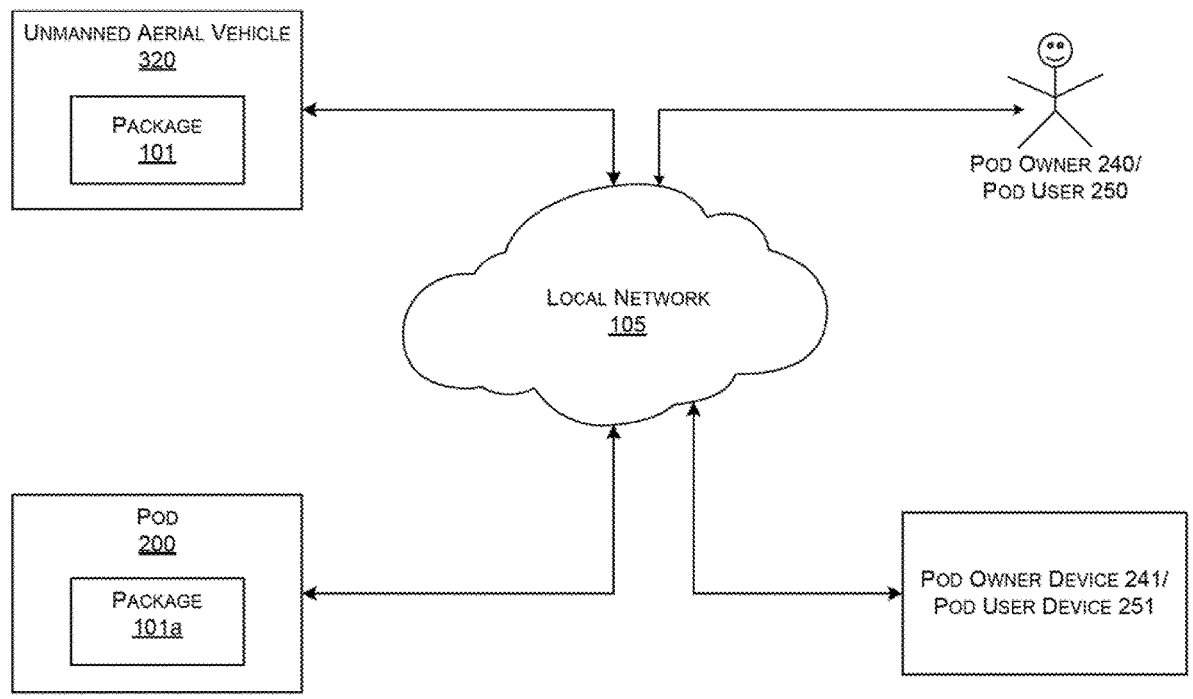

With reference to the following descriptions FIG. 1C illustrates an exemplary representation showing configuration of a Pod Owner 250 in the proposed system, wherein the Pod Owner 250 can have a similar architecture compared with that of the Recipient 103, wherein the Pod Owner 250 interacts with one or more authorized Pods 200 for enabling sending of messages/instructions/commands with, for instance, information about delivery agents so that the delivery agents can operate/lock/unlock the Pods 200 and enable Pick-up/Delivery of one or more Packages 101. FIGS. 1D to 1F further illustrate exemplary variations in the proposed system architecture, wherein in FIGS. 1D and 1E, the components of the system such as Pod 200, Server 400, UAV 320 are connected to each other through External Network 105, whereas in FIG. 1F, one or more packages such as Package 101 and Package 101a are connected through Local Network 106 with Pod Owner 250/Pod User 260 and/or with Pod Owner Device 251/Pod User Device 261.

Figure 2A:
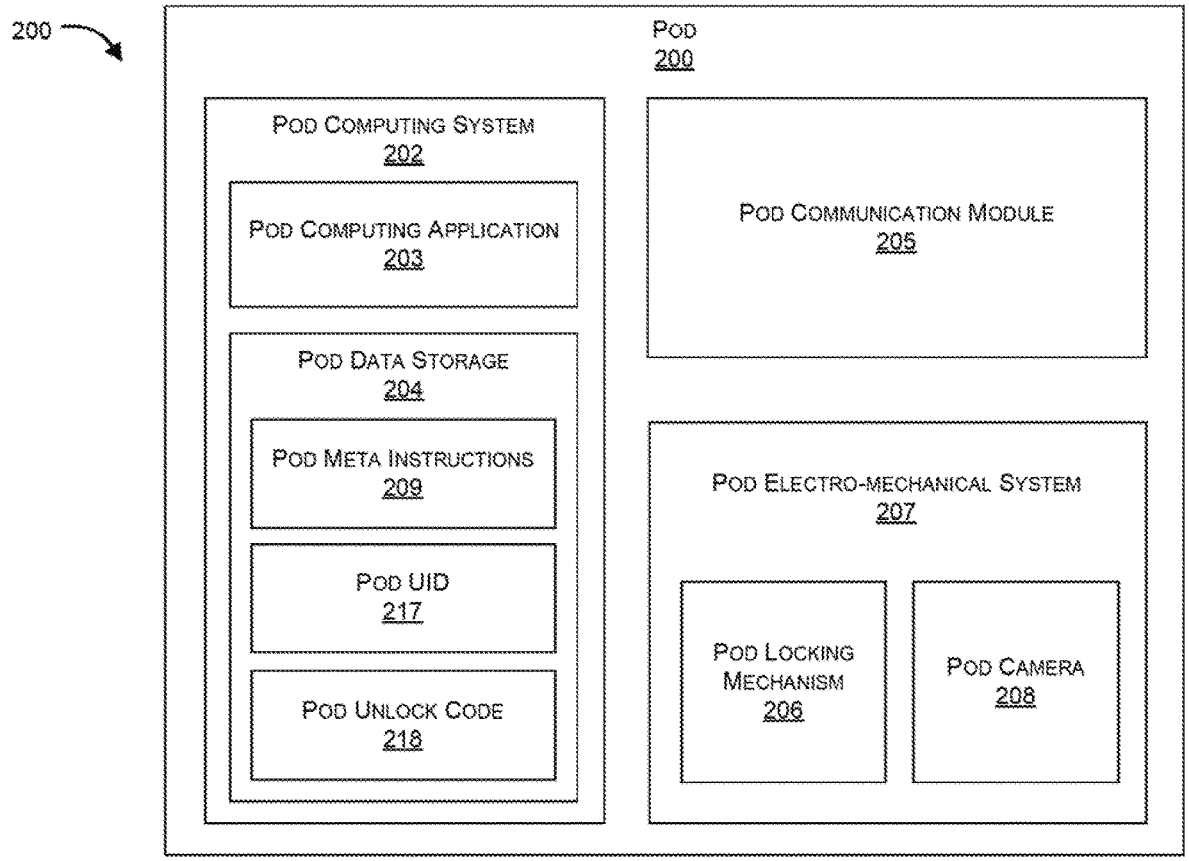
FIGS. 2A to 2E illustrate exemplary architectures of Pod, UAV, UTV, Server, and Pod User Device as exemplary devices.
Figure 2B:
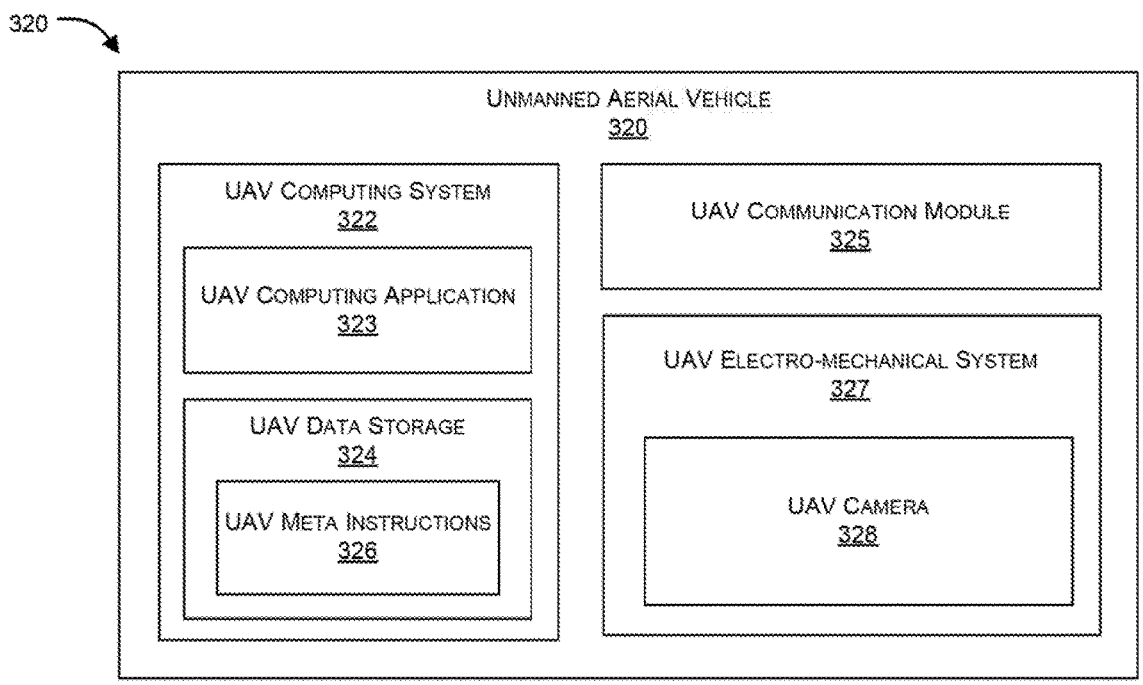
Figure 2C:
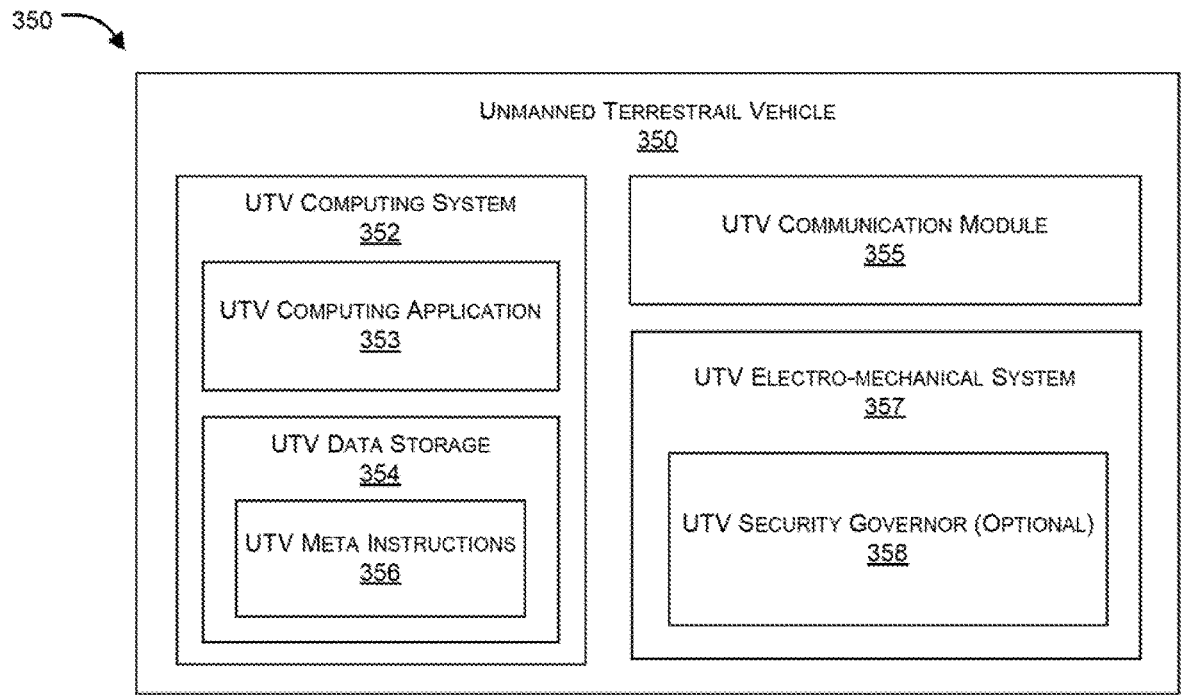
Figure 2D:
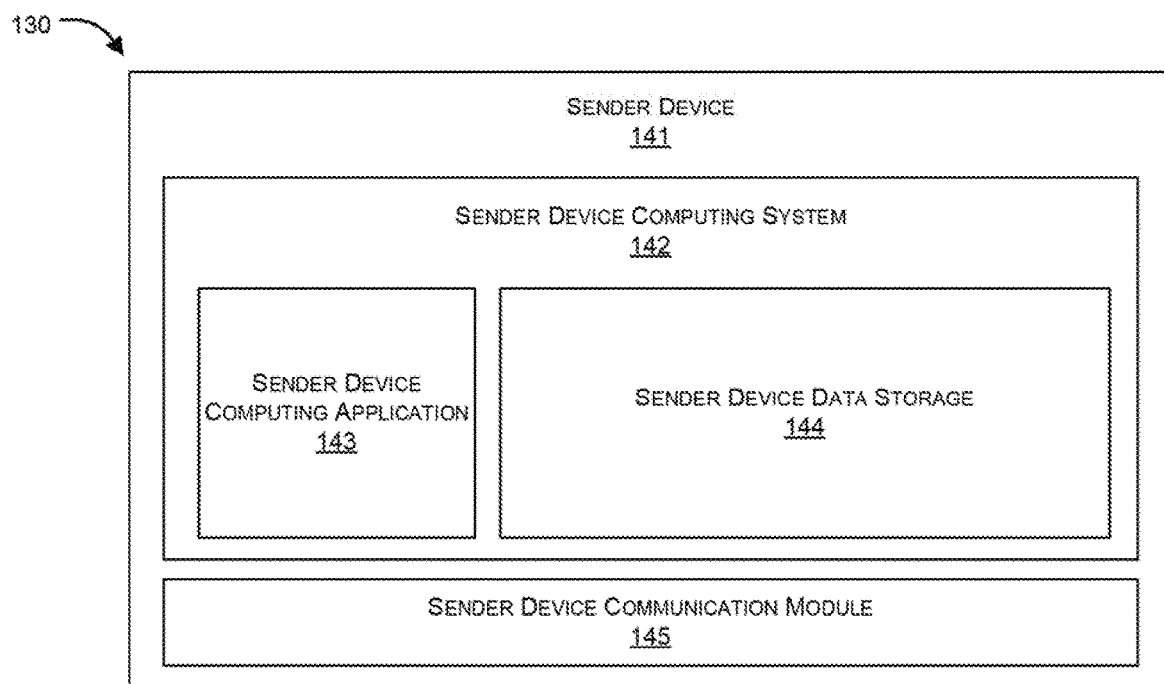

With reference to the following descriptions FIGS. 2A to 2G illustrate exemplary device construction details and/or components of other computing devices that form part of the proposed system. For instance, FIG. 2A illustrates components of Pod 200, wherein fundamental/basic functions and possible implementations of Pod Computing System 202, Pod Computing Application 203, Pod Data Storage 204, Pod Communication Module 205 are not being explained again as they are on the lines of the features/implementations described for Direct Recipient Device 151 and in the more general descriptions at the start of this disclosure. Similarly, FIG. 2B illustrates components of UAV 320 showing UAV Computing System 322, UAV Computing Application 323, UAV Data Storage 324, and UAV Communication Module 325, and FIG. 2C illustrates components of UTV 350 showing UTV Computing System 352, UN Computing Application 353, UN Data Storage 354, and UN Communication Module 355. FIG. 2D, on the other hand, illustrates components of Server 400 showing Server Computing System 402, Server Computing Application 403, Server Data Storage 404, and Server Communication Module 405. For detailed descriptions of the components above see the following disclosure which should be taken to include, where necessary, the general descriptions previously taught. In case of conflict, the specific descriptions that follow will supersede the general descriptions.

Pod

In an aspect, Pod 200 can be a structure made of a material such as Fiberglass, metal, wood or any other appropriate material and be of any reasonable size to accommodate packages that may typically be sent by Sender 102 or received by Recipient 103. A Pod 200 can be, in a single-family residence for example, outside the door, on an exterior wall, on the porch, on a balcony, or at the curb where the mailbox for a single-family home is typically located. Pod 200 can also be "built-in" as in a door covering an opening in a wall and said opening may be enclosed by surrounding walls or may be open on one side, for example in the interior or may have another door in the back accessible from the interior of a dwelling, office or any space. A Pod 200 may have a multiplicity of openings. For example, a door or drawer that opens to the front or sides makes it easy for a human to operate, whereas an Unmanned Aerial Vehicle may deliver from a second opening at the top of a Pod 200. Thus, in a first configuration, Pod 200 has one opening, but in a second configuration, Pod 200 has both aforementioned openings. A practitioner versed in the art can appreciate that size, shape, location or material of manufacture is not a limitation of the present invention and that the present invention can be applied to any structure with an opening capable of being locked and unlocked as described herein in order to present a Package 101 for pick up or receive a Package 101 for delivery. An example of a Pod 200 is shown in FIG. 3A, but again, many designs are envisioned and its shape, size and configuration as depicted is not to be taken as limiting the invention in any way. Pod 200 may be implemented with Pod Computing System 202, Pod Computing Application 203, Pod Data Storage 204 and Pod Communication Module 205 as described in the respective general descriptions taught earlier.

In an exemplary aspect, as part of setup and operation, Pod Communication Module 205 can maintain two modes, Access Point (AP) mode and Client mode, wherein, in the Access Point mode, Pod Communication Module 205 acts as a central hub to which one or more devices can connect through their communication modules. To connect, the communication modules of the other devices may be required to be configured with the SSID and password (or equivalent) of the Access Point. These devices that connect to the Pod Communication Module 205 can be referred to as clients. On the other hand, when Pod Communication Module 205 is in client mode, it connects to another device that is acting as an Access Point and such a device can be one of the elements of the Pick-up/Delivery System (such as but not limited an unmanned vehicle or user device) or it can be an accessible home/office Wi-Fi access point or even other devices or systems providing connectivity using for example GPRS.

In an aspect, Pod Communication Module 205 can have a multiplicity of configurations representing a multiplicity of embodiments as explained below. Such embodiments can be described as exemplary embodiments using Wi-Fi, but other technologies and protocols may be used as well. For example, some actions or steps may be completed using Bluetooth, NFC and so on. In one embodiment, two Wi-Fi modules can be configured as part of Pod Communication Module 205, wherein, in one Wi-Fi module, the Pod is configured as an Access Point mode and in the other Wi-Fi module, the Pod is configured as a Client. In an aspect, a single Wi-Fi module can be switched between Access Point mode and Client mode, wherein the interval between switching as well as the time that module remains in each mode can be configured in Pod Application 203 during manufacture, setup, or at intervals by authorized users such as the owner. The intervals can also be changed dynamically by Pod Application 203 depending on the operation being performed or to be performed. For example, when a delivery is not expected the default state may be Client mode with an occasional short-duration switch to AP mode; however, when a delivery is expected, communication module can be placed in Access Point (AP) mode for longer intervals as delivery nears, and may in this case switch to Client mode only occasionally in order to check for messages or for synchronization with other components of Pick up and Delivery System 100. As expected delivery time nears, the interval in AP mode is increased. Furthermore, when Wi-Fi module is in AP mode and an external device connects as a client, Wi-Fi module remains in AP mode until the connection is broken. If connection is not terminated for a certain time interval and the time interval exceeds a configured value stored in Pod Data Storage 204, Pod Computing Application 203 may send a reminder in the form of a Message 110 to connected device to terminate the connection. Alternately, Pod Computing System 202 can initiate such a message when connection is idle for a certain time interval i.e. no messages are exchanged between connected entities. In another exemplary embodiment, two independent and coexisting instances of Wi-Fi can be created by the Pod Computing Application 203 with one instance being in client mode (connects to Local Network 106) and the other instance being in AP mode and allowing connections from devices that provide the right credentials. Another implementation can also be configured in what is commonly known as Peer-to-Peer mode. Further, Pod Computing System 202 can configure Pod Communication Module 205 to use different protocols on the same physical connection, for example using TCP to communicate via an External Network 105 and using IP based communication to connect to a Local Network 106.

In an aspect, Pod Computing System 202 controls at least a Pod Locking Mechanism 206 and, also controls a Pod Electro-Mechanical System 207. For example, the Pod Computing System 202, by means of the Pod Computing Application 203 and using data stored in Pod Data Storage 204 and/or a Message 101, can lock or unlock Pod Locking Mechanism 206 of Pod 200. Further, the Pod Electro-Mechanical System 207 can, among other functions, physically open the Pod 200's door or close it when appropriate based on valid instructions from Pod Computing System 202 in a Message 110 or an algorithm based on elapsed time or local conditions. Pod Electro-Mechanical System 207 can also include heating elements, cooling elements, sensors, lights, indicators, audio devices, levers, pulleys gears and any other physical parts, fixed or moving that provide desired functionality as described in the present disclosure.

Pod 200 may also be optionally equipped with at least a Pod Camera 208. Pod Camera 208 can record single or time-lapsed images or video of the contents of the Pod 200 and thus record the state of a Package 101 or even the process of delivery of Package 101 into the Pod 200 or pick up of said Package 101 from the Pod 200. Pod Camera 208 can ordinarily be static i.e. unmoving, but may allow zooming and panning in order to enhance the video or pictures recorded and such zooming and panning may be performed via hardware (for example moving the lens back or forward, or activating swiveling mechanism) or through software using various image processing technologies (described later). Pod Camera 208 can be a fixed camera that points to the interior of Pod 200. Pod Camera 208 can also be a swiveling camera which swivels toward the interior or exterior as needed in order to record the process of Pick up and Delivery. In an aspect, the present invention teaches an arm made of string, rubber, or any other flexible material that is anchored at one end to the Pod 200 and at the other end to the Pod Camera 208. When the door or drawer of a Pod 200 is opened, the camera is swiveled. Two exemplary positions and mechanisms to swivel the camera are disclosed, but a practitioner of the art will appreciate that many other similar mechanisms are possible and the present illustrations should not be seen to be limiting in any way. In some cases, a Pod 200 may be equipped with multiple cameras and each may be operated separately or in tandem by Pod Computing Application 203. In one embodiment, one Pod Camera 208 may be implemented to acquire images of the interior of the Pod 200 while another Pod Camera 208a may be implemented to acquire exterior images.

Pod Data Storage 204 may include an image of the surface where packages are received (as an example, the bottom of the drawer of Pod 200, or the entire interior of Pod 200) and this may be saved at the time of manufacture or at any time by an authorized user such as an owner of Pod 200, as a reference image. For example, Pod Computing Application 203 may include a feature to trigger Pod Camera 208 to take a picture of said surface at intervals when Pod 200 is empty. Further, the image can be manually updated by an authorized device in Pick-up/Delivery System 100 again by triggering Pod Camera 208. This stores the latest picture (including changes such as fading and scratches) and can serve as a reference image for various purposes as described next as well as for Local Precision Positioning System described later. Pod Computing Application 203 uses Pod Camera 208 to take pictures at predetermined intervals or coinciding with events such as a Pick up or a Delivery and to do this Pod Camera 208 may be activated to acquire images whenever Pod Locking Mechanism 206 is operated. Pod Computing System 202 can compare the latter images with the original i.e. reference images and if different (using an image comparison algorithm described later) can report that a Package 101 is present in Pod 200 or Pod 200 is otherwise unavailable to receive Package 101. Pod Camera 208 recording images while a Package 101 is being placed into Pod 200 or retrieved from Pod 200 can also serve as proof of delivery and retrieval by recipient respectively.

In another aspect, Pod Computing System 202 controls and exchanges data and instructions from other components of the Pod 200 including at least a Locking Mechanism 206, at least a Pod Electro-Mechanical System 207, and at least a Pod Camera 208. Pod Data Storage 204 can store the aforesaid data in at least a local storage namely Pod Data Storage 204 and at least a portion of it in external data storage using backup, replication, virtualization or any other technique not repugnant to the context. Pod Data Storage 204 may also contain certain algorithms and keys used to encrypt and decrypt data sent to other devices or received from other devices. Further, Pod Computing Application 203 is capable to generate encryption/decryption keys as needed to be used with encryption/decryption algorithms. In an exemplary embodiment, Pod 200 is operative with a Locking Mechanism 206 similar to existing locks used on doors, drawers and the like, but which can be opened electronically using any protocol, but may also be implemented with a manual override (for example with a key, a master key or deconstructive process). For example, an electronic relay, in conjunction with other electronics can pull or push a deadbolt or turn the chambers of a lock. Many types of locks are commercially available and may be used in various configurations and the present invention is not constrained by or limited to any type of lock, whether known today or conceivably invented in the future. It is to be appreciated that the operation of unlocking a Pod may need to be followed by opening a door, a drawer or similar element and conversely, the step of locking Pod 200 may need to be preceded by closing a door, a drawer or similar element. In some configurations, springs, hydraulic openers and such devices may be used which automatically open or close a door, drawer or lid. Such locking, unlocking, opening and closing operations may also be accomplished by sending one or more Message 110 to Pod 200 and such Message 110 may, in some cases, work in conjunction with other actions such as a manual press of a button.

Pod Electro-Mechanical System 207 may include hardware such as gears, levers, pulleys, slides, electronic chips, electronic boards, relays, conveyor belts, turntables, cooling sub-systems, heating subsystems (for example heating coils or infrared radiators) and a variety of other mechanical and electrical/electronic devices without limitation that can reasonably be accommodated by Pod 200. Pod Electro-Mechanical System 207 may also include one or more sensors to measure temperature, humidity and any other environmental factors that may be measured. Additionally, Pod Electro-Mechanical System 207 may include sensors, proximity sensors or interruptible beams to determine properties of Package 101 such as, its weight, physical dimensions, temperature (of Package 101), as well as chemical sensors to detect for example dangerous goods (explosives), leakages or spoilage of foods, even the presence/absence of foods or other materials and so on. Sensors can even use these to determine whether a Package 101 is present in Pod 200. Sensors are linked to other components of the Pod Electro-Mechanical System 207 either directly, or through and under the control of Pod Computing System 202. Pod Electro-Mechanical System 207 may also include, for example, components of drawers, doors (sliding or pivoted/hinged) and the like that be opened manually or automatically by other components of Pod Electro-Mechanical System 207 such as springs, motors and any other devices that are used to open or close doors, drawers and similar components without intervention by a human.

With reference to FIG. 3A, Pod 200 may optionally include a Pod User Interface 210 that may include one or more input or output devices such as but not limited to a keypad, keyboard, mouse, or touchpad, an electronic or mechanical keypad with a display such as an LCD screen, an LED screen, indicator lights or any other electronic or mechanical display. Pod User Interface 210 may also include static data such as text and images (for example to provide instructions). The input and display and other components need not be proximally located on Pod 200 and may not even be located on Pod 200, but may be installed for example on a wall or other environmental feature in order to display or provide access more easily for users. The Pod User Interface 210 may also comprise in whole or in part, a touchscreen (such as an LED or LCD touchscreen) so that no mechanical input device is required and instead virtual buttons and keys can perform the equivalent function. Pod User Interface 210 may thus be entirely or partially virtual. Pod User Interface 210 may be used to enter codes, passwords or commands to operate Pod 200 or any of its components. Said interface may also include one or more buttons on the Pod that may or may not be proximally located in relation to each other or the above-named components of Pod User Interface 210. For example, a button may be used to guarantee that a person locking/unlocking or otherwise opening Pod 200 is proximal to the Pod. Requiring the physical pressing of such a button ensures that Pod 200 is not unlocked remotely for example when this is not desirable. Further, said button may also be used to turn on electrical power to the Pod 200, said power having been turned off automatically by Pod Computing System 202 after a period of time in order to conserve electricity or to extend battery life. The various electronic, mechanical and static components of Pod User Interface 210 work together to receive inputs and provide messages.

Every Pod 200 has a Unique ID now called Pod UID 211 that establishes its identity. Pod UID 211 is any combination of alphanumeric characters and/or symbols can be, for example, at least one of, or a combination of a phone number and a machine ID (such as SSID or Bluetooth Address or MAC address) of Pod 200 or one of its components. Pod UID 211 is typically represented by Pod Graphic 212 and may be printed, engraved, displayed on an LED or LCD screen, via a sequence of static or blinking lights, or otherwise displayed on Pod 200, in a multiplicity of locations and in a multiplicity of ways including any combination of a plurality of alphanumeric characters, a symbol, a plurality of symbols, a bar code, a QR Code, an image, a hologram or any other form of representation available now or in the future and can be read by scanning with a camera, QR Code Reader, Bar Code Reader or any appropriate device, any combination of such devices, or any device that simulates such devices or performs substantially in the same manner as such devices. Pod UID 211, or its representation (graphic, numeric or any other form of representation) can also be stored in Pod Data Storage 204 and may additionally be stored as required by various embodiments in a plurality of servers, devices operated by users and owners of pods and delivery agents amongst others. Pod UID 211 may preferably be used for example as the ID of a Local Network 106 (such as a Wi-Fi SSID or Bluetooth Address or both), so as to make it easy to exchange messages between Pod 200 and external devices such as those mentioned above which connect to Pod 200 is order to, for example unlock or operate Pod 200. Pod UID 211 is transmitted under some circumstances to other devices in Pick-up/Delivery System 100. Pod UID 211 may also be broadcast by Pod 200 so it can be used as beacon or for identification by other entities in Pick-up/Delivery System 100 or optionally even entities outside of said system. Pod UID 211 allows any entity in Pick-up/Delivery System 100 to recognize Pod 200 and, using Pod Graphic 212, to also to recognize its position relative to Pod 200 (see Local Precision Positioning System in the Embodiments for more details). This helps ensure that a delivery is made to the right Pod 200.

In some cases, Pod UID 211 may also be set to "None" or "null" or equivalent value (in case no Pod 200 exists at the Recipient's location or delivery to a Pod 200 is not desired) in the data storage of a device or server, when delivery is not to a Pod 200, but is manually retrieved by Recipient 103. By setting Pod UID 211 to a null or equivalent value other entities are able to deduce that a Pod 200 is not present or not functional and appropriate alternative processes chosen for functions such as delivery of Package 101.

Pod 200 may have one or more combinations of images or text on the outer surfaces as well as internal surfaces. This combination, now called Pod Graphic 212 can include an appropriate image, barcode, QR code or other graphic or even alphanumeric characters and may be comprised, in whole or in part of Pod UID 211 of the Pod. In the discussion, any of the above forms either individually or as a group may constitute Pod Graphic 212 and the context of the description will clarify the specific graphic being described.

Pod Passcode can be a unique code used to lock/unlock Pod 200 or perform other operations that Pod 200 is capable of. For example, Pod Passcode 213 (as shown in FIG. 2A) may consist of a sequence of characters which when entered a series of steps or in an interface unlocks Pod 200. To accomplish this task Pod Passcode 213 may be received by Pod Communication Module 205, and then processed by Pod Computing Application 203. The process is more fully described in the embodiments later in the present disclosure. Pod Passcode 213 may be stored in Pod Data Storage 204 or stored in other devices, and may in fact be generated on a different device or a server that is part of Pick-up/Delivery System 100. Pod Passcode 213 may be transmitted to other devices and may simultaneously be stored on multiple devices. Pod Passcode 213 may be set at the time the manufacture or initial setup for use, but may also be changed at intervals by an authorized entity such as owner of Pod 200. A unique Pod Passcode 213 may also be generated or regenerated for each operation or group of operations. Furthermore, unique Pod Passcode 213 may be generated or regenerated at certain fixed or random time intervals.

In an aspect Pod 200 may include a Pod Payment Slot 214 (as shown in FIG. 3A) which can perform certain operations similar to an Automatic Teller Machine (ATM). For example, Pod Payment Slot 214 may be capable to dispense cash when required as a part of a "Cash-On-Delivery" transaction or even for a Pick up. Pod Payment Slot 214 can also dispense cash unrelated to a Delivery or Pick up. Further, Pod Payment Slot 214 can be configured to accept cash and count said cash as some vending machines are enabled to do. Pod Payment Slot 214 can also incorporate a card reader which is capable of reading credit, debit and various other types of cards to enable various types of transactions. Pod Payment Slot 214 may be operatively coupled with Pod User Interface 210 for input of passwords, codes, amounts and the like.

In an embodiment, Pod 200 includes one or more receptacles now called Pod Receptacle 220 (as shown in FIG. 2-A). Pod 200 in some cases does not include a separate Pod Receptacle 220, but Pod 200 may itself entirely comprise the Pod Receptacle 220. Pod Receptacle 220 may optionally be enabled with Pod Receptacle Computing System 222 which is further enabled with Pod Receptacle Computing Application 223, Pod Receptacle Data Storage 224 and Pod Receptacle Communication Module 225, each of which have been described under a respective general description earlier. The said components of Pod Receptacle 220 may work in conjunction with and may be operatively coupled with the corresponding module of the Pod 200 in which said Pod Receptacle 220 is housed. For example, Pod Receptacle Communication Module 225 and Pod Communication Module 205 may be operatively coupled so that they can communicate using one or more communication protocols. Pod Receptacle 220 may be completely or partially enclosed and can take the form of a static receptacle with, for example, a door (sliding or pivoted/hinged), or it can take the form of a drawer that slides in and out of Pod 200. Pod 200 can further include a multiplicity of Pod Receptacles 220, each of different shapes sizes, materials and having different components and different functions and in this case, they are referred to as Pod Receptacle 220, Pod Receptacle 220a-Pod Receptacle 220n. Further, each Pod Receptacle 220 may be enabled with the above described features, correspondingly numbered such as Pod Receptacle Computing System 222, Pod Receptacle Computing System 222, Pod Receptacle Computing System 222. Many such forms and a variety of designs for such a Pod 200 and corresponding Pod Receptacles 220 are envisioned and their design described or illustrated herein, or others not described or illustrated due to their obviousness, should not be perceived as limiting in this invention.

In an exemplary aspect, each Pod Receptacle 220 can be detachable so it can be removed as a single unit and either operated or shipped with its contents. Pod Receptacle Electro-Mechanical System 227 may be enabled with an electromechanical relay, motor or the like, which may control at least one of a lock, clip and any other such mechanism that attaches Pod Receptacle 220 to the Pod 200. Said mechanism, when triggered by Pod Computing System 202 or by Pod Receptacle Computing System 222, unlocks, detaches or unclips and allows Pod Receptacle 220 to be detached from Pod 200. When Pod Receptacle 220 is detached from Pod 200, it can be treated as a Pod 200 with all its constituent parts and functionality. In this case, for example Pod Receptacle Computing System 222 becomes Pod Computing System 202, Pod Receptacle Computing Application 223 become Pod Computing Application 203 and so on. In some cases, Pod Receptacle 220 may need to be further enabled with components so it can perform necessary functions of Pod Computing System 202, Pod Computing Application 203 and so on, or it may need to be upgraded, downgraded or configured to be a fully functional Pod 200. As taught above, Pod Receptacle 220 can also be shipped as a unit, for example when it has the form of a closed box. In this case Pod Receptacle 220 can be treated as Package 101. In this case, for example Pod Receptacle Computing System 222 becomes Package Information Device Computing System 122, Pod Receptacle Computing Application 223 become Package Computing Application 223 and so on. In some cases, Pod Receptacle 220 may need to be further enabled with components so it can perform necessary functions of Pod Computing System 202, Pod Computing Application 203 and so on, or it may need to be upgraded, downgraded or configured to be a fully functional Pod 200. Thus, a Pod Receptacle 220 may conceivably be converted to Pod 200 or Package 101, and in some cases Pod Receptacle 220 may already have all the parts and configuration required in order to function as either Pod 200 or Package 101. Pod Receptacle 220 may be further modified or may have built-in other features that allow it to be converted into other devices in the Pick-up/Delivery System 100 (such as a vehicle) as described later in this disclosure. Pod 200 maintains a list of Pod Receptacle 220 contained within it and also their status—for example, whether they are attached to or detached from the PodBank 230.

PodBank

Figure 3B:
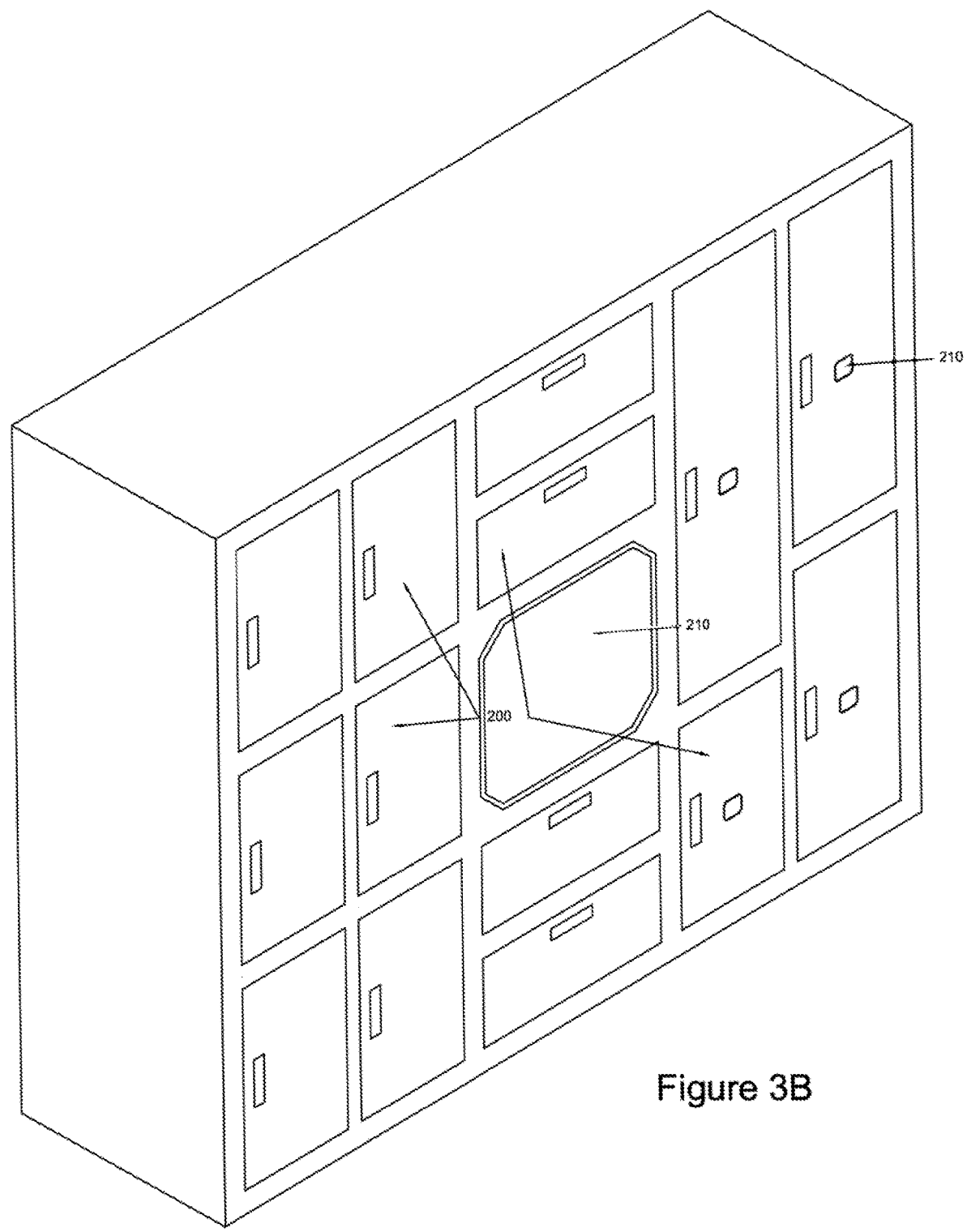
FIG. 3B shows an exemplary view of a PodBank with Sub-Pods

In another aspect, a multiplicity of Pods can be can be combined into a bank of Pods now called PodBank 230 as depicted in FIG. 3B. Each said Pod that is part of PodBank 230 is now called Sub-Pod 240. PodBank 230 is typically situated in the lobby of a multi-tenant building, a street corner, a railway station or any other public or semi-public location, but may, in some uses be in a Private location. PodBank Computing System 232 can include a Pod Bank Computing Application 233 and a PodBank Data Storage 234; PodBank Computing System 232 is operationally coupled to a PodBank Communication Module 235. These components are more generally described earlier and hence the description is not being repeated here in the interests of brevity. PodBank 230 may include a PodBank User Interface 239, which interacts with PodBank Computing System 232, but in this case, PodBank Computing System 232 may be capable to control a multiplicity of Sub-Pods 240 and therefore PodBank User Interface 239 may be used to operate any Sub-Pod 240 when required. PodBank User Interface 239 may include an electronic or mechanical keypad with a display such as an LCD screen, an LED screen, indicator lights or any other electronic or mechanical display. PodBank User Interface 239 may also include static data such as text and images (for example to provide instructions). PodBank User Interface 239 may include one or more input devices such as but not limited to a keypad, keyboard, mouse, or touchpad. Pod User Interface 210 may also comprise in whole or in part, an LED or LCD touchscreen so that no mechanical input device is required virtual buttons and keys can perform the equivalent function. PodBank User Interface 239 may thus be entirely or partially virtual. PodBank User Interface 239 may be used to enter codes, passwords or commands to operate Sub-Pod 240 or any of its components. The input and display and other components need not be located on PodBank 230 and may not even be proximally located, but may be installed for example on a wall or other environmental feature in order to display or provide access more easily for users. PodBank User Interface 239 may also include of one or more buttons on the PodBank 230 that may or may not be proximally located in relation to each other or the above-named components of PodBank User Interface 239. For example, a button may be used to guarantee that a person locking/unlocking or otherwise opening Sub-Pod 240 is proximal to said Sub-Pod 240 or at least PodBank 230. Requiring the physical pressing of such a button ensures that Pod 200 is not unlocked remotely for example when this is not desirable. The various electronic, mechanical and static components of PodBank User Interface 239 work together to receive inputs from and provide messages.

Sub-Pod 240 as identified above may optionally include one more receptacles, such a receptacle being structurally and functionally the same as a Pod Receptacle 220 (FIG. 2A) in Pod 200 and hence in this description, receptacles in Pod 200 and Sub-Pod 240 are to be considered the same. However, there may be minor differences in receptacles that are in Pod 200 and those in Sub-Pod 240 depending on the design of each, just as there may be minor differences between receptacles in a Pod 200 of a particular design and another Pod 200a of a different design. Any limitation of Pod Receptacle 220 in any configuration of a Sub-Pod 240 or a Pod 200 should not be taken to limit the present invention. Instead, differences or limitations in one aspect should be taken to be variations in design of the same element. Sub-Pod 240 may include several additional components as Pod 200 specifically at least a Sub-Pod Locking Mechanism 241, and optionally at least one of a Sub-Pod Electro-Mechanical System 242 and a Sub-Pod Camera 243. In an aspect, each Sub-Pod 240 may not necessarily have its own Computing System, Computing Application, Data Storage or Communication Module, although it can conceivably be envisioned that some or all of these elements may be present. When present, these modules will be referred to by the same names as those of Pod 200. Thus, Sub-Pod 240 may conceivably include one or more of a Pod Computing System 202, Pod Computing Application 203, Pod Data Storage 204 and a Pod Communication Module 205. The functionality enabled by these modules, if present, may conceivably be shared between a Computing System enabled in Sub-Pod 240 and the PodBank Computing System 232 and when not present, entirely by corresponding modules of PodBank such as PodBank Computing System 232, PodBank Computing Application 233, PodBank Data Storage 234 and PodBank Communication Module 235. In an exemplary embodiment, Sub-Pod Locking Mechanism 241 may be operable by PodBank Computing System 232. PodBank 230 maintains a list of Sub-Pods 240 contained within it and also their status—for example, whether they are locked/unlocked and whether or not they contain a Package 101.

Each Sub-Pod 240 may be enabled with a Sub-Pod Graphic 247 and a Sub-Pod UID 248 and these are functionally the same as, and have the same purpose as Pod Graphic 212 and Pod UID 211 respectively and hence will not be described again here. Sub-Pod 240 may also have associated with it, Sub-Pod Unlock Code 245, Sub-Pod Detach Code 246, either or both useful for controlling access to Sub-Pod 240 including the ability to access the detaching mechanisms. Sub-Pod Unlock Code 245 and Sub-Pod Detach Code 246 may be generated or regenerated for each operation or group of operations. Sub-Pod Unlock Code 245 is functionally similar to Pod Passcode 213.

Pod Owner and Pod User

In an exemplary aspect, with respect to FIG. 1C, Recipient 103 who owns a Pod 200 can be referred to as Pod Owner 250, wherein Pod 200 can have multiple owners namely Pod Owner 250, Pod Owner 250a, Pod Owner 250b, and so on with the same rights or variable rights to operate Pod 200 and this is described in greater detail under Embodiments. Pod Owner 250 may not need to be the Recipient and can be an independent entity/person who controls and/or owns Pod 200. Pod Owner 250 can own multiple Pods 200 and these may be contiguous (for example as a monolithic bank, previously described as PodBank 230) or non-contiguous i.e. geographically dispersed. A Pod Owner 250 may use a Pod Owner Device 251 (previously and generally described as "Device" in the description above) to interact with various parts of the Pick up and Delivery System 100, for example to operate a Pod 200, to schedule Delivery or Pick up of a Package 101 or to send messages to and receive messages from a Pick-up/Delivery Agent 300. The Pod Owner Device 251 may be enabled with a Pod Owner Device Computing System 252 (previously and generally described as "Computing System" in the description above). Pod Owner Device Computing System 252 can be configured to run one or more software applications, now termed Pod Owner Device Computing Application 253 (previously and generally described as "Computing Application" in the description above) and can also enable, through its data storage ability, Pod Owner Device Data Storage 254 (previously and generally described as "Data Storage" in the description above) where information is stored in the form of files, databases and so on. Pod Owner 250 may operate more than one Pod Owner Device 251. For example, Pod Owner Device Application 253 may be installed in whole or in part on a Smartphone as well as a computer (Laptop or Desktop) owned by Pod Owner 250 and therefore both function as Pod Owner Device 251. In a related group of interactions, some interactions by Pod Owner 250 may be performed on one device (for example, entering ownership information or address of Pod 200 or scheduling delivery of an online purchase) and other interactions may be performed on a second device (for example, using a smartphone to unlock Pod 200 to retrieve a Package 101 that was delivered to said Pod 200 as a result of said online purchase).

Pod Owner 250 may create additional owners i.e. Pod Owner 250a, Pod Owner 250b and so on. For example, Pod Owner 250 may enable a family member as additional Pod Owner 250a and the latter will have all the rights and functionality of Pod Owner 250 including the ability to add, remove and edit other Pod Owners 250a and so on. In such a case, the first Pod Owner 250 can make her account non-destructible, by configuring Pod 200 or in such a manner that Pod Owner 250 can never be removed by any other Pod Owner 250a.

In another example, Pod Owner 250 may allow a neighbor to operate her Pod 200 so that the neighbor can accept deliveries or allow pick up of a Package 101. If Pod Owner 250 does not allow such a new user/operator to add other users, but does grant the right to operate Pod 200, such a user/operator is now designated as Pod User 260. Thus, Pod User 260 does have not all the rights that Pod Owner 250 or even Pod Owner 250a have, but does have certain usage rights. These rights may include for example the ability to lock/unlock Pod 200, schedule/accept deliveries to Pod 200, and so on.

In an aspect, a Pod User 260 such as a Recipient of a package may have all the rights and functionality of Pod Owner 250, but the rights of Pod User 260 will never exceed those of Pod Owner 250. A Pod Owner 250 can also be a company that owns several Pods 200 or a PodBank 230 and rents an individual Pod 200 or Sub-Pod 240 to a Pod User 260 or even to Pod Owner 250a.

In an aspect, a Pod User can use a Pod User Device 261 to interact with various parts of the Pick up and Delivery System 100, for example to operate a Pod 200, to schedule delivery or pick up of a Package 101, or to send messages to and receive messages related to picking up or delivering a Package 101. Pod User Device 261 and its components correspond to "Device" and associated components as described earlier in this description, and hence are not being explained to maintain brevity in the instant description. However, in brief, Pod User Device 261 can comprise Pod User Device Computing System 262, which in turn comprises Pod User Device Computing Application 263 and Pod User Device Data Storage 264 operationally coupled to Pod User Device Communication Module 265 all operating in a manner reflective of the operations of the generally described components above.

Pod Owner 250 and Pod User 260 have certain rights as taught above. For example, it has been taught above that Pod Owner 250 can create, delete and edit one or more Pod Owners 250a, 250b and so on. Further, Pod Owner 250 or the created Pod Owners (for example Pod Owner 250a) may further create, delete or edit one or more Pod User 260. These owners and users singly or collectively may or may not have certain rights (such as the ability to create other entities, or to receive one or more Package 101) and a particular combination of these rights define a Usage Role 270 and the rights associated with each are collectively referred to as Usage Rights 271. A Usage Role 270 is a particular combination of rights, and Usage Rights 271 when transmitted with a Usage Role 270 may be in addition to (or subtractive from) said Usage Role 270. Thus, Usage Role 270 may fully define a set of desired rights, and Usage Rights 271 need not be specified in such a case; however, specifying Usage Rights 271 in addition (or as subtractive from Usage Role 270) grant a greater degree of granularity to requests.

When the Usage Role 270 and/or its associated Usage Rights 271 are limited to a period of time (for example a rental period in which a Pod User 260 can receive one or more Package 101 to a specific Pod 200) that period of time is referred to as Usage Period 272. Usage Period 272 may be a single period or a multiplicity of contiguous or non-contiguous periods. More details on the workings of Usage Role 270, Usage Rights 271 and Usage Period 272 are taught in the embodiments below. Pick-up/Delivery Agent 300 and its various aspects such as UAV 320 (while delivering a package) may also have rights and may be limited by their roles or by the time period. Thus, Usage Role 270, Usage Rights 271 and Usage Period 272 can be applied to devices as well as users and no limitation is to be understood unless repugnant to the context.

Pick-Up/Delivery Agent 300

In an exemplary implementation, Pod 200 enables pick ups and deliveries that are performed by a class of entities jointly and severally known as Pick-up/Delivery Agent 300. Agents can include a combination of one or more humans, vehicles, (both manned and unmanned) with or without human operators of these vehicles. Therefore, when no distinction is to be made between different types of agents we use the general term Pick-up/Delivery Agent 300.

In an aspect, a Pick-up/Delivery Agent 300 can include any combination of one or more of a Human Agent, and an Unmanned Vehicle such as an Unmanned Aerial Vehicle 320 or an Unmanned Terrestrial Vehicle 350, including amphibious vehicles, and a Manned Vehicle 380 such as a delivery truck commonly used today, optionally enabled with devices and/or computing systems to interact with other components of a Pick-up/Delivery Agent 300. It is to be appreciated that Unmanned refers to all types of vehicles that do not have a crew in the vehicle, even when partially or completely remotely controlled by a human crew whether said remote control is always used, sometimes used or never used. Thus, reference to an Unmanned Vehicle in the context of this invention includes autonomous, partially autonomous and piloted vehicles. Piloted vehicles that are called Unmanned can be piloted by a proximal operator or a Remote Operator 375. The description of Unmanned Vehicle also extends for example, to a Vehicle that has passengers none of whom are piloting the vehicle. It should also be noted that in this description, Unmanned Vehicle and Manned Vehicle can each be any kind of vehicle, including vehicles with wheels or other means of locomotion and various means of propulsion including rotors, motors (running on any kind of fuel including solar, fossil fuels and the like) or any other appropriate vehicle using any form of locomotion or propulsion or even combinations of various types of locomotion or propulsion.

In some cases, a Pick-up/Delivery Agent 300 may be capable and used in a variety of modes of locomotion. For example, a vehicle may be able to fly as well as move on the ground i.e. it has respectively Aerial as well as Terrestrial modes of locomotion. However, it may be referred to as an Aerial Vehicle if its primary mode of locomotion for that operation or for the most relevant operation (as an example delivering the package) is performed as an Aerial Vehicle.

In the process of pick up or delivery, a Pick-up/Delivery Agent 300 may need to connect to Pod 200 (through Pod Communication Module 205) for example, or to any other component of Pick up and Delivery System 100. To do so, one of more of an identifier such as an SSID for Wi-Fi or Bluetooth, a Password to connect to the specific SSID or other identifier, a protocol or a multiplicity of protocols, and a security level flag may be required. These, in combination, can be referred to as Pick-up/Delivery Connection Information 301.

In an exemplary implementation, Sender 102 directly or indirectly (for example through a server) may provide Pick-up/Delivery Agent 300 with information about the Pick up or Delivery, including, but not limited to any of a payment due (now called Pick-up/Delivery Payment 302), Pick up Information 305, Delivery Address 306, Delivery Information 307, Package and Shipping Information 130, Pod UID 211 (of a Pod 200 to which a Package 101 is being delivered), and a Pod Passcode 213. Pick up Address 304/Delivery Address 306 may be a simple street address such as is found on a shipping label. Pick up Information 305/Delivery Information 307 can be any combination of one or more of 3Dimensional coordinates (including GPS coordinates) of the address for pick up or delivery, instructions to find the address, including one or more recommended 2-dimensional or 3-dimensional arc-directions of approach (i.e. representing a multiplicity of vectors instead of a single vector), and whether Pick-up/Delivery respectively involves a Pod 200. In fact, any information including user generated instructions may be included in Pick up Information 305 and Delivery Information 307. Further, both Pick up Information 305 and Delivery Information 307 may not all of the information but may include a means to retrieve said information (such as a URL where all or part of said information is stored). Pick-up/Delivery Connection Information 301 comprises information required for various devices to communicate with each other during a Pick up or a Delivery and may include for example a Protocol (HTTP, FTP, etc.), a Technology (Wi-Fi, Bluetooth etc.), a Network ID (such as an SSID), and a Password (to connect to above Network ID).

Furthermore, in the instant system Pick-up/Delivery Agent 300 is provided with one or more arrival direction "arcs" that can be Three-Dimensional.

In an aspect, Pick-up/Delivery Agent 300 can include a person, now called Human Agent 310 performing either a Pick up or a Delivery operation on Package 101. Human Agent 310 may, for example, be a delivery person employed by a logistics company or by a common carrier or may even be Sender 102 or a person employed by Sender 102 to deliver a Package 101. Human Agent 310 may be equipped with a device now called Human Agent Device 311 (similar to "Device" as generally described above) which is further enabled with a Human Agent Device Computing System 312, (similar to "Computing System" as generally described above), and hence not explained here in detail. Human Agent Device Computing System 312 includes Human Agent Device Computing Application 313 which is in turn operatively coupled with Human Agent Device Data Storage 314 (similar to "Data Storage" as generally described above) and Human Agent Device Communication Module 315 (similar to "Communication Module" as generally described above). Human Agent may use a Smartphone as Human Agent Device 311, which may even be a personal Smartphone normally used for other tasks. If Human Agent 300 is an employee of a logistics company Human Agent Device 311 may be a dedicated device.

In an aspect, the present disclosure relates to a Package 101 delivered to a Pod 200 or picked up from a Pod 200, using for example an Unmanned Aerial Vehicle, said Vehicle now called Unmanned Aerial Vehicle 320 and being capable of loading, unloading and carrying a Package 101. In an aspect, an Unmanned Aerial Vehicle 320 (UAV 320) has at least a UAV Computing System 322 (including UAV Computing Application 323 and UAV Data Storage 324 operatively coupled to UAV Communication Module 325). Sensors built-in to UAV Communication Module 325 can sense any combination of GPS, Bluetooth, Wi-Fi, Infrared and any other appropriate technology or protocol. Components and construction of the computing System 322 may be similar to that of respective elements described more generally above and hence not being explained again for brevity of present disclosure.

In an aspect, UAV 320 also includes a UAV Mechanical System 327 which can include its propulsion engine, motors, gears and any other physical parts, fixed or moving, of the Unmanned Aerial Vehicle 320 which facilitate and control its movement. UAV Mechanical System 327 can be controlled by UAV Computing System 322 through the UAV Communication Module 325 or via a direct connection to, for example, relays, motors and the like. Commands to control the UAV Mechanical System 327 can originate from a remote user or remote system, from a proximal user, from the UAV Computing System 322. Commands from other devices may be relayed by UAV Computing System 322 after being interpreted or translated and may even be circumscribed by UAV Computing System 322 to prevent misuse, collisions or other issues. UAV Computing System 322 can use such commands to control the direction, velocity and other behavior of the Unmanned Aerial Vehicle 320 using any combination of previously programmed information present in the UAV Data Storage 324 (including remote storage), information from built-in sensors such as a GPS (Global Positioning System) sensor and remote commands originating from a different device or different system.

Figure 4A:
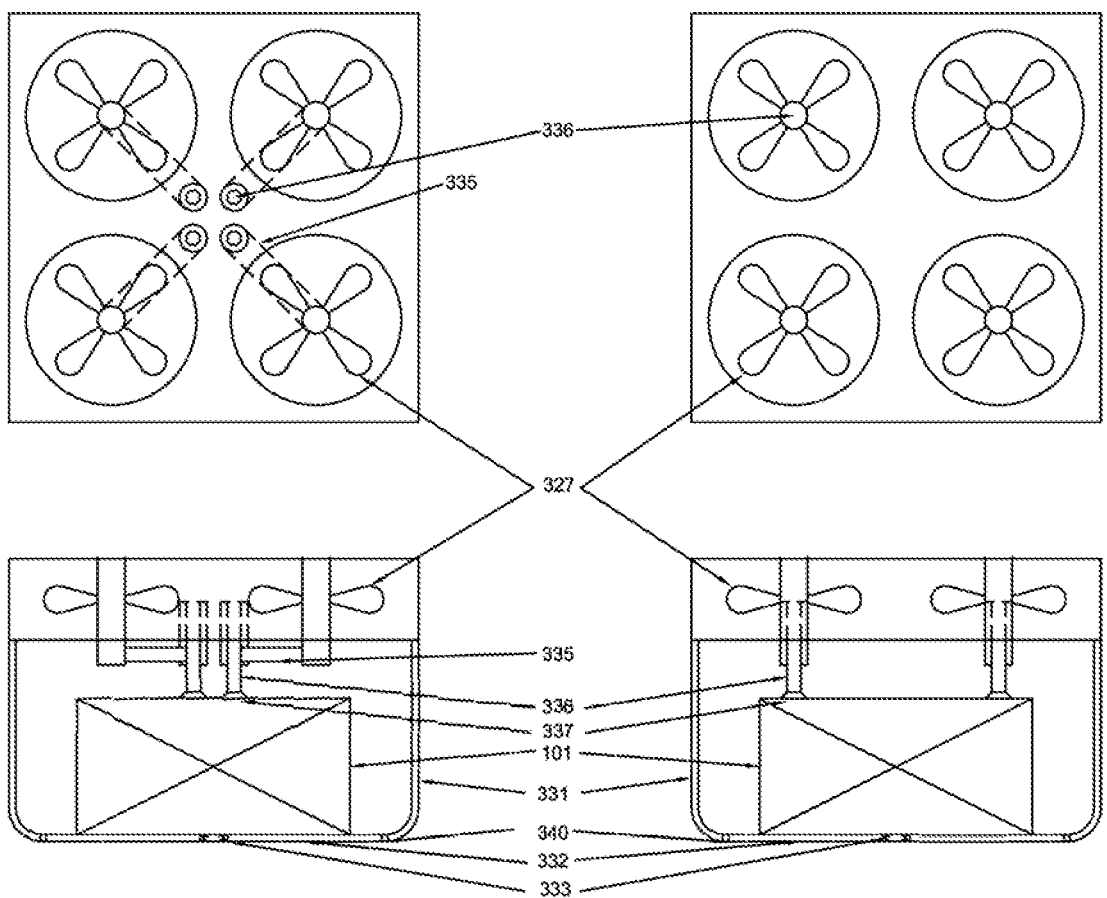
FIGS. 4A and 4B illustrate exemplary representations of a UAV.
Figure 4B:
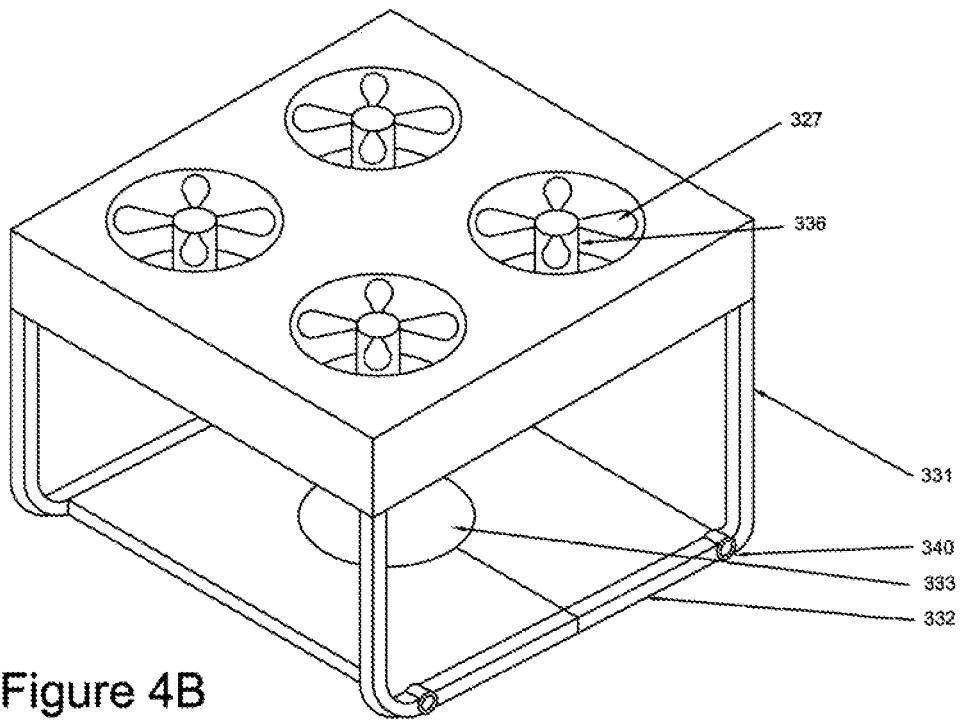

In an aspect, UAV 320 can include a UAV Package Handling Apparatus 330 for pick up and delivery of Packages 101, and is comprised of at least some of the following components as shown in FIGS. 4A and 4B,—UAV Fixed Arms 331, UAV Swiveling Arms 332, UAV Drive Chain Mechanism 335, UAV Extending Arms 336, UAV Suction Cups 337, UAV Valve 338, UAV Pressure/Weight Sensor 339, UAV Hinge 340 and UAV Solenoid 341. A UAV Camera A 333 and a UAV Camera B 334 (jointly and severally referred to as UAV Camera) may also be mounted on said apparatus and although not directly involved in handling of packages can be used to guide said handling process. In the present disclosure, when referring to common properties or actions of UAV Camera A 333 and UAV Camera B 334 or when said cameras are acting in conjunction, these cameras are jointly or severally called UAV Camera(s). Thus, UAV Cameras may also be used for other purposes such as navigation, collision avoidance and so on. The disclosed UAV 320 can, for example, move to a Pod 200 whose location has been transmitted to the recipient or shipper to pick up or drop off a Package 101. In an aspect, Package 101 may have physical elements such as special markings or codes or even hooks, handles, and other such mechanical components that are recognized by or complement elements on the UAV 320 that allow it to pick up or drop off the Package 101.

In an aspect, UAV 320 can be an Autonomous Vehicle, a partially Autonomous Vehicle (i.e. partially or occasionally controlled by a human operator) or can be a user controlled vehicle. Similarly, Unmanned Terrestrial Vehicle 350 can be an Autonomous Vehicle, a partially Autonomous Vehicle (i.e. partially or occasionally controlled by a human operator) or a fully user controlled vehicle.

In an aspect, an Unmanned Terrestrial Vehicle 350 (UTV) can have at least a UTV Computing System 352, comprising a UN Computing Application 353 with a UN Data Storage 354 operatively coupled to a UN Communication Module 355. A UN Camera A 363 and a UN Camera B 364 (jointly and severally referred to as UN Camera) may also be mounted on said apparatus and although not directly involved in handling of packages can be used to guide said handling process. UN Camera 363/364 may also be used for other purposes such as navigation, collision avoidance and so on. In addition, UN 350 may comprise UN Electro-Mechanical System 357, and a UN Package Handling Apparatus 360. UN Electro-Mechanical System 357 can include any or a combination of propulsion engine, motors, gears and any other physical parts, fixed or moving, which facilitate and control its movement. UN Mechanical System 357 can be controlled by UN Computing System 352 through the UN Communication Module 355 or via a direct connection to, for example, relays, motors and the like. Commands to control the UN Mechanical System 357 can originate from a remote user or remote system, from a proximal user, or from the UN Computing System 352. Commands from other devices may be relayed by UN Computing System 352 after being interpreted or translated and may even be circumscribed by UN Computing System 352 to prevent misuse, collisions or other issues. UN Computing System 352 can use such commands to control the direction, velocity and other behavior of the Unmanned Terrestrial Vehicle 350 using any combination of previously programmed information present in the UN Data Storage 354 (including remote storage), information from built-in sensors such as a GPS (Global Positioning System) sensor and remote commands originating from a different device or different system.

Figure 5A:
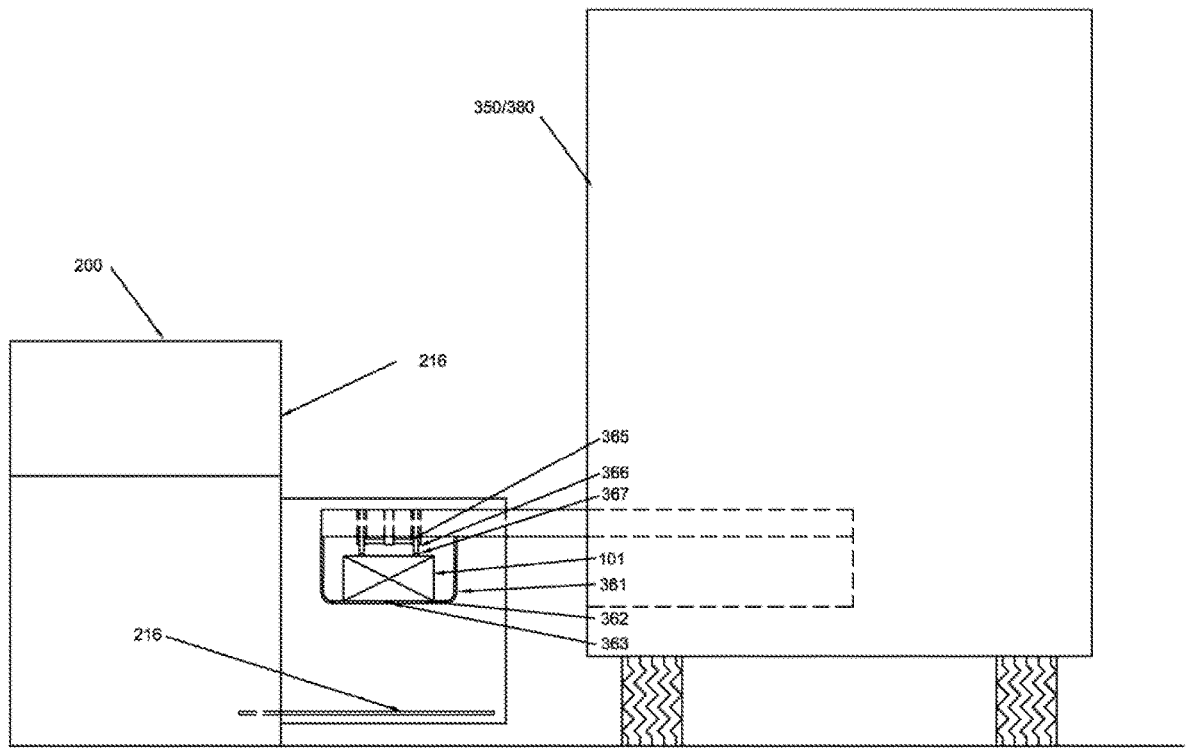
FIGS. 5A and 5B illustrate exemplary representations of a UTV and also common portions of a Manned Vehicle.
Figure 5B:
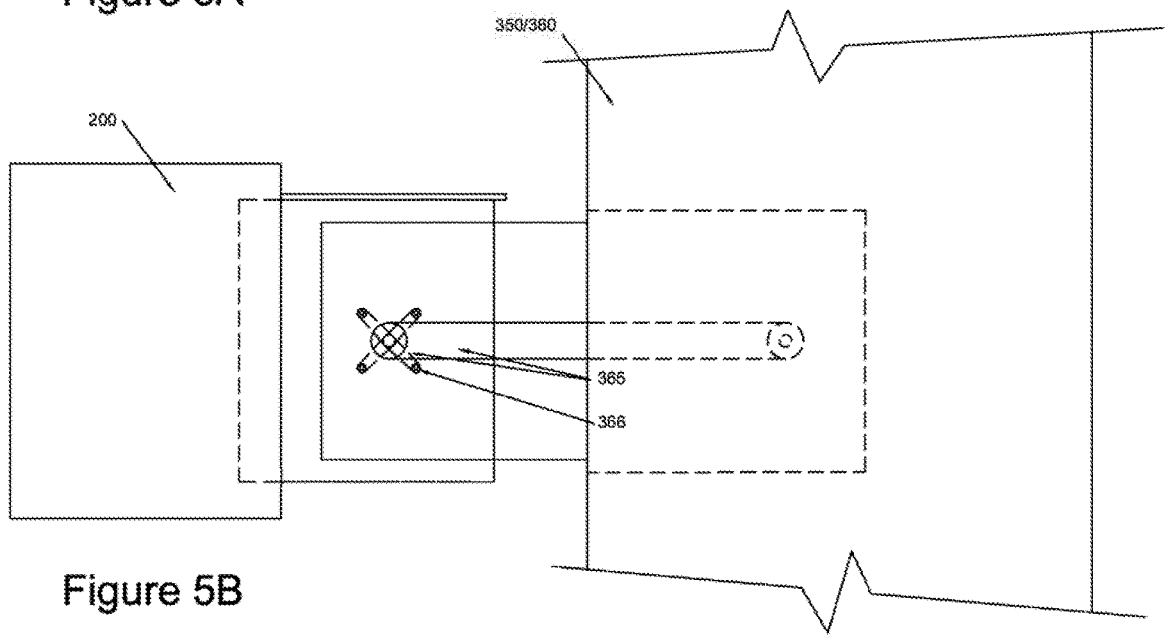

In an aspect, UTV 350 can include a UN Package Handling Apparatus 360 for pick up and delivery of Packages 101, and is comprised of at least some of the following components as shown in FIGS. 5A and 5B,—UN Fixed Arms 361, UN Swiveling Arms 362, UN Drive Chain Mechanism 365, UN Extending Arms 366, UN Suction Cups 367, UN Valve 368, UN Pressure/Weight Sensor 369, UN Hinge 370 and UTV Solenoid 371. A UN Camera 363 may also be mounted on said apparatus and although not directly involved in handling of packages can be used to guide said handling process. UN Camera 363/364 may also be used for other purposes such as navigation, collision avoidance and so on. The disclosed UN 350 can, for example, move to a Pod 200 whose location has been transmitted to the recipient or shipper to pick up or drop off a Package 101. In an aspect, Package 101 may have physical elements such as special markings or codes or even hooks, handles, and other such mechanical components that are recognized by or complement elements on the UN 350 that allow it to pick up or drop off the Package 101.

A UAV 320/UN 350 can send a message to a remote location manned by a Remote Operator 375 such that the Remote Operator 375 can send commands to control the mechanical systems and the camera of the UAV 320/UN 350 to guide the UAV 320/UN 350 to a more favorable location. In an aspect, the Remote Operator 375 can be a computer running artificial intelligence software capable to guide the mobile device to a more favorable location.

In an aspect, Pick-up/Delivery Agent 300 can include, as an example a Manned Vehicle 380 operated by a human, the latter actually delivering Package 101 to Pod 200 or Pod-Bank 230. The said human delivery person then is the same as Human Agent 310. If the delivery person and the operator i.e. driver of Manned Vehicle 380 are different, operator is now Manned Vehicle Operator 381, Manned Vehicle 380 may include substantially the same features as Unmanned Aerial Vehicle 320 or Unmanned Terrestrial Vehicle 350 including for example, Manned Vehicle Computing System 382, Manned Vehicle Computing Application 383, Manned Vehicle Data Storage 384, Manned Vehicle Communications Module 385, Manned Vehicle Meta Instructions 386, Manned Vehicle Mechanical System 387, Manned Vehicle Package Handling Apparatus 390, Manned Vehicle Fixed Arms 391, Manned Vehicle Swiveling Arms 392, Manned Vehicle Hinge 393, Manned Vehicle Camera 394, Manned Vehicle Drive Mechanism 395, Manned Vehicle Extending Arms 396, Manned Vehicle Suction Cups 397, Manned Vehicle Valve 398, Manned Vehicle Weight/Pressure Sensor 399 and others as applicable.

In another aspect, Pick-up/Delivery Agent 300 can include, as an example a Manned Vehicle 380 operated by a human and equipped with one or more Unmanned Aerial Vehicle 320, Unmanned Aerial Vehicle 320a, Unmanned Terrestrial Vehicle 350, Unmanned Terrestrial Vehicle 350a etc., wherein the Manned Vehicle 380 may drive to a certain preferred location which is more or less central to the location of multiple deliveries or near to a single delivery and the operator may be capable to send out one or more Unmanned Aerial Vehicle 320 to deliver one or more Package 101 to one or more Recipient 103. This serves to illustrate one combination and many more combinations of the above-enumerated examples of the Pick-up/Delivery Agent 300 are envisaged. In the above description, we can substitute a UN 350 that drives itself to the preferred location and then activates one or more UAVs 320 or UN 350a to complete delivery of Package 101. Even a Manned Vehicle 380 without any other associated manned or unmanned vehicles may be illustrative of the present invention if connected to Pick up and Delivery System 100 and enabled with appropriate Manned Vehicle Package Handling Apparatus 390 which may be identical in function and structure to UAV Package Handling Apparatus 330 or UN Package Handling Apparatus 360. It will be obvious to a practitioner of the art after learning the current examples that combinations not disclosed in the current description may also be included as illustrations of Pick-up/Delivery Agent 300. Any other combination of how a delivery agent(s) is chosen and used for delivering/picking packages is completely within the scope of the present disclosure.

In the present disclosure, no claims are made about certain features of unmanned vehicles including UAV 320 and UN 350; particularly the ability of such vehicles to adapt to adverse conditions which affect for example flight or other locomotion, or features such as collision detection and collision avoidance as these are assumed to be built-in where necessary. In an example, the ability of UAV 320 to fly to a proximal location to Pod 200 and hover around the Pod 200 in order to locate a graphic (for identification) or to locate an opening (for picking up or delivering a package) is assumed to exist in said UAV 320.o Server 400

In an exemplary embodiment, Server 400 can be a physical server or a virtual server (such as a cloud based server) or a combination of physical and virtual servers and includes computing and storage resources, plus at least a connection to the Internet or other networks that allow it to send, receive and store Messages 110 relating to the parts of the system. Server 400 can include a Server Computing System 402 and a Server Communication Module 405, wherein the Computing System can include a combination of physical and virtual servers working together and further include at least a Server Computing Application 403 and Server Data Storage 404, the latter being used for storing information in files, databases and any another form as appropriate. Server Data Storage 404 can conceivably store the above-named information in a local storage and at least a portion of it in external data storage. The above components are also described more generally above and additional descriptions are eschewed in the interests of brevity. Server Computing System 402 processes information and Messages 110 and encrypts and decrypts messages as required. Some encrypted messages may be sent from one of the components of Pick-up and Delivery System 100 to the Server 400 acting as a hub and the Server 400 sends such messages to another component of the Pick-up and Delivery System 100 without decrypting or otherwise modifying it.

In an aspect, Server 400 can also be a single application server such as a Mail server, Web (HTTP) server, FTP server and so on or it may run multiple applications. Server Communication Module 405 can allow connectivity to external components not part of the system such as other servers (e.g. those belonging to a retailer or logistics company), other networks (e.g. POTS networks, Telecom company networks, peer-to-peer and mesh networks), communication modules that are part of mechanical systems (e.g. logistics companies' warehouse conveyor belts) and other devices (e.g. Unmanned Vehicles). In another aspect, Server 400 can be multiple servers acting in tandem. For example, a first server belonging to an eCommerce Retailer may work in conjunction with and may at least partially synchronize data with a logistics company's server and an enquiry for example for an address of a Recipient 103 at first server is handled by first server querying the second server when said information is not present on first server and the response to the enquiry is then presented by first sever when it receives said information from second server.

Another type of server used in Pick-up and Delivery System 100 can preferably be a virtual server that uses computing and storage resources on one of the devices in Pick-up and Delivery System 100 and is typically configured by the appropriate computing system to act in a manner similar to Server 400. Such a server, now called Device Server 410 can send and receive Messages 110 to and from other components of Pick-up and Delivery System 100 including to the device that it is configured on as well as store said messages. Like above-mentioned computing devices and server 400, Device Server 410 can include a Device Server Computing System 412 and a Device Server Communication Module 415 that may include at least a portion of hardware and software of the device that it is configured on. As an example, a Device Server 410 may be associated with Pod 200, wherein, code and data that comprises Device Server Computing Application 403 is stored in Device Server Data Storage 404 which may be at least in part the same as Pod Data Storage 204 and such a portion of Pod Data Storage 204 may be called Device Server Data Storage 404. Pod Computing Application 203 may execute said code (Device Server Computing Application 413) in order to start, stop or control Device Server 410 and may do so based on commands or requests issued by another device such as Pod Owner Device 251 or UAV 320. Alternately, the Pod Owner Device 251 or UAV 320 can start, stop or control Device Server 410 directly if permitted by Usage Rights 271 for example, or other configuration present in Pod Data Storage 204.

In an aspect, one difference between Server 400 and Device Server 410 is typically addressed via a fixed and public IP (Internet Protocol) address. Device Server is often configured to connect to a Local Network 106 and typically has a private IP address, and in this case, must be addressed using different technologies, preferably DDNS (Dynamic Domain Name System). DDNS permits lightweight and immediate updates often using an update client, which provides a persistent addressing method for devices that change their configuration or IP address frequently or use a private IP address. In order to achieve this, the device on which Device Server 410 is configured may map a combination of at least one of one or more ports, and one or more protocols, and one or more external (public) IP addresses, to a corresponding combination on Device Server 410 using one or more commonly known methods such as mapping, tunneling forwarding and other technologies to achieve the desired ends. Alternately, no mapping is performed and a Fully Qualified Domain Name (FQDN) is configured for said Device Server 410 so that it can be accessed directly by other devices.

In an aspect, an important element of the proposed Pick-up and Delivery System 100 is the process of shipping in which there are multiple examples. In a first example, Package 101 is picked up from one Pod 200 and delivered to another Pod 200a. In a second example, Package 101 is picked up from a Sender 102 such as a merchant, a Common Carrier or even an individual to a Pod 200, which includes one of more methods as described earlier, namely including a Pick-up/Delivery Agent 300 plus Trucks, Air Cargo, and others. In a third example, Package 101 is picked from a Pod 200 to a final recipient without a Pod, which includes an individual recipient such as a person or a business, but may also include an eCommerce retailer. This method is illustrative of returns but may also be used for other purposes such as for merchants to ship to an eCommerce platform or fulfillment center, or even from one individual or business to another. All these exemplary possibilities may use a combination of one or more Common Carriers and third-party logistics companies, wherein the parcel is picked up from one Pod 200, goes through other methods of transportation including a Pick-up/Delivery Agent 300 plus Trucks, Air Cargo and others and is delivered to another Pod 200a.

Exemplary Implementations

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Below is provided an example embodiment of messaging between components of Pick-up and Delivery System 100. It should be noted that this being an example embodiment, it is not to be seen as limiting the scope of the invention in any way. In fact, the example presented here teaches messages between certain devices but the methods so taught can be mapped to any other devices in the current invention that have been described as having a communication module.

In an aspect, the present disclosure relates to a computer implemented system to improve the pick-up and delivery of Packages 101. The system can include a Pod 200, and can be configured to receive, at a first computing device associated with a Pick-up/Delivery Agent 300, from at least one of a Pod Owner 250/Pod User 260/Pick-up and Delivery System Server 400, a first Message 110a identifying the Pod 200. System can further be configured to receive, at a second computing device associated with a Pod, a second Message 110b identifying a Pick-up/Delivery Agent 300, wherein the Pick-up/Delivery Agent 300 contacts the identified Pod 200 based on the first Message 110a so as to unlock the Pod 200 based on the first message 110a. For instance, the first Message 110a sent by a Pod Owner 250 to a Pick-up/Delivery Agent 300 can include a Pod Passcode 213, a Pod UID 211, and one or more of Pick-up/Delivery Connection Information 301, Pick-up/Delivery Payment 302, Pick up Address 304, Pick up Information 305, Delivery Address 306, Delivery Information 307, and Package and Shipping Information 130, based on which the Pick-up/Delivery Agent 300 can locate the Pod 200 using means disclosed in the present disclosure, and unlock the Pod 200 using the unlock code to deliver/pick up the Package 101.

In an aspect, the Pod 200 is relocked and rendered unavailable to be opened by any Pick-up/Delivery Agent 300 until a third Message 110c is received.

In another aspect, the Pick-up/Delivery Agent 300 can be selected from any or a combination of a Human Agent 310, an Unmanned Aerial Vehicle 320, and Unmanned Terrestrial Vehicle 350 and a Manned Vehicle 380.

In an exemplary aspect, Pick-up/Delivery Agent 300 can contact the Pod 200 by sending a Message 110d using for example SMS, such that any other second Message 110e with the same content from a different one or more Pick-up/Delivery Agent 300a, Pick-up/Delivery Agent 300b and so on, does not unlock the Pod 200. In such a case, the Message 110d is recognized by the receiving Pod 200 as originating from the Pick-up/Delivery Agent 300 (using for example the Caller ID associated with said SMS), whereas Message 110e is recognized by the receiving Pod 200 as not originating from the Pick-up/Delivery Agent 300.

In another exemplary aspect, Pick-up/Delivery Agent 300 can contact the Pod 200 by means of a phone call to the Pod 200 by the Pick-up/Delivery Agent 300 such that a phone call from a different one or more Pick-up/Delivery Agent 300a, Pick-up/Delivery Agent 300b and so on does not unlock the Pod 200. In an aspect, the phone call can be answered by the Pod 200 and no action may be taken or can be taken only when at least one of a spoken command associated with said action, a specific sound associated with said action, and a DTMF tone is transmitted by Pick-up/Delivery Agent 300 and received by Pod 200.

In another exemplary aspect, Pick-up/Delivery Agent 300 can contact the Pod 200 by means of an SMS from the Pick-up/Delivery Agent 300 to the receiving Pod 200, wherein the content of the message is associated with a specific action and the action is only performed when the Caller ID of the sending device is recognized by the Pod 200.

It is to be appreciated that any other form of message such as a network/data packet, a message sent over a local network, or a signal transmitted over a telecommunication network can be issued by the Pick-up/Delivery Agent 300 such that the message can be mapped/checked against the second Message 110b (identifying the Pick-up/Delivery Agent 300) that the Pod 200 stores in its storage for checking authenticity of the Pick-up/Delivery Agent 300, and accordingly unlocks/locks Pod 200.

In an aspect, any of the Messages 110a, 110b and so on above are sent using one protocol (for example as an SMS) and when no response is received from a recipient of said message, said message is sent again using at least one of a different protocol and a different transmission method and this is repeated with additional protocols and transmission methods until a message is received in reply indicating successful communication.

In an aspect, Message 110a sent to the Pick-up/Delivery Agent 300 to identify the Pod 200 can include at least one of a code that must be sent to the Pod in order to unlock it, a time period in which and only in which the Pick-up/Delivery Agent 300 can unlock the Pod 200, a flag signifying whether or not the Pick-up/Delivery Agent 300 can unlock the Pod 200 more than once using the same code, and a flag signifying whether or not the Pick-up/Delivery Agent 300 can unlock the Pod more than once within the specified time period.

In an aspect, when the Pod 200 is locked, Pod Computing System 202 sends a message to Pod Camera 208 to record at least one of at least a picture of the Package 101 and a video of the Package 101 for local storage or transmission to at least one of a Server 400, a Pod Owner 250, a Pod User 260, a Sender 102, and a Recipient 103.

In another exemplary implementation, the proposed system includes at least a Pick-up/Delivery Agent 300 and at least a Pod 200 where the Pick-up/Delivery Agent 300 locates the Pod 200 with increasing accuracy by sequentially using at least one of a Global Positioning System, a Short-Range Positioning System, a Local Precision Positioning System, and a Manual/Operator Assisted Positioning System.

At a broader level, the present disclosure further relates to a computer-implemented system to connect a device to a multiplicity of networks by automatically switching between a first network and at least a second network, wherein connection to the first and second networks is switched at a first time and for at least an interval of time. The first time and the interval of time can be determined by at least one of a user configuration, network connection status, a random number generated by a computing application, a series of rules in a computing application, said rules based on usefulness of a connection being active.

In another aspect, the present disclosure relates to a first device such as Pod 200 enabled with an electronic lock, wherein the first device includes a second device such as Receptacle 220 with an electronic lock so that first device and second device can be unlocked with the same electronic code, or first and second device can be unlocked with different electronic codes, or first and second device can be unlocked with different electronic codes, but second device can be unlocked only if first device is also unlocked. In an exemplary implementation, first device must be unlocked and opened in order to access second device 220, whereas in another implementation, first device does not need to be unlocked or opened in order to access second device 220. It is also possible that the first device must be unlocked but does not need to be opened in order to access second device. Any other combination of how a Pod and one or more of its Receptacles are used is completely within the scope of the present disclosure.

In an exemplary implementation, the present disclosure relates to a Short Range Positioning System comprising a stationary device and a mobile device, the mobile device including multiple sensors, each sensor of the multiple sensors being powered by graduated power levels designed to sense a signal from the stationary device such that each sensor senses the signal from the stationary device at varying distances based on the power level of each sensor, the distances providing a basis for the mobile device to locate the stationary device. In case the mobile device is unable to locate the stationary device within a maximum time to locate, the mobile device can send a message to a remote location manned by a Remote Operator 375 such that the Remote Operator 375 can send commands to control the mechanical systems and the camera of the mobile device to guide the mobile device to a more favorable location. In an aspect, the Remote Operator 375 can be a computer running artificial intelligence software capable to guide the mobile device to a more favorable location.

In one example, a delivery may be scheduled to Pod 200 by a recipient such as Pod Owner 250/Pod User 260/Recipient 103 from a sender such as Sender 102/Pod Owner 250/Pod User 260. In this example, Pod 200 receives a Message 110 (through Pod Communication Module 205) from, for example, the Pod Owner 250/Pod User 260/Recipient 103. Here, Pod Owner 250 and Pod 200 may be connected to each other through a local Wi-Fi network via their respective communications modules. A practitioner of the art will appreciate that Wi-Fi is but one example of a network type with a corresponding protocol and that any other technology or protocol or any combinations of these may be used without affecting the present invention. This connection is considered permanent for all practical purposes since the devices remain connected to the network (and therefore to each other) when they are powered up and within range, without requiring a password or other explicit authentication to reconnect. Additionally, in this example, Pick-up/Delivery Agent 300 arrives at, and needs to connect to Pod 200 to send a message requesting that Pod 200 accept delivery of Package 101 by unlocking and/or opening Pod 200. Pod Communication Module 205 may include another module, for example a second Wi-Fi sensor (the first being connected to the permanent Local Network 106), a Bluetooth sensor or any other sensor matching a similar sensor on the communication module of the Pick-up/Delivery Agent 300. As an example, if the Pick-up/Delivery Agent 300 is an Unmanned Aerial Vehicle 320, the connection will be made to the UAV Communication Module 325. The network created between the respective communication modules of Pod 200 and a relevant device of Pick-up/Delivery Agent 300 is also termed a Local Network 106a, however, in this case designated as a temporary network since it may be turned off or destroyed when the delivery is completed or when UAV 320 leaves the proximity of Pod 200 and flies out of range. In some cases, more than one networks are required to be active, for example the permanent network between Pod Owner Device Communication Module and the Pod Communication Module 205 (for updates on delivery schedules for example), and the temporary network between Pod Communication Module 205 and UAV Communications Module 325 (when a delivery is imminent for example) and these may respectively be termed Local Network 106 and Local Network 106a.

Note that the present invention teaches that the existence of Local Network 106a is independent of the number of devices and when at least a device is put in a state that it can connect to another device on the network, that network is said to be active. Further, the said network may be active on a multiplicity of devices and said devices may be connected in the sense of being capable to pass messages to each other for example, even if they are not yet in range. As an illustration, if a UAV 320 is enroute to deliver a Package 101 to a Pod 200, both Pod 200 and UAV 320 may enable a temporary Local Network 106a. However, regardless of the fact that UAV 320 may not be within the minimum distance required to establish connectivity with Pod 200, we treat the Local Network 106a as active. In some cases, Pod Communication Module 205 is connected to the Local Network 106 and thence to Pod Owner Device Communication Module 255, and is not comprised of any other communication module or protocol matching one on the communication module of the relevant device of Pick-up/Delivery Agent 300. In this case, the same module must be used to communicate with the Local Network 106 and the Local Network 106a. To enable this, Pod Computing Application 203 triggers a command at certain intervals that switches Pod Communication Module 205 from one network to the other. As an example, Pod Computing Application 203 may maintain a connection to Local Network 106 as its normal or default state, and switch to Local Network 106a every 30 seconds, for an interval of 5 seconds. These times may vary and even be reversed, for example a continuous connection to Local Network 106a may be maintained when a delivery is imminent and a connection to Local Network 106 may be activated every 30 seconds for 5 seconds.

In an exemplary implementation of the proposed system, a first entity such as a person or business i.e. Sender 102 may wish to send a package to a second such entity i.e. Recipient 103, and one or both of these entities may not own a Pod 200. This part of the description addresses Pick up where no Pod is present (delivery may or may not be to a Pod 200 in the same transaction), and Delivery where no Pod 200 is present (Pick up may or may not have been from a Pod 200 in the same transaction). Naturally, pick up or delivery by a Human Agent is not taught as it is trivial and commonly practiced today. Even delivery by any unmanned vehicle to a location marked by a symbol for example has already been illustrated and demonstrated by various companies today. However, all such demonstrations show only delivery and in that context, show a package being dropped from a height onto a surface—this can damage the contents of the Package and is therefore not suitable for many deliveries. Further, such demonstrations do not demonstrate real life applications where accuracy of delivery is important. The present disclosure demonstrates various methods including hovering/standing of unmanned vehicles to allow Sender 102 to load Package 101 on the unmanned vehicle for pick up (First Embodiment described below), hovering/standing of unmanned vehicles to pick up Package 101 from a preferred and accurate location for pick up (First Embodiment described below), hovering/standing of unmanned vehicles to place a package at a preferred and accurate location for delivery (Second Embodiment described below), and hovering/standing of unmanned vehicles to allow Recipient 103 to retrieve Package 101 from the unmanned vehicle for delivery (Also Second Embodiment described below)

Message Based Negotiation

A method is described wherein two entities, for example a Sender 102 and a Recipient 103 are communicating in the process of arranging pick up or delivery of a package. This method is described generally here for a Sender 102 and Recipient 103 but can be applied to any similar communication. In an example, at least a Pod Owner 250 is communicating with UAV 320 wherein UAV 320 is to deliver a Package 101 to a Pod 200. In another example, a UTV 350 is picking up from a Pod 200 or a Direct Sender 140. Many other such combinations are possible are described elsewhere in this disclosure, particularly under the various embodiments, and the example or examples illustrated here should not be taken to be limiting in any way to the present invention or any of its embodiments and aspects. Further, in an aspect, actual communication may be handled by a surrogate entity, for example, a at least Server 400 may perform at least an aspect of communication for a Pod Owner 250; and in yet another aspect, at least a third entity may be involved in a Message Negotiation Process (as described under Synchronized Communication) and these aspects should also not be taken to be limiting in any way. We now illustrate this embodiment using the general case of a UAV 320 delivering a Package 101 to a Pod 200.

As previously described, Pod 200 includes a Pod Computing System 202, Pod Computing Application 203, Pod Data Storage 204 and can communicate with other entities in Pick-up/Delivery System 100 using Pod Communication Module 205. Similarly, UAV 320 is enabled with analogous components. Thus, each of these entities is capable of using said components for computing requirements of Delivery, and communicating aspects of said Delivery to the other entity.

In an aspect, Pod 200 may send a Message 110 related to a Delivery to UAV 320 and said message may include information required to complete the delivery such as Delivery Address 306 and Delivery Information 307. Delivery Information 307 can include for example Pod UID 211, at least one Pod Passcode 213 as well as information about the Pod 200 such as sizes, receptacles and so on, and any other information relevant to and useful for delivery. More particularly relevant to the present description, said information can include for example, some combination of Usage Role 270, Usage Rights 271, Usage Period 272 (for example proposed time frames for the delivery) and Pick-up/Delivery Connection Information 301. UAV 320 replies to the above Message 110 with Message 110a which may contain an acceptance flag or an unchanged copy of the information from Message 110 implying acceptance of proposed information or it may respond with new information including any combination of Usage Role 270a, Usage Rights 271a, Usage Period 272a and Pick-up/Delivery Connection Information 301a. For example, Sender 102 is sending a perishable item and may want UAV 320 to have the ability to turn on cooling apparatus which is part of Pod Electro-Mechanical System 207, this being embedded in the Usage Rights 271a requested. Further, Sender 102 or Third-Party Logistics Provider 104 may want delivery to be performed at a certain time and this is embedded in requested Usage Period 272a. In another related aspect, Pod 200 and UAV 320 may need to agree on a protocol or technology to communicate in order to, for example unlocking Pod 200, and this is embedded in Pick-up/Delivery Connection Information 301. Although it is possible to unlock a Pod 200 through other means such as communicating via a Server 400 (as taught elsewhere in this disclosure), it may be more appropriate (for business reasons such as reliability for example) for such communication to occur through a Local Network 106. Thus, both Pod 200 and UAV 320 will, in this case, need to share at least one common protocol or communication technology. Pod 200 can match information in Message 110a with matching information in its respective data storage and determine if the requested Usage Role 270a, Usage Rights 271a, Usage Period 272a and Pick-up/Delivery Connection Information 301a, are feasible and permissible; and also, if a requested connection is possible given its capabilities. For example, Pod Owner Device Data Storage 254 may contain a table of expected Pick-ups or Deliveries and related Usage Periods expected to be used by Pod Owner 250 or blocked by others such as another Pod Owner 250a or Pod User 260, 260a and so on. If, for example, requested Usage Role or Usage Rights are within the normal parameters configured for a UAV 320, and if requested Usage Period 272 does not overlap any existing Usage Periods blocked for other transactions or by others, the request can be approved. To accept, Pod 200 returns a Message 110b comprising an acceptance flag or an unchanged copy of said information thus signifying acceptance. Using Usage Period 272 as a specific example, Pod 200 may be scheduled for another delivery during at least a portion of Usage Period 272a or at least a portion of Usage Period 272a may conflict with other Usage Periods that have been claimed by at least one of other Pod Owner 250a, 250b etc., Pod Users 260, 260a, 260b etc., and any other entity related to Pod 200. Pod 200 is capable to compute all available times by looking up data in Pod Data Storage 204, blocking out time intervals already booked and sending the rest to UAV 320 or sending the earliest free time interval, this being sent as Usage Role 270b, proposed Usage Rights 271b, Usage Period 272b and Pick-up/Delivery Connection Information 301b. In such a case, request may be rejected. To reject, Pod Owner 250 may instead return the changed information in Message 110b. UAV 320 then repeats the above process i.e. either returning information unchanged or sending new proposed information as another Message 110c. This process iterates between the two entities until one of the entities returns a message with information unchanged or an acceptance flag or until a count is reached which is equal to a value saved in Pod Data Storage 204 or a value saved in UAV Data Storage 324 (whichever is lower). The said value is a maximum available count of negotiation messages and if said value is reached by the count, there is apparently no fit in at least one of Usage Role 270, Usage Rights 271, Usage Period 272 or Pick-up/Delivery Connection Information 301 between the two entities and the Delivery is cancelled. If, however, agreement is reached as described above by, for example, a return of a message with unchanged information from either Pod 200 or UAV 320 the process proceeds to the next step.

Synchronized Communication

In the Embodiments described elsewhere in the present disclosure, we teach for example, a Pod Owner 250 communicating with a Pick-up/Deliver Agent 300, say a UAV 320 (or its surrogates such as a Server 400 or Sender 102) in order to negotiate and determine a fit based on at least one of a Usage Role 270, Usage Rights 271, Usage Period 272 and Pick-up/Delivery Connection Information 301. As described, in some cases, Pod 200 is also capable and may be enabled to communicate and negotiate, by Pod Computing Application 203 using data in Pod Storage 204, and can therefore analyze messages received, and send messages to UAV 320. Other combinations are also possible, such as Third-Party Logistics Provider 104 and Server 400 communicating with UAV 320. In other words, two entities can communicate with a single other entity simultaneously or in a relay. To continue the combination described in the first example above, Pod Owner 250 may start communicating with UAV 320, but may have to travel out of range of networks or may simply become too busy to make a timely reply to a communication from UAV 320. In such a case Pod 200 can take over the communication and complete the rest of the process of communication as needed or until Pod Owner 250 returns to the process. We now describe how said two entities can synchronize communication if both are communicating with said single entity in one of these formats using the above example of Pod Owner 250 and Pod 200 communicating with UAV 320.

Pod Owner 250 may transmit at least a Message 110 to UAV 320 in which required information is included for a Pick up or a Delivery. Such information may include one or more of Pick up Address 304, Pick up Information 305, Delivery Address 306, Delivery Information 307, Package and Shipping Information 130, Pod UID 211, at least a Pod Passcode 213 and so on. More importantly, as explained elsewhere in the present disclosure the information in Message 110 may also include Usage Role 270, Usage Rights 271, Usage Period 272 and Pick-up/Delivery Connection Information 301 giving UAV 320 certain rights in its role of Pick-up/Delivery Agent 300. UAV 320 may return a message with an acceptance flag or an unchanged copy of the information from Message 110a implying acceptance of proposed information or it may negotiate new versions of said information by responding with a new combination of Usage Role 270, Usage Rights 271, Usage Period 272 and Pick-up/Delivery Connection Information 301. This process of alternating communication of information between both parties in order to determine best fit of said information may be in multiple iterations (described in more detail under Message based Negotiation). If Pod 200 and Pod Owner 250 are both involved in such communication, then Synchronized Communication may become necessary.

In order to ensure communication remains synchronized, Pod Owner 250 may also transmit at least a portion of Message 110 as Message 110a to Pod 200 either manually or automatically. Pod Owner 250 may add an instruction to Message 110a, or may send another Message 110b, or may separately configure Pod 200, to enable Pod 200 to communicate with UAV 320. Pod 200 may under certain circumstances communicate with UAV 320 in order to schedule and enable Pick up or Delivery of Package 101. In the present disclosure, both are described as communicating and also synchronizing their communication as this is the most encompassing example, but either or both may perform said communication. For this, Pod Computing Application 203 and Pod Owner Device Computing Application 253 may include common computing code, algorithms, data and the like to make such communication possible.

As described earlier Pod Owner 250 Sender 102 may forward at least a portion of Message 110 to Pod 200 for example through Server 400 again through one of a Synchronization process and Server Computing System 402 sending at least a portion of said message to Pod 200. Sender 102 may also send Message 110 directly to Pod 200 using External Network 105. At least a portion of Message 110 may additionally be sent to a Pick-up/Delivery Agent 300. As described above, Pod Owner 250 may send a Message 110b to Pod 200 with at least a portion of Message 110 and said Message 110b and may also include a flag that asserts that it has responded, and when Pod 200 receives said message, it does not respond to Sender 102 or other elements of Pick-up/Delivery System 100. Alternately, when Pod 200 begins communication with other elements of Pick-up/Delivery System 100 as described above it may send a Message 110d to Pod Owner 250 asserting that it has responded and when Pod Owner 250 receives said message, it does not respond to Sender 102 or other elements of Pick-up/Delivery System 100. However, if either Pod 200 or Pod Owner 250 receives a message 110e specifying that a response is pending, then either or both devices may respond and the receiving entity may choose either message depending on rules embedded in said device. An example of such a rule may be that a message from Pod Owner 250 may take precedence over a message from Pod 200. If Pod 200 does not receive Message 110e from Sender 102 within a time interval less than a value saved in Pod Data Storage 204, it responds to Sender 102 with a Message 110a specifying the information enumerated above, thus substituting for Pod Owner 250. The sharing of communication now taught is more fully illustrated below.

If information is received from more than one source, Server 400 reconciles information received according to an internal set of rules already programmed into Server Computing Application 403. For example, in case of conflict or contradiction, an internal rule may override any information received from Pod 200 with information received from Pod Owner Device 251, the latter being considered more reliable since it has presumably been seen and/or entered by a human. A reverse rule is also possible where Server 400 trusts automated process of Pod 200 over manual process of Pod Owner 250. Pod Owner 250 sends aforementioned Message 110b through an interface including but not limited to Pod Owner Device 251, the World Wide Web, an App, Web based forms, Voice based interaction with a manned or automated customer service, Interactive Phone System or any method not repugnant to the context to Server 400.

Synchronization and Data Sharing of Components

Exemplary synchronization can be performed between Pod Owner Device Computing Application 253 and Pod Computing Application 203, Pod User Device Computing Application 263 and Pod Computing Application 203, and Pod Owner Device Computing Application 253 and Pod User Device Computing Application 263. All the above synchronizations can be done with or without a Server 400 being part of the process.

First Embodiment—Pick Up without Pod

Figure 6A:
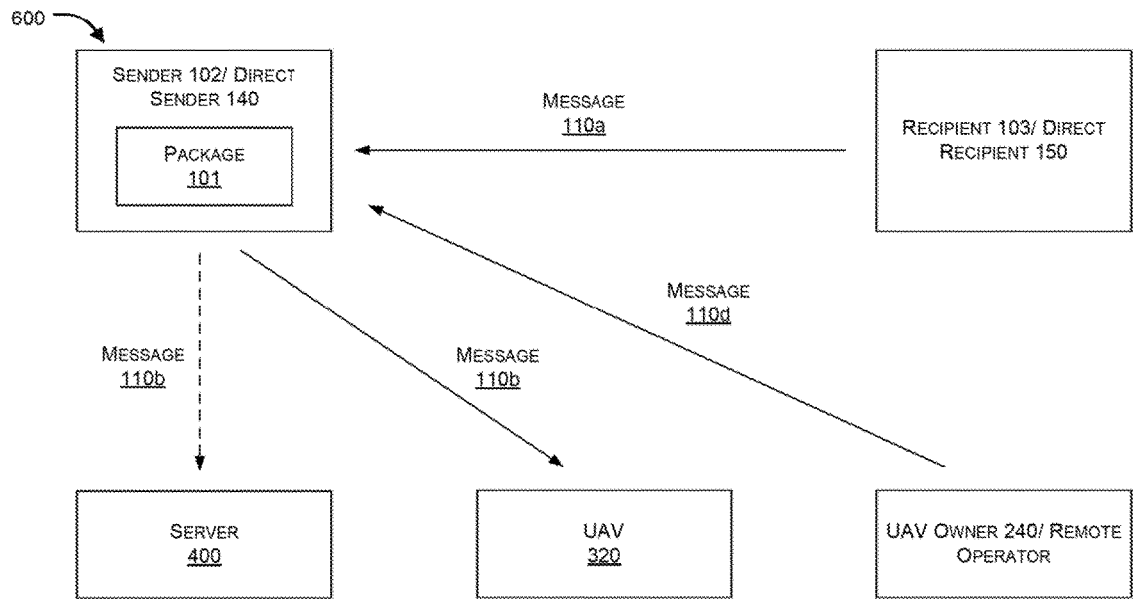
FIGS. 6A to 6C illustrate exemplary message flows between stakeholders of the proposed system.

With respect to FIG. 6A, in the First Embodiment illustrating Pick up without Pod, the Package 101 is to be shipped from Sender 102 to Recipient 103. Sender 102 does not have a Pod 200 and therefore must enable other means for Pickup of Package 101; hence Sender 102 is now called Direct Sender 140. In another example, Recipient 103 wants to request a Package 101 from Sender 102 and therefore initiates a Pick up. Here too, Sender 102 does not have access to a Pod 200 and is therefore designated Direct Sender 140. Further, an unmanned vehicle such as UAV 320 or UTV 350 is to be used to transport Package 101. Pick up by a Human Agent 310 is not taught as it is trivial and commonly practiced today, and the focus in this embodiment is on unmanned vehicles. Hence, in the description of this embodiment Pick-up/Delivery Agent 300 and UAV 320 are used interchangeably, and may be interpreted in a more or less identical manner for a UTV 350 as well.

In the present embodiment, Recipient 103 may be a Direct Recipient 150 but is referred to more generally as Recipient 103 in order to encompass all those roles. In some cases, a Server 400 (belonging to a retailer, logistics company or any third party) may already have at least one address of Recipient 103, such as when latter is an existing customer of the entity that owns or operates a Server 400 (e.g. a retailer) or is a recipient of a previous delivery (e.g. by a logistics company). Such information may also be saved in Direct Recipient Device Data Storage 154. If appropriate information is saved, such as at least one address, Direct Recipient 150 may have the option of retrieving one of the saved addresses (e.g. the default address) from, for example, Direct Recipient Device Data Storage 154 or from Server Data Storage 404, and sending this information as Delivery Address 306 and may also optionally send Delivery Information 307.

Direct Sender 140 or Recipient 103 may own an unmanned vehicle. Alternately, a third party such as Third-Party Logistics Provider 104 may own such a vehicle. Any of the parties may initiate the process of sending a vehicle. In some cases, retailer/merchant, Direct Sender 140 and Third-Party Logistics Provider 104 are the same. Third Party Logistics Provider 104 may initiate the process as a result of a separate eCommerce or other type of transaction at a merchant and may not even be involved in such a transaction but may receive at least one of a notification and a request. If Recipient 103 is the initiator of the pickup, Recipient 103 sends a Message 110 to Direct Sender 140, or by completing a separate transaction such as a purchase causes a Message 110 to be sent to Direct Sender 140. If Direct Sender 140 is the initiator of the Pickup (based on a message from say a retailer with whom Recipient 103 has completed a transaction or if Direct Sender 140 wants to send a Package 101 to Recipient 103 for any reason) then Direct Sender 140 may request the information by sending a Message 110aa to Recipient 103 or a Server 400 where this information is stored. Direct Sender 140 or Server 400 may already have such information from a previous transaction. Message 110 may include information such as Delivery Address 306, Delivery Information 307, information about Package 101 such as Package and Shipping Information 130 (including for example physical dimensions and weight), Pick-up/Delivery Connection Information 301 and Pick-up/Delivery Payment 302. If initiated by Direct Sender 140, Message 110 may also include Pick up Address 304, Pick up Information 305 and so on. In some cases, Message 110 may not contain all the information, but may contain a means to obtain said information, such as a URL to said information. If known to Recipient 103 from say, past use and if available from a menu of choices, Recipient 103 may also include specific model of vehicle or specific vehicle for Pick up and subsequent Delivery. Recipient 103 my alternately directly book an unmanned vehicle by sending Message 110 to Server 400 which may be owned and operated by Third Party Logistics Provider 104, Pick-up/Delivery Agent 300 owner, Direct Sender or Recipient 103. If known to Direct Sender 140 from say past use or from a menu of choices, Direct Sender may also include specific model of vehicle or specific vehicle for Pick up and subsequent Delivery. Server 400 may in some cases, be part of UAV 320 i.e. run as part of UAV Computing Application 322 on UAV Computing System 323, and such a server is now referred to as Device Server 410 for the discussion of the present embodiment. Thus, when Server 410 sends messages to UAV 320, the messages are being sent from one application to another within the same computing system i.e. locally within UAV Computing System 322. Recipient 103 may be a user recognized by Server 400 or Server 410 and may optionally be required to login. If not recognized as a user, Recipient 103 may be required to create an account and then login.

In an aspect, Direct Sender 140 prepares Package 101 for delivery and transmits a Message 110a to Server 400 or UAV 320 requesting a Pick up. Message 110a may include Delivery Address 306 and Delivery Information 307 and preferably also Pick up Address 304, Pick up Information 305 (including that it is a direct pick up i.e. without a Pod, which as described elsewhere is enabled by setting Pod UID 211 to null) and details about Package 101 such as physical dimensions and weight as Package and Shipping Information 130. Pick up Information 305 may also include a flag specifying the loading mode i.e., whether Package 101 will be manually loaded onto UAV 320 by a person or whether it will be picked up from a surface. The surface can be any location that Package 101 can be left so that UAV 320 can approach it, hover over it, and pickup said Package 101. For example, Direct Sender 140 may leave Package 101 for pick up on a table, patch of ground, on a terrace or any similar place. During preparation of Package 101 for pick up, Direct Sender 140 may print a label that includes Recipient 103's address and other details. Included on the label can be Direct Sender's details including a name or code as a portion of Pick up Information 305 that is printed in the form of a graphic, bar code, QR code or any such format. UAV 320 may include one or more a UAV Camera that can read said graphic, bar code, QR code or other format and interpret it to recognize said code. Reading and interpreting said code can confirm identity of Sender as well identity of package 101 (thus ensuring the correct package is picked up when multiple packages are present in the vicinity). The code can be part of Pick-up/Delivery Connection Information 301 as described under System Architecture and can be used to connect UAV 320 and Direct Sender Device 141 as described below. Matching the code on Package 101 with the code provided in Pick up Information 305 also ensure the reverse, that is that the correct UAV 320 picks up the Package 101. In an alternate aspect, a Package Homing Device 120 may be embedded in Package 101 which allows UAV 320 to find and recognize the Package 101.

Message 110a from Direct Sender 140 may be transmitted by SMS, Wi-Fi or by any other appropriate protocols or technologies and Direct Sender may, for example use Direct Sender Computing Application, an ordinary browser, an SMS application or any other application to do so. If sent to Server 400, Message 110a is transmitted to UAV 320 as Message 110b after adding additional details if necessary. Direct Sender may be a user recognized by Server 400 or Server 410 and may optionally be required to login. If not recognized as a user, Direct Sender may be required to create an account and then login. Based on past use, at least one of Pick up Address 304, Pick up Information 305 may already exist on Server 400 and those may not be sent once Direct Sender 140's identity is established by login. Also, once logged in, Direct Sender may choose Recipient 103's information based on past use of same, and include it in Message 110a to UAV 320.

Server 400 or Server 410 may dispatch, for example, an Unmanned Aerial Vehicle 320 (or Unmanned Terrestrial Vehicle 350) to Sender 102 having first also sent a Message 110b including if appropriate, additional details such as Pick up Address 304 (as confirmation), Pick up Information 305 (including Pick up time, pick up mode, vehicle details and the like). Message 110b may also include Delivery Address 306 and Delivery Information 307 (again as confirmation—see Message based Negotiation for purpose). Alternatively, Message 110b may contain only a Pick-up Address 304 and Pick up Information 305, but a second Message 110c may be sent later, say, after pick up is completed and second Message 110c may contain Delivery Address 306 and Delivery Information 307. Message 110b also includes a Pick-up/Delivery Connection Information 301 comprising for example, unique code or password (also known as Network Security Key), a connection name and details of a protocol all three of which can be used later to connect and authenticate Direct Sender Device 141 and UAV 320 to each other. The owner of the UAV 320 also sends a Message 110d to Direct Sender 140 that is received by the Direct Sender Device 141, the Message 110c containing the same code or password sent to it in Message 110b. Direct Sender Device 141 creates an Access Point or Server in Direct Sender Device Communication Module, using Wi-Fi or Bluetooth or any similar technology whose protocol and access password has been communicated in Message 110b. As described under System Architecture above, addresses may be converted to GPS coordinates by Direct Sender Computing Application 143 or it may be converted at any Server 400. Message 110 may also include information about Direct Sender Device such as available protocols in Direct Sender Device Communication Module 145 so that Pick-up/Delivery Agent 300 can determine the best protocol to use for communication at the time of Pick up.

UAV 320 then moves to Pick up Address 304 using Gross/Global Positioning System (See Gross/Global Positioning System in this description) so as to arrive within the time window prescribed in Pick up Information 305. When UAV 320 reaches Pick up Address, it turns on the correct communication protocol and searches for the connection name both of which were received in Message 110b. Since Direct Sender Device 141 has already configured such an Access Point with the correct name and protocol, UAV 320 finds the connection and connects to it using the password also supplied to it in Message 110b, thus creating a Local Network 106.

Once a connection is established, UAV 320 may attempt to further articulate its position by using Short Range Positioning System. Also, once connection is established, Direct Sender 140 sends messages or signals using the user interface of Direct Sender Device Computing System 142 to UAV 320 that is to UAV Computing System 322. These messages include messages sent in real-time to move UAV 320 in a certain direction, stop movement to hover UAV 320 and so on—the purpose being to bring UAV 320 into a position that Direct Sender can deposit Package 101 into UAV Package Handling Apparatus 330. UAV 320 receives the messages through UAV Communications Module 325 and processes them in UAV Computing Application 323. UAV Computing Application 323 analyzes the messages and determines if they can be acted upon based on a determination of whether they will conflict with UAV Meta Instructions 326, or conflict with the parameters of allowable actions, or result in a safety issue (such as a collision) for UAV 320 or Direct Sender 140 or any other objects in the environment. If no conflict or safety issue is found, and the instructions are acted upon, Direct Sender can bring UAV 320 to a landing point or allow it to hover in the air and then place Package 101 into the UAV Package Handling Apparatus 330.

During the time that UAV 320 is being controlled by Direct Sender 140, UAV 320 attempts to create a connection through a Local Network 106 using Pick-up/Delivery Connection Information 301, for example through Direct Sender Device 140 or through Direct Sender 140's home/work Wi-Fi network, or through any open networks detected, or through any commercial network(s) to which the owner of the UAV 320 has subscribed or through any other available network it may detect. If unsuccessful, UAV 320 may also attempt to connect to an External Network 105. Once connected to any network, it can transmit images or video to a Remote Operator 375 such as one who is an employee of the company that owns the UAV 320. In certain cases, Direct Sender 140 may not be capable of or may not want to control UAV 320 in order to position it and may send a Message 110d through an External Network 105 or Local Network 106 to a Remote Operator 375 to control the vehicle. A precondition for control being passed to Remote Operator 375 is that UAV 320 has a connection to the operator through one of the above networks. This Remote Operator 375 may take control of UAV 320 by transmitting messages over the network connection, and by doing so can assist Direct Sender 140 or take over completely and substitute for Direct Sender 140.

In an alternate example, no human control is required because UAV 320 may use Package Homing Device 120 to find Package 101 and pick up said package using UAV Package Handling Apparatus 330 as described later in the context of pick up from a Pod 200. Alternately, UAV 320 may use Package Graphic 129 to recognize Package 101 as well as to position itself over Package 101 using Local Precision Positioning System taught elsewhere in this disclosure.

In an aspect, one exemplary advantage of using Local Network 106 is that it creates a protected connection between Direct Sender Device 141 and UAV 320 and therefore Package 101 cannot be hijacked by a malicious user by hijacking said UAV 320/UN 350.

UAV 320, using UAV Camera A 333 or UAV Camera B 334 (now severally or together referred to as UAV Camera) may record a video or a multiplicity of pictures at predetermined intervals to record the Pick up as a legal record. The images may be transmitted to whichever entity is legally responsible for storage of the record or further disposition (such as sending a proof of pick up to Sender 102 or original retailer). Once Package 101 is deposited into UAV 320 by Direct Sender 140 or retrieved from a receiving surface by UAV 320, UAV 320 retreats to a position out of reach of Direct Sender 140 and sends a Message 110 to Server to be stored and to act as confirmation of pick up of Package 101. This Message 110 can serve as a legal confirmation of Pick up of Package 101, in particular if accompanied by one or more pictures or video. Thus, UAV Camera or YTV Camera may capture at least an image or video of delivery operation and this may be initiated by one or more of Recipient 103, Direct Sender 140, UAV 320, Remote Operator 375 or any entity capable and authorized to do so. At least one of images and video may, be for example be stored locally in UAV Data Storage 325 and may be transmitted for storage on a Server 400. The images and video severally and jointly may server as proof of Pick up.

Second Embodiment—Delivery without Pod

Figure 6B:
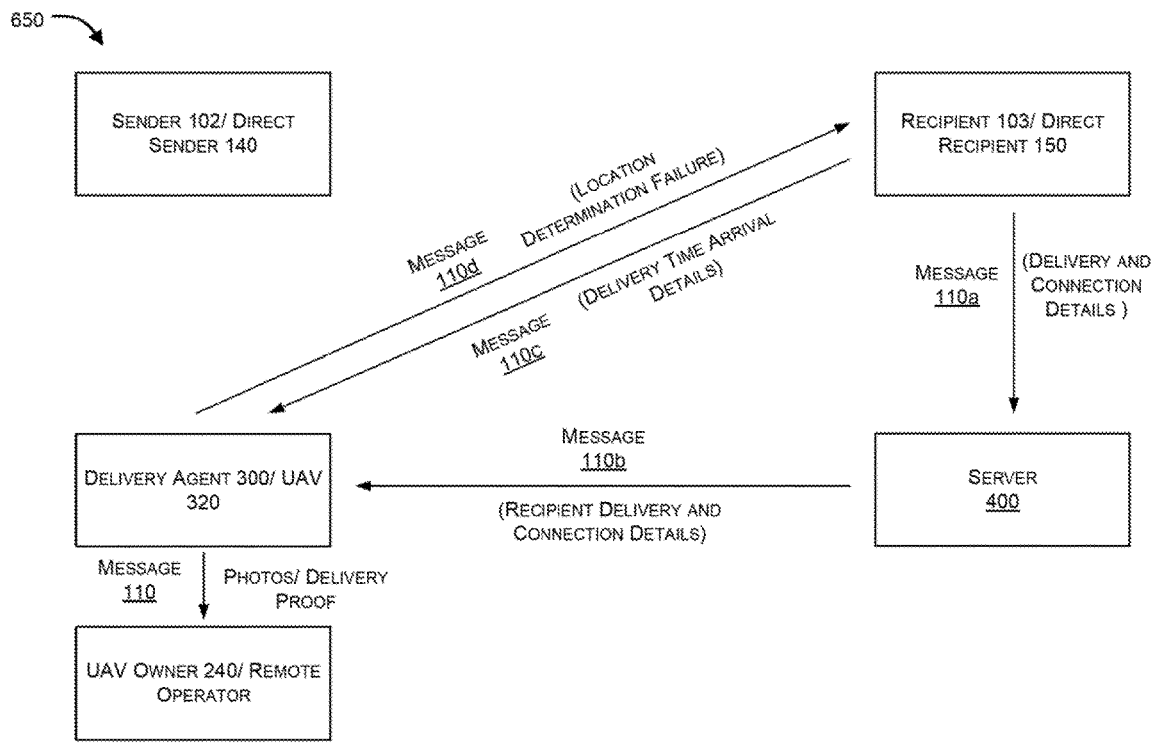

FIG. 6B illustrates a scenario where delivery of a Package 101 to a Recipient 103 takes place and where the recipient does not have a Pod 200 and must receive Package 101 by other means; such a recipient is now designated Direct Recipient 150. Delivery by a Human Agent 310 is not taught as it is trivial and commonly practiced today, and the focus in this embodiment is on unmanned vehicles. Hence, in the description of this embodiment Pick-up/Delivery Agent 300 and UAV 320 are used interchangeably, and may be interpreted in a more or less identical manner for a UTV 350 as well.

In this embodiment, Sender 102 may be a Direct Sender 140, Pod Owner 250, Pod User 260 or Third-Party Logistics Provider 104 (shipping on behalf of a merchant) and therefore will be called Sender 102 to encompass all those roles. Similar to the previous Embodiment (Pick up without Pod) Sender 102, Recipient 103 (in this case Direct Recipient 150), Third Party Logistics Provider 104 or owner of a fleet of unmanned vehicles may own an appropriate vehicle and any of them may have initiated a pick up and subsequent delivery to Direct Recipient 150. Third Party Logistics Provider 104 may initiate the process as a result of a separate eCommerce or other type of transaction. In some cases, Sender 102 and Third-Party Logistics Provider 104 are the same. The present embodiment only deals with delivery of Package 101 to Direct Recipient 150. Pick up of said delivery may previously have happened with or without a Pod, and that does not affect this embodiment.

It can be assumed for the purposes of this embodiment that Package 101 has been picked up and UAV 320 has received Delivery Address 306 and Delivery Information 307 as previously described and this information has been received as Message 110. If not, these may be requested by Pick-up/Delivery Agent 300 by sending a query to a Server 400 or to Pod Owner 250 or Recipient 103 or any appropriate entity that has said information. Delivery Information 307 may contain at least one of at least one preferred delivery time period, a communication protocol to be used, and any additional free form instructions entered by Recipient 103.

Direct Recipient 150 may receive, on Direct Recipient Device 151 (via Direct Recipient Device Communication Module 155), a Message 110a specifying at least one of a communication protocol, an expected delivery time, a code used as a connection name, a code used as a connection password from Server 400. Server 400 may be owned or operated by Direct Sender 102, Pod Owner 250, Pod User 260, Third Party Logistics Provider 104 or any third party such as a Merchant or individual. Server 400 may in some cases, be part of UAV 320 i.e. run as part of UAV Computing Application 323 on UAV Computing System 322, and such a server is now referred to as Server 410 for the discussion of the present embodiment. Another Message 110b may be sent to a Pick-up/Delivery Agent 300 again containing similar information, but said Message 110b may also contain identification information of the Recipient Device 151. Pick-up/Delivery Agent 300 in the form of an Unmanned Aerial Vehicle 320 or an Unmanned Terrestrial Vehicle 350 may be dispatched to the coordinates representing Recipient 103's address and simultaneously Message 110c may be sent to Recipient 103 with details of the delivery or pick up such as arrival time of the vehicle.

UAV 320 then flies to Delivery Address using Gross/Global Positioning System (See Gross/Global Positioning System in this description) so as to arrive within the time window prescribed by Delivery Information 307. When UAV 320 reaches Delivery Address, it turns on the correct communication protocol and searches for the connection name both of which were received in Message 110. Since Direct Recipient Device 151 has already configured such an Access Point with the correct name and protocol, UAV 320 finds the connection and connects to it using the password also supplied to in Message 110. UAV 320 may attempt to further articulate its position by using Short Range Positioning System and Local Precision Positioning System. For the latter, it may use Pick-up/Delivery Graphic 131 such as a bar code, QR code, image, graphic or other means that Direct Recipient 150 has placed on a surface capable of receiving the package. If it is unable to do find the precise location to place Package 101, it may then send a Message 110d to Direct Recipient Device 151 with a code or flag signifying its failure.

If a connection has been established, Direct Recipient 150 sends one or more messages or signals using the user interface of Direct Recipient Device 151 to UAV 320 using their respective communication modules. These messages include signals to move UAV 320 in a certain direction, stop i.e. hover UAV 320 and so on—the purpose being to bring UAV 320 into a position that Direct Recipient 150 can retrieve Package 101 from UAV Package Handling Apparatus 330 or UAV 320 can deposit Package 101 on a prepared surface as described earlier. UAV 320 receives the messages through UAV Communications Module 325 and passes them on to UAV 320. UAV Computing Application 323 analyzes the messages and determines if they can be acted upon based on a determination of whether they will conflict with its meta instructions, conflict with the parameters of allowable actions, result in a safety issue (such as a collision) for UAV 320 or Direct Sender or any other objects in the environment. If no conflict or safety issue is found, and the instructions the instructions are acted upon. Direct Recipient 150 can bring UAV 320 to a landing point or allow it to hover in the air and then retrieve Package 101 from the UAV Package Handling Apparatus 330.

During the time that UAV 320 is being controlled by Direct Recipient 150, UAV 320 attempts, using Pick-up/Delivery Connection Information 301 to create a connection through a Local Network 106, for example through Direct Recipient Device 151 or Direct Recipient 150's home Wi-Fi network, any open networks detected, any commercial networks to which the owner of the UAV 320 has subscribed, or through any other available network it may detect. If unsuccessful at making a connection, UAV 320 may also attempt to connect to an External Network 105. Once connected to any network, it can transmit images or video to a Remote Operator 375 such as one who is an employee of the company that owns the UAV 320. In some cases, Direct Recipient 150 is not capable or does not want to control UAV 320 in order to position it and may send a Message 110e through an External Network 105, External Network 105a, Local Network 106 or a Local Network 106a to a Remote Operator 375 to control the vehicle. A precondition for control being passed to Remote Operator 375 is that UAV 320 has a connection to the operator through one of the above networks. This Remote Operator 375 may take control of UAV 320 by transmitting messages over said network connection, and by doing so can assist Direct Sender 140 or take over completely and substitute for Direct Sender 140. If UAV 320 is capable of connecting to more than one network, it may connect to External Network 105 as well as Local Network 106 in order to perform the functions described above. In an alternate aspect, if UAV Communication Module 325 is capable of connecting to only a single network, it may switch between networks at intervals or at the command of Direct Recipient 150 or Remote Operator 375.

UAV 320, using UAV Camera A 333 or UAV Camera B 334 (now severally or together referred to as UAV Camera) may record a video or a multiplicity of pictures at predetermined intervals to record the Delivery as a legal record. The images may be transmitted to whichever entity is legally responsible for storage of the record or further disposition (such as sending a proof of delivery to Sender 102). Once Package 101 is removed from UAV 320 by Direct Recipient 150 or deposited onto a receiving surface by UAV 320, UAV 320 retreats to a position out of reach of Direct Recipient 150 and sends a Message 110 to Sender 102 confirming delivery of Package 101. This Message 110 can serve as a legal confirmation of Delivery of Package 101, in particular if accompanied by one or more pictures or video. Thus, UAV Camera or YTV Camera may capture at least an image or video of delivery operation and this may be initiated by one or more of Direct Recipient 150, Sender 102, UAV 320, Remote Operator 375 or any entity capable and authorized to do so. At least one of images and video may, be for example be stored locally in UAV Data Storage 325 and may be transmitted for storage on a Server 400. The images and video severally and jointly may also server as proof of delivery.

In an aspect, Sender 102 can query the Recipient 103 whether they have a Pod 200 and if so, collect details thereof from the customer and supply to the Pick-up/Delivery Agent 300, wherein the relevant information can include, but is not limited to, Pick up Address 304, Pick up Information 305, Delivery Address 306, Delivery Information 307, Pod UID 211, and other information necessary to enable the pick up or delivery of a Package 101. The Carrier may be a Common Carrier, a third-parry logistics company or the internal Shipping Department of the retailer or even Sender 102.

Third Embodiment—Delivery to a Pod

Figure 6C:
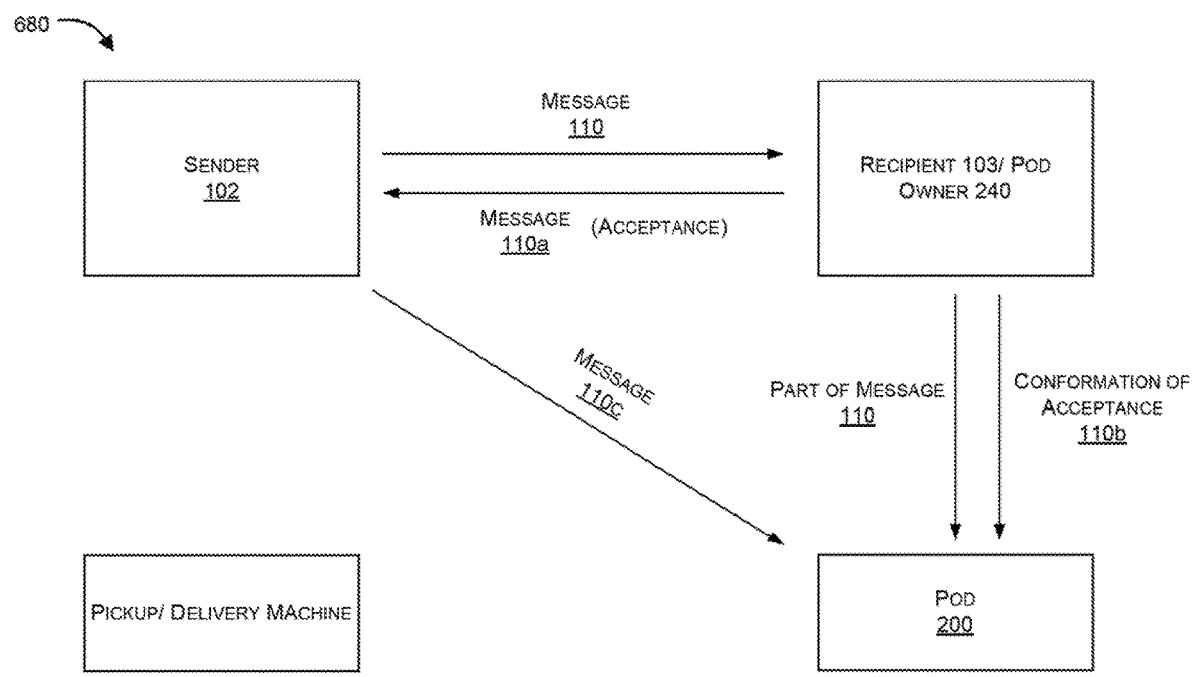

In this exemplary embodiment, Recipient 103 can be a Pod Owner 250 or Pod User 260 or any person embodying any Usage Role 270 that allows and is capable of receiving a Package 101 to Pod 200 on their behalf, or receives a delivery at a Pod 200, and the present description should not be seen to be limiting in any way to any other possible Usage Role 270 with a specific combination of Usage Rights 271. Below description of this embodiment uses Pod Owner 250 as an example, but other entities enumerated above may be substituted without any loss of meaning and without limiting the present invention in any way. In this embodiment, with reference to FIG. 6C, Pod 200 and Pod Owner Device 251 can be configured, and Pod 200 and Pod Owner 250 can be authenticated and registered with each other as described under "Step of Setting up a Pod". Therefore, Pod Owner 250 may be capable of sending messages to operate Pod 200 including, for example requesting information from sensors in Pod 200, operating heating/cooling elements or locking/unlocking Pod 200 remotely or proximally for Pick up or Delivery of Package 101. Pod Owner 250 may also be capable of sending messages to Pod 200 that are informational or related to scheduling Delivery or Pick up.

In an implementation, a Package 101 is to be sent by Sender 102 (a Retailer, an intermediary such as a third-party shipping/logistics company, an individual or any other type of sender) to a Recipient 103, for example as a result of an eCommerce transaction or a transaction or agreement between individuals. Sender 102 may send a Message 110 to Recipient 103 with information about relevant shipping and package details (such as Package and Shipping Information 130) and may also include a request for information. Message 110 may be sent directly to Recipient 103 by sending to a device owned by Recipient 103, or via a Server 400; and Recipient 103 may return a Message 110a to Sender 102 with details of a Pod 200 owned by said Recipient 103. If such details of a Pod 200 are included in Message 110a, Sender 102, through appropriate device (for example Direct Sender Device 141 or if Sender 102 is a Pod Owner 250a, then through Pod Owner Device 251a) will send Package 101 to said Pod 200 and Recipient 103 is now called Pod Owner 250 (or other usage role such as Pod User 260 etcetera as enumerated above). Thus, we now illustrate the present embodiment of Delivery to a Pod 200 in more detail.

As described above, Message 110a may include information required to complete the delivery such as Delivery Address 306 and Delivery Information 307. Delivery Information 307 can include for example Pod UID 211, at least one Pod Passcode 213 as well as information about the Pod 200 such as sizes, receptacles and so on, and any other information relevant to and useful for delivery. Delivery Information 307 can include for example proposed Usage Role 270, proposed Usage Rights 271, Usage Period 272 (for example proposed time frames for the delivery) and Pick-up/Delivery Connection Information 301 or any combination of these. Further communication between Sender 102 and Pod 200 is performed as described under "Message based Negotiation" and either a set of information consisting of Usage Role 270a, Usage Rights 271a, Usage Period 272a and Pick-up/Delivery Connection Information 301a is agreed upon or the delivery is cancelled as the negotiation is considered failed.

In the present example embodiment, where communication with Sender 102 is described, a Server 400 that is managed or owned by Sender 102 or by a Third-Party Logistics Provider 104 contracted by Sender 102 may be used instead as it is capable and enabled to communicate and compute Messages, Usage Roles and so on described above. Similarly, all communication with Pod Owner 250 may actually be done by another Server 400a which is managed by the Pick-up/Delivery System or another Third-Party Logistics Provider 104a contracted by Pod Owner 250 to manage Pick up and/or Delivery. Finally, in an aspect, Pod 200 may have the capability and may be enabled by Pod Owner 250 to perform the above tasks. In this latter aspect, Pod 200 may, using its Pod Computing System 202 and related elements, be capable to communicate and compute allowable Usage Roles, Rights and Periods. It should be apparent from this discussion that any device, for example Pod User Device 261 and UAV 320, in addition to the others just mentioned have common code, algorithms and data (which may be shared in a common data storage) and the like to compute and communicate as needed to facilitate delivery by negotiating allowable Usage Roles, Rights and Periods among others.

If Delivery parameters including at least a Usage Role 270, a Usage Rights 271, a Usage Period 272 and Package and Shipping Information 301 are chosen as described above and the information updated in respective storage of the various devices involved (including most importantly Pick-up/Delivery Agent 300) the Pick-up/Delivery Agent 300 proceeds for the Delivery. It should be noted that Sender 102 in the above description may have chosen a specific Pick-up/Delivery Agent 300 before communicating with Pod Owner 250 or may do so after negotiations for Delivery have been completed as described above. Pick-up/Delivery Agent 300 then uses Gross/Global, Short Range and Local Positioning Systems (each respectively described elsewhere in this disclosure) to arrive at Pod 200. Pick-up/Delivery Agent 300 may also use at least the above positioning systems to calculate travel time and thereby leave its home base at an appropriate time so as to reach Pod 200 within a first specified Usage Period 272.

On arrival near the Pod 200 to which delivery is made, UAV 320 uses UAV Camera A 333 or UAV Camera B 334 (jointly and severally now called UAV Camera) to scan said Pod 200 for Pod Graphic 212 from which it may extract Pod UID 211 in order to confirm its identity. UAV 320 also connects to a Local Network 106, preferably one established by Pod Communication Module 205, or alternately another network, for example a home Wi-Fi network of Pod Owner 250, using at least a portion of Pick-up/Delivery Connection Information 301 and unlocks the Pod 200 also using at least a portion of Pick-up/Delivery Connection Information 301.

Once the Pick-up/Delivery Agent 300 reaches the Pod 200, the Pod 200 can be unlocked by any of the methods described elsewhere in this disclosure (see Exemplary Steps in Operating a Pod). UAV 320 can use Local Precision Positioning System to position itself over Pod 200, and as described in System Architecture, a drawer or platform may slide out with an appropriate image, barcode, QR code or other graphic marked on horizontal surface, or a fixed horizontal surface may be marked for Delivery. As noted in description of the positioning system, UAV Camera A or UAV Camera B can be correctly used to position UAV 320 over said graphic. The package can then be placed into Pod Receptacle 220 through any or a combination of known methods such as a pad underneath Package 101 that contains air where the air slowly leaks out after a few minutes, or by means of a fan blowing compressed air upward, or by means of opposing magnets having same polarity magnets on each side (container and package) such that the magnets get turned on and off; all these methods designed to allow the Package 101 to descend slowly without unwanted and destructive impact. In a preferred embodiment, UAV Suction Cups attached to UAV Extending Arms are attached to the package and lower it into the Pod Receptacle 220 as described elsewhere in this disclosure.

Fourth Embodiment—Pick Up from Pod

In another exemplary embodiment, Pod Owner 250, Pod User 260 or other entity wants to send a Package 101 to a Recipient 103 and said entity owns, operates or has access to a Pod 200. In the description below, Pod Owner 250 is described, but may be substituted by any of the other entities enumerated above and even by Pod 200. As a first step, Pod Owner 250 prepares Package 101, preferably attaching a shipping label or Package Information 121 to Package 101 and then placing Package 101 into the Pod 200. Pod 200 may automatically sense intake of Package 101, using a component of Pod Electro-Mechanical System 207, for example a camera, weight sensor, proximity sensor or any other sensor or device appropriate to this example and working in conjunction with Pod Computing System 202. Pod Computing Application 203 receives input from at least one of Pod Electro-Mechanical System 207 and Pod Computing System 202 and is capable to recognize such a situation or event. Pod Computing Application 203 may also be configured to recognize a relevant event by recognizing that Pod 200 is unlocked or its door opened. In an alternate aspect, Pod Communication Module 205 can read information or receive information from Package Information Device 121. Package 101 may be scanned by Pod Owner 250 using Pod Owner Device 251 or any other device preferably before Package 101 is placed into Pod 200. Additionally, Pod Owner 250 may send a Message 110 to Pod 200 to use Pod Camera 208 to capture one or more images of Package 101 when placed in Pod 200.

Pod Computing Application 203 may store the image or images in Pod Data Storage 204 and also analyze said image or images thereby revealing a shipping label or other information label on Package 101 with simple text, one or more bar codes, one or more QR Codes, one or more graphic images or any other form of marking, such a label providing details about Package 101 as Package and Shipping Information 130, Pod Owner 250 or other sender information and recipient information. In some cases, label may also have Pick up Address 304, Pick up Information 305, Delivery Address 306, and Delivery Information 307 and any other relevant or useful information. At least an image captured y Pod Camera 208 may also be added to Pick up Information 305 for later use by Pick-up/Delivery/Agent 300. Said label may also contain part or even none of the above information if it contains a means to obtain said information such as for example, in the form of at least a URL to the information, authentication related information and decryption related information (if shipping label information is encrypted), to allow relevant user access to said information.

Pod Owner 250, using for example Pod Owner Device 251 may transmit at least a portion of Package and Shipping Information 130 as well as Pick up Address 304, Pick up Information 305 (including preferably Pod UID 211, Pod Passcode 213 and so on), Delivery Address 306, Delivery Information 307, and any other information relevant or useful to Pick up and Delivery of Package 101, to a Server 400 by transmitting it as Message 110a either by storing it locally and initiating a synchronization process or by using Pod Communication Module 205 to transmit said information using HTTP, FTP, Email and so on; in fact, any technology may be used to transmit said Message 110a. Server 400 is owned, operated, used, or managed by a Common Carrier, supplier/manufacturer of Pod 200 or a Third-Party Logistics Provider 104 or any other entity that can provide a Pick-up/Delivery Agent 300. Server 400 may also be jointly managed, operated or owned by any of the aforementioned entities. Pod Owner 250 may also send Message 110a directly to a recipient such as Direct Recipient 150 or another Pod Owner 250a if either are known to Pod Owner 250, for example from a previous transaction.

In certain cases, Server 400 may already have at least a portion of information sent as Message 110a, such as when Pod Owner 250 or recipient is an existing customer of the entity that owns or operates Server 400 (e.g. a retailer) or is a recipient of a previous Delivery or an initiator of a previous Pick up. Upon receipt of Message 110a, Server 400 may send a Message 110b to at least the Pod Owner 250, which message appears in Pod Owner Device 251. Server 400 may also include, in Message 110b, one or more of Usage Role 270, Usage Rights 271, Usage Period 272 and Pick-up/Delivery Connection Information 301. Pod Owner 250 can match information in Message 110b with matching information in its respective data storage and determine if the requested Usage Role 270, Usage Rights 271, Usage Period 272 and Pick-up/Delivery Connection Information 301 are feasible and permissible. At this point "Message base Negotiation" (see named section elsewhere in the current disclosure) begins and a fit on these parameters (namely Usage Role 270, Usage Rights 271, Usage Period 272 and Pick-up/Delivery Connection Information 301) is negotiated and determined. If after negotiation through multiple messages as described in the above-named section there is apparently no fit in at least one of Usage Role 270, Usage Rights 271 or Usage Period 272 between the two entities and the Pick up is cancelled. If, however, agreement is reached as described above by, for example, a return of a message with unchanged information from either Pod Owner 250 or Server 400 the process proceeds to the next step with Usage Role 270, Usage Rights 271 or Usage Period 272.

Server 400 may now supply the relevant information to a Pick-up/Delivery Agent 300 by sending a Message 110d with relevant shipping and package details such as one or more of Pick up Address 304, Pick up Information 305, Delivery Address 306, Delivery Information 307, Usage Role 270, Usage Rights 271, Usage Period 272, Package and Shipping Information 130 (which may include an image or images of Package 101), Pick-up/Delivery Connection Information 301 and any other useful and relevant information that may be used in the process. In addition, Pick up Information 305 may also include details of protocols or technologies to be used by Pick-up/Delivery Agent 300 such as Pick-up/Delivery Connection Information 301. In an aspect Message 110d is actually sent to a Server 400a, said Server 400a being owned or operated by owner of UAV 320 such as a Third-Party Logistics Provider 104 or a company that operates/manages a group or fleet of Pick-up/Delivery Agents 300.

As described earlier, Pick-up/Delivery Agent 300 may include a combination of humans and/or vehicles and at least one device with a computing system associated with said agent. If Pick-up/Delivery Agent 300 wants to accept Shipping Information described above, it sends a return Message 110e comprising an acceptance flag or an unchanged copy of the information implying acceptance of said proposed information or it may respond with new information in Message 110f including any combination of Usage Role 270a, Usage Rights 271a, Usage Period 272a and Pick-up/Delivery Connection Information 301. Again, as described earlier and earlier also reference, "Message based Negotiation" is now taught as a sequence of message which establishes if there is an agreement between the two entities on said parameters of Usage. If there is apparently no fit in at least one of Usage Role 270, Usage Rights 271, Usage Period 272, or Pick-up/Delivery Connection Information 301 (for example no matching communication technology) between the two entities, either the Pick up is cancelled, or Server 400 begins the negotiation process with another Pick up/Deliver Agent 300, and continues in this fashion until a match is found with at least one Pick up/Deliver Agent 300 or none of the Pick-up/Deliver Agents 300 are able to provide a match and the Pick up is cancelled. If, however, agreement is reached as described above by a return of a message with unchanged information from either Pick-up/Delivery Agent 300 or Server 400 (whichever is lower)s, Pick up process proceeds to the next step.

Pick-up/Delivery Agent 300 receives Pick up Address 304 and Pick up Information 305 and then uses one or more of Gross/Global, and Short-Range Positioning Systems to arrive in proximity to Pod 200. Pick-up/Delivery Agent 300 may also use the above positioning systems to calculate travel time and leave its home base at an appropriate time so as to reach Pod 200 within a first specified Usage Period 272. The following portion of the description describes a UAV 320 as Pick-up/Delivery Agent 300, but the description may be applicable to any Pick-up/Delivery Agent 300 and description using UAV 320 should not be seen as limiting the present invention in any way.

On arrival near the Pod 200 from which Pick up is to be performed, UAV 320 uses UAV Camera A 333 or UAV Camera B 334 (jointly and severally now called UAV Camera) to scan said Pod 200 for Pod Graphic 212 from which it may extract Pod UID 211 in order to confirm its identity. UAV 320 also connects to a Local Network 106, preferably one established by Pod Communication Module 205, or alternately another network, for example a home Wi-Fi network of Pod Owner 250, using at least a portion of Pick-up/Delivery Connection Information 301 and unlocks the Pod 200 also using at least a portion of Pick-up/Delivery Connection Information 301.

Once the Pod 200 is unlocked, UAV 320 uses Local Precision Positioning System to position itself over Pod 200. As described in System Architecture, a drawer or platform may slide out, or a door may be opened, and Package 101 is exposed. Package 101 may have on it an appropriate image, barcode, QR code or other graphic marked on horizontal surface. As noted in description of said positioning system, UAV Camera A or UAV Camera B is used to correctly position UAV 320 over said graphic. Said graphic may be a known image and as illustrated in FIG. 3A, and UAV Computing System 323 records and continuously analyzes said graphic as UAV 320 moves over Package 101, capturing a series of images at rapid intervals as UAV 320 moves over the package. These images are matched to an image in UAV Data Storage 324 in such a manner that UAV 320 correctly positions itself over Package 101. In some cases, there is no graphic or for any reason (e.g. low light levels) the graphic is not clearly visible, and UAV 320 uses the image or images of Package 101 captured in the first step described above. Image or images of Package 101 taken by UAV Camera A or UAV Camera B can be matched with image or images stored in UAV Data Storage 324 as transmitted in Message 110d. Matching process for graphic or Package 101 image(s) comprises comparing images using methods described in the Section Local Precision Positioning System. In some cases, one of more the automated Positioning Systems enumerated above fails for any reason (for example, Local Precision Positioning System cannot read image or graphic to position UAV 320). In such a case, a failure message is sent to Server 400 and Manual/Operator Assisted Positioning System may be used to correctly position UAV 320 (or UTV 350) to enable Pick up of Package 101.

In one example, each rotary motor driving a propeller of the UAV 320 is also attached to an UAV Extending Arm 336 of a UAV 320 via a UAV Drive Chain Mechanism 335. In the case of a UTV 350, the Extending Arms 366 can be attached to any mechanical system in the vehicle that is capable of driving the UN Drive Chain Mechanism 365 Each of the said Extending Arms ends in a Suction Cup 337/367. In an alternate configuration, the extending arms are affixed to a flat, rigid, horizontal element which in turn has a multiplicity of Suction Cups attached below it as shown in FIG. 8A.

Once UAV 320 is positioned correctly over Package 101, UAV 320 deploys UAV Package Handling Apparatus. First, UAV Swiveling Arms 332 are swiveled out of the way so that UAV Suction Cups 337 attached to UAV Extending Arms 336 have unimpeded access to Package 101. UAV Computing System 323 now activates a gear or connection between UAV Drive Chain Mechanism 335 and UAV Extending Arms 336 such that the latter begin to rotate around their central vertical axis. UAV Suction Cups 337 do not rotate as they are held freely in an orifice at the end of UAV Extending Arms 336. Since UAV Extending Arms 336 are enabled with a spiral thread, they are driven downward and continue downward until UAV Suction Cups 337 are pressed firmly against Package 101. At this time, the resistance encountered to downward movement results in resistance being transmitted to UAV Drive Chain Mechanism 335, which contains a sensor that transmits a Message 110g to UAV Computing System 323. Said sensor may be a ratchet or electronic sensor attached to either of the mechanisms here described. This causes UAV Computing System 323 to reverse the direction of rotation of inner core of UAV Extending Arms 336 by changing a gear. Before the reversal of the UAV Extending Arms 336, UAV Valve 338 is released or opened to release the vacuum in UAV Suction Cups 337, thus releasing the Package 101. UAV Valve 338 may be electronically operated and therefore opened and closed by UAV Computing System 323. However, both reversing the direction of UAV Extending Arms 336 and opening UAV Valve 338 may be mechanically performed and this is commonly done in many mechanical apparatuses.

In some cases, an entity providing shipping services may use a third party, i.e. a separate entity for the "last mile" of Pick up. In other words, Pick-up/Delivery Agent 300 may not be under the control of Server 400 and the latter may not have sufficient details of information about Pick-up/Delivery Agent 300 to schedule a Pick up. In such a case, Server 400 negotiates Pick up Information 305 and especially Usage Role 270, Usage Rights 271, Usage Period 272 and Pick-up/Delivery Connection Information 301 directly with Pick-up/Delivery Agent 300, in addition to negotiating with Pod Owner 250. The exchange of messages and acceptance of proposed information is identical to that described earlier between Pod Owner 250 and Server 400.

In yet another variation, Pod Owner 250 may own an unmanned vehicle or may have access to such a vehicle provided by a third party such as a logistics company such as Third-Party Logistics Provider 104 or owner of a fleet of unmanned vehicles may own such a vehicle. If known to Pod Owner 250 from say past use and if available from a menu of choices, Pod Owner 250 may also include specific model of vehicle or specific vehicle for Pick up and subsequent Delivery. Pod Owner 250 may be a user recognized by Server 410 and may optionally be required to login. If not recognized as a user, Pod Owner 250 may be required to create an account and then login. Based on past use, at least one of Pick up Address 304, Pick up Information 305, Delivery Address 306, Delivery Information 307 and Pick-up/Delivery Payment 302 may already exist on Device Server 410 and those may not be sent once Pod Owner 250's identity is established by login.

Fifth Embodiment—Pick-Up/Delivery by Human Agent from a Pod

In this exemplary embodiment, Pod Owner 251 owns a Pod 200 and a Sender 102, Recipient 103, another Pod Owner 251a, Pod User 260, or other entity such as a Human, an E-Commerce Retailer, any merchant or Third-party Logistics Company wants to Deliver or Pick up a Package 101 and therefore sends a Message 110 requesting permission from Pod Owner 251 to deliver or pick up Package 101 from or to Pod 200 respectively. In the description below, Pod Owner 250 is described, but may be substituted by any of the other entities enumerated above and even by Pod 200 acting through Pod Computing System 204 or through a Server 400. Pod Owner 251 may also initiate the delivery or pick up process by sending a Message 110a. If Pod Owner 250 has not initiated Pick up or Delivery, Pod Owner 250 responds to Message 110a with a Message 110b providing more information as enumerated next. If a Pick up is scheduled here Pod Owner 251 provides a Pick-up Address 304, Pick up Information 305, including the identification information associated with the Pod 200, namely Pod UID 211, and a random code to unlock the Pod 200. If a Delivery is scheduled, Pick up Address 304 and Pick up Information 305 may be substituted by Delivery Address 306 and Delivery Information 307 respectively, and the rest of the information presumably remains the same. This random code is preferably (but not necessarily) unique to each transaction (pick up or Delivery) and is referred to as Pod Passcode 213. Some or all of this information may already be present in Pod Owner Device 251 or on a Server 400 owned, operated or subscribed to by Pod Owner 250. Pod Passcode 213 may also be generated by the Server 400 or by the Pod 200 or even on Pod Owner Device 251 either automatically or manually by Pod Owner 250. If not generated by Pod 200, the information particularly the Pod Passcode 213 must be synchronized between the Pod 200 and entity generating said Pod Passcode 213. Additional passcodes for example Pod Passcode 213a, may also be generated for specific Usage Rights 271 such as for turning on a heating or cooling element. The identification information, address, Pod Unlock Codes and other information is stored as Pick up Information 305 or Delivery Information 307 before being transmitted to the Delivery Agent 300.

In addition to the above information, information transmitted to Human Agent 310 may also contain any combination of Usage Role 270, Usage Rights 271, Usage Period 272 and Pick-up/Delivery Connection Information 301. Human Agent 310 replies to the above Message 110b with Message 110c which may contain an acceptance flag or an unchanged copy of the information from Message 110b implying acceptance of proposed information or it may respond with new information. These steps relating to Message 110b and 110c are the beginning of the process more fully described in "Message based Negotiation" and the rest of the process is not described here for the sake of brevity. At the end of said process, if there is apparently no fit in at least one of Usage Role 270, Usage Rights 271, Usage Period 272 and Pick-up/Delivery Connection Information 301 between the two entities the Delivery is cancelled. If, however, agreement is reached as described above by, for example, a return of a message with unchanged information from either Pod Owner 250 or Human Agent 310 the process proceeds to the next step.

In this embodiment, Human Agent 310 receives the negotiated information and navigates to the vicinity of the Pod 200. Human Agent 310 uses Human Agent Device 311 to then send Pod Passcode 213 to the Pod 200. In an example, Pod 200 contains a SIM card or equivalent, and Human Agent 310 can transmit the Pod Passcode 213 as an SMS to Pod 200, which may send an acknowledgement back to said Human Agent 310 and may additionally perform the task associated with said passcode. If the Pod 200 does not have a SIM card that may be evidenced by a lack of an appropriate response from the Pod 200, the Human Agent Device 311 transmits Pod Passcode 213 using a different technology or protocol (e.g. Wi-Fi, Bluetooth and others using FTP, HTTP and so on) until a Message is successfully transmitted as evidenced by an acknowledgement or by appropriate action being performed by Pod 200. Although the example illustrates the use of SMS first, any technology or protocol may be used first and subsequent attempts using different technologies/protocols can use any technology/protocol in any order. The first used technology or protocol may be programmed by default in Human Agent Device 311 and therefore may be stored in Human Agent Device Storage 314 or it may be saved externally as a configuration on a Server 400a, said configuration linked to at least one of the said device or to a login representing a specific Human Agent 310. to the Server 400, which in turn transmits Pod Passcode 213 to Pod 200 via Pod 200's connection to an External Network 105 or Local Network 106 (which in turn may be connected to External Network 105). In an alternate aspect, Human Agent Device 311 transmits Pod PassCode 213 to the Server 400, which in turn transmits Pod PassCode 213 to Pod 200 via Pod 200's connection to an External Network 104 (which may be through a Local Network 105).

Human Agent 310 may also use at least one of the Gross/Global Positioning System and Short-Range Positioning System to locate Pod 200, especially in situations where addresses are inaccurate or difficult to find. In this case Human Agent Device 311 receives inputs and computes at least an appropriate path and at least a location of Pod in the same way as other devices discussed in Gross/Global Positioning System and Short-Range Positioning System, but in this case Human Agent may provide inputs and perform actions that may serve to change the results of the said positioning systems.

Positioning Systems

Below description discloses a few exemplary methods and processes by which unmanned and manned vehicles may reach the desired location of Delivery or Pick up. The desired location is assumed to be a Pod 200 in this description but can also be a Direct Recipient 150. Also, the description uses a Delivery Scenario as an example, but the methods taught can be used for Pickups in exactly the same manner. Finally, the example of a UAV 320 use to deliver a Package 101 is illustrated, but may be applied to any Pick-up/Delivery Agent 300 unless repugnant to the context. Positioning systems are illustrated here as being used by a UAV 320 comprising UAV Computing System 322 using UAV Computing Application 323 in conjunction with signals received and transmitted through UAV Communication Module 325. In the examples, a Pod 200 is described but may apply to other delivery locations as well, for example, to a marked location in "First Embodiment—Pick up without Pod". The examples illustrated in this section of the present disclosure should not be taken to be limiting to those examples and must not be assumed to limit the present invention in any way.

Gross/Global Positioning System—used from the launch or home base or any current position of the Unmanned Aerial Vehicle 320 to within a few meters of the Pod 200 using commercial or free Global Positioning Systems and Satellites. The North American GPS is different from the Russian equivalent (GLONASS), the European equivalent (GALILEO), the Chinese equivalent (BeiDou-2), or other similar systems (e.g. GNSS) although for the purpose of the teachings in this invention all the referenced systems will function in the same manner.

Short Range Positioning System—used when the Unmanned Aerial Vehicle 320 has reached the vicinity of the Pod 200 but may not be close enough to use Local Precision. Positioning System and therefore rendered unable to deliver a Package 101. The Short-Range Positioning System is to be used as the GPS does not have sufficient accuracy to bring the Unmanned Aerial Vehicle 320 precisely to the Pod 200. Typical accuracy of GPS is currently in the range of 3.5 meters to 7.8 meters which may not be sufficient to read information from, for example, Pod Graphic 212. When this stage is completed, the Unmanned Aerial Vehicle 320 will be positioned close enough to the Pod 200 to read markings and codes and further position itself with further precision using Local Precision Positioning System.

Local Precision Positioning System—this is the final stage and essentially positions the Unmanned Aerial Vehicle 320 so that it can drop or pick up a package to or from Pod 200. Without this, a package to be delivered may fall partly or wholly outside the receptacle and packages to be picked up may not be able to be accommodated within UAV Package Handling Apparatus 330 when picking up.

Manual/Operator Assisted Positioning System—this can, in an exemplary aspect, be used as a fallback and any Pick-up/Delivery Agent 300 may switch to this mode either automatically or manually upon failure of one or more of the above positioning systems. Typically, a Remote Operator 375 (but also potentially a proximal operator within line-of-sight) operates the UAV 320 or UTV 350 and in some cases, uses associated cameras to correctly position said device/agent for pick up or delivery.

Preferably, systems are used in the above order to successively narrow the exact location where a Package 101 may be picked up or dropped off. For example, UAV 320 may use Gross/Global Positioning System (GPS) to attempt to reach a Pick-up Address or Delivery Address. However, the range of error that is typically found in a GPS system as noted above may result in UAV 320 reaching near such an address but not at the precise location where it can pick up or deliver Package 101. When Unmanned Aerial Vehicle 320 determines, based on matching its coordinates and those of Pod 200, that it has arrived at Pod 200, it switches to the next appropriate system. In the best-case scenario, it has arrived at precisely the final position i.e. it is in position to deposit Package 101 into Pod Receptacle 220 of Pod 200. However, if it determines that it has not yet reached the precise location to deposit Package 101 it attempts to move closer to actual and precise location using first Short-Range Positioning System (SRPS) and then Local Precision Positioning System (LPPS), or it may switch directly to LPPS. In order for LPPS to work, UAV 320 has to be within range to recognize certain markings on Pod 200 as taught in the description below for LPPS (usually within a few centimeters). If successful, it uses the methods and processes described in LPPS and delivers or picks up Package 101. In a typical case, it will not be able to switch directly from GPS to LPPS and it must use SRPS.

Below are described various embodiments of Positioning Systems using Pods as an example. However, the same processes can be used when Pick-up/Delivery Agent 300 is attempting to locate a PodBank 230. In this case, instead of Pod UID 211 and Pod Graphic 212, said Pick-up/Delivery Agent 300 would use PodBank UID 237 and PodBank Graphic 238 respectively. Similarly, other obvious substitutions can be made such as PodBank Communications Module 235 for Pod Communication Module 205 and so on. In an aspect, however, one exception can be taught for Local Precision Positioning System which is that in the final step of pick up or delivery to a Sub-Pod 240 which is part of PodBank 230, Sub-Pod Graphic 247 may be used and not PodBank Graphic 238.

More than one positioning system can be active at any given time. For example, while using SRPS, UAV 320 may overshoot the boundary of the SRPS and GPS may be used as a corrective measure. In another example, while using SRPS, UAV 320 may pass over and recognize image of Pod Graphic 212 (as described below in LPPS) and therefore enable LPPS to immediately position itself accurately. Other combinations of all four positioning systems are possible and the present descriptions should not be taken to be limiting in any way. Each of the positioning systems is now described in more detail below.

Positioning Systems—Gross/Global Positioning System

In an exemplary implementation, a Message 110 is transmitted from at least one of a Pod 200, Pod Owner 250, a Pod User 260, a Sender 102, and a Third-Party Logistics Company 104 to a Server 400 and then on to the Unmanned Aerial Vehicle 320 or Unmanned Terrestrial Vehicle 350 that is seeking the Pod 200 for Delivery or Pick up. Hereinafter we only refer to UAV 320 but the description can be taken to also include UTV 350 and other Pick-up/Delivery Agents 300 except where specifically disclosed to be inapplicable or repugnant to the context. Also, the example embodiment described herein refers to Pick up or Delivery to a Pod 200 but can be applied to all other forms of Pick up or Deliver in the present invention and the examples used should not be considered as limiting in any way.

In some cases, Message 110 may be transmitted directly to the Unmanned Aerial Vehicle 320. Message 110 may be encrypted and can include any or a combination of Pick up Address 304, Pick up Information 305, Delivery Address 306, Delivery Information 307, Pick-up/Delivery Connection Information 301 and any other information needed to facilitate Pick up or Delivery respectively. Pick up Information 305 or Delivery Information 307 may include, for example, GPS coordinates of the Pod 200 (based on the Address 306 and provided by a commercial or free GPS system), one or more three-dimensional arcs suggested for approach to Pod 200, at least a common protocol to establish communication between UAV 320 and Pod 200 information necessary at least to connect to a Local Network 106 on Pod 200 (such as SSID, password etc.), address of a server to communicate with as an alternate data source (as Pick-up/Delivery Connection Information 301), and so on. Additional data may be included but is not described here unless relevant to the present example embodiment. Data relevant to other embodiments is included in the descriptions of those embodiments. For example, one or more patterns to be used for precision positioning of the Drone at the Pod 200 are also typically included in Message 110 but this is described in more detail under Local Precision Positioning System. UAV 320 can communicate initially through an External Network 105 with Pod 200, or it may communicate via a Server 400. Server 400 may also be a server enabled on Pod 200 by Pod Computing System 202, in which case we call it Server 410. Later, when it reaches a location proximal to Pod 200, i.e. within range of at least a Local Network 106, UAV 320 can connect more directly to Server 410 using for example a Local Network 106. UAV 320 can thus request and Pod 200 can provide updated GPS coordinates that are potentially more accurate than those provided by a general commercial GPS service. To do this UAV 320 sends a Message 110a requesting GPS coordinates and related information as described below; and Pod 200 responds with Message 110b. Pod 200 may send a multiplicity of Messages in response to Message 110a, for example if Message 110a has requested multiple updates at intervals. Each of the Messages may be decrypted (if encrypted), parsed and analyzed as needed and the information obtained used to increase accuracy of locating Pod 200. Commercial and free GPS systems today have varying levels of accuracy and this is determined at least in part by various environmental and atmospheric conditions (temperature, humidity, ionospheric activity etc.). The accuracy of the Pod 200 location as determined by GPS can be improved over time by determining and recording GPS location data at intervals as discrete data points and using statistical analyses on said data (for example, averaging the results plus throwing out outliers). Pod 200 stores said discrete data points and also includes, for each data point, one or more current environmental conditions that affect GPS location data (temperature, humidity, ionospheric activity etc. which may be obtained from the same GPS service, a different service or where possible from sensors in Pod 200 which are part of Pod Electro-Mechanical System 207) in Pod Data Storage 204. This may be stored preferably in a searchable database, but may also be stored as a flat XML or other file. When UAV 320 requests updated GPS coordinates, for example by sending a Message 110a, Pod 200 measures the current ambient temperature or humidity or any other measurable parameters and combining this with the provided GPS coordinates attempts to find matches in the database/file described above. If found, Pod 200 can send the matching data point to UAV 320 as Message 110b, and UAV 320 compares the information in Message 110b and may correct its coordinates sent in Message 110a by adopting the sent coordinates or averaging them with its own measurements. Further, UAV 320 may apply the correction to its new position if it has changed since sending Message 110a. This therefore may help UAV 320 to find Pod 200 more accurately and more quickly.

In an exemplary implementation, the present disclosure further relates to a static device that records at least one of its physical coordinates and physical coordinates of a multiplicity of mobile devices under different environmental conditions, stores such coordinates as stored data such that when requested to provide such coordinates, the device can provide coordinates that match the current environmental conditions as derived from stored data. The physical coordinates can include, but are not limited to, a combination of latitude, longitude and height, a combination of a distance and direction from emitters external (configured on requesting device) to the device, a combination of a distance and direction from emitters internal to the device. In an aspect, the distances are calculated based on strength of signals of the emitters received by the requesting device.

Positioning Systems—Short Range Positioning System

As described above, when UAV 320 determines that its Gross/Global Positioning System has brought UAV 320 to at least its approximate destination but UAV 320 is not within range of Local Precision Positioning (determined for example by UAV 320's inability to find Pod Graphic 212 or other means of using Local Precision Positioning System), Short Range Positioning System can be implemented. At this juncture, UAV 320 can establish a Local Network 106 or continue communicating with Pod 200 through External Network 105 and when successful, UAV 320 may send a Message 110 to Pod 200 requesting more positioning information. Pod 200 intermittently calculates its position by triangulating existing Wi-Fi, Bluetooth and other signals in the vicinity. This information, including the Pod's own position as well as relative locations, types (Wi-Fi, Bluetooth etc.), directions of the other signals (relative to that of the Pod) and identification of the signals (e.g. the SSID or device name) is transmitted to the Unmanned Aerial Vehicle 320 as Message 110a, which calculates its own position using the same techniques and information—or example, it may use the same SSID/device names as Pod 200. Further, in Message 110a, Pod 200 also communicates its current coordinates which it has received by using for example a commercial GPS system. UAV 320 of course knows its own coordinates and as taught above may also calculate its position by triangulating existing Wi-Fi, Bluetooth and other signals in the vicinity in the same manner as Pod 200 has done. Now comparing the vector difference between the GPS coordinates of Pod 200 with those calculated from proximal signals by Pod 200 and sent in Message 110a, UAV 320 can apply this difference to its own calculated coordinates (i.e. those derived from proximal signals), thus enabling UAV 320 to more accurately calculate its position and move towards its final destination namely Pod 200.

In another aspect, UAV 320 finds Pod 200 by triangulating signals from Pod 200. As disclosed under Gross/Global Positioning System, UAV 320 has received a Message now called Message 110b that contains Pick-up/Delivery Connection Information 301, the latter including at least one protocol (such as Wi-Fi, Bluetooth and others), network ID (such as an SSID), password and any other information needed to create a connection and thereby establish a Local Network 106, said Local Network including the target Pod 200. Also, as disclosed above, UAV 320 has used GPS coordinates of Pod 200 in order to move to a more favorable location i.e. closer to Pod 200. Since GPS systems typically have an accuracy of approximately 7 meters UAV 320 searches for the said Network ID using the said protocol transmitted in Message 110b and attempts to connect to Pod Communication Module 205 when its location appears to be within that range (or any other appropriate range as saved in its configuration as being the accuracy level of the GPS system being used) of the Pod 200. Until Pod 200 is located, UAV 320 flies in certain pre-defined (for example in widening circles i.e. a spiral) as well as random patterns created by or saved in UAV Computing System 322 as well as Delivery Information 307 (including three dimensional arcs suggested for approach in Message 110). While traversing the space where the Pod 200 is believed to be, UAV 320 stores significant locations in UAV Data Storage 324, such locations being for example, when it first acquires the signal for Pod 200, when signal is strongest, or when signal is lost. UAV 320 may also save intermediate locations and corresponding signal strengths. From this data, and using commonly known algorithms and graphical techniques, it extrapolates at least one linear equation representing a vector, said vector pointing to the Pod 200. In one example of such a method, circles passing through points of equal signal strength are drawn (three such points can establish a circle) and the centers of these circles (which will be found to be at least approximately concentric) can be computed and averaged; coordinates derived from said computation will be the location of the signal, and therefore also the location of the Pod 200. Thus UAV 320 can locate Pod 200 and moves to said location.

In yet another aspect of the Short-Range Positioning System, UAV 320 may use the Doppler principle to determine direction to or away from Pod 200 and thence, by triangulation, location, of the source of a signal in order to more accurately determine location of Pod 200. In this aspect, UAV 320 may know the natural frequency or wavelength of the signal transmitted by Pod 200 (based on standards, for example, IEEE 802.11g typically uses 2.4 GHz) or may measure said frequency or wavelength when not moving. When moving said UAV 320 measure frequencies at intervals and using this data in conjunction with well-known "Doppler Effect Equations" can calculate its direction (and optionally speed) in relation to Pod 200.

Pod 200 can also use Wi-Fi, Bluetooth, sound waves in the human hearing spectrum or beyond, light, laser, radar, sonar, infrared or any other technology to broadcast its location. UAV 320 has received in Pick-up/Delivery Connection Information 301 the protocol to be used and uses said protocol, but may negotiate a different protocol as described in "Message based Negotiation". Once a common protocol is negotiated, UAV 320 uses said protocol to locate Pod 200 and move to it. In an aspect, if unable to locate said Pod 200, using said protocol, it may send a Message 110c suggesting a different protocol and again, as described under "Message based Negotiation" using iterative messages can negotiate a different protocol and then use said new protocol to locate Pod 200.

In one aspect, UAV 320 may use, separately or simultaneously with other methods UAV Cameras (one or both or UAV Camera A 333/UAV Camera B 334) while in the range of other Short-Range Positioning System methods to search for Pod Graphic 212. If environmental conditions are conducive (sufficient light, clarity of atmosphere) and if said UAV Cameras are sufficiently powerful, UAV 320 may record and analyze images of the environment and using one or more image recognition algorithms, recognize Pod Graphic 212 and thus locate Pod 200.

In all aspects described above, UAV 320 (or any mobile Pick-up/Delivery Agent 300 as appropriate) uses Short Range Positioning System to locate Pod 200 and then moves toward it. Presumably UAV 320 is enabled with a collision detection/avoidance system (said system being outside the scope of the teachings of this invention) which allows it to come close to said Pod 200 without colliding with it. When it has reached a steady state, i.e. it cannot move closer to the Pod 200 without colliding with it, the usefulness of Short Range Positioning System ends and UAV 320 may proceed to the next step (typically Local Precision Positioning System).

Pod Owners can also participate in triangulation process by allowing the server or other pods to activate beacons in their pod. They benefit when their pod is being triangulated and other pods participate. Of course, this is only possible in high density Pod installations. One can also use different protocols (first Wi-Fi, then Bluetooth, followed by FC and so on in decreasing range protocols) because they have differing signal strengths.

Positioning Systems—Local Precision Positioning System

As described under Short Range Positioning Systems, Unmanned Aerial Vehicle 320 locates Pod 200 and positions itself near said Pod 200; however, UAV 320 may not be accurately positioned to accurately pick up or deliver a package to the Pod 200. In this next stage of Pick up or Delivery, UAV 320 is to be positioned at a more precise location near or over an appropriate receptacle in order to facilitate accurate pick up or delivery of a package and the methods described are now called Local Precision Positioning System. Below are described three embodiments of said system.

In each of the embodiments, a surface of the Pod 200 contains a pattern known as Pod Graphic 212. Pod Graphic 212 has previously been transmitted to UAV 320 in the process of scheduling a Pick up or a Delivery and is therefore known to the Unmanned Aerial Vehicle 320. Further, one or more cameras (such as UAV Camera A 333 and UAV Camera B 334) is capable of recording and UAV Computing System 322 is capable of recognizing the Pod Graphic 212. In the description, this is shortened for the sake of brevity to UAV 320 recognizing said pattern.

Further, UAV 320 attempts to match the recorded image with the image stored in UAV 320 (UAV Data Storage 324). UAV Computing System 322 may use any well-known pattern matching algorithms (these are already known to persons versed in the art and not taught in this invention) to compare the two images and may further send commands to the UAV Mechanical System 327 to change its location to better align UAV 320 with Pod Graphic 212. After each such movement, UAV Camera A 333 or B 334 may record at least an additional image and again compare it to stored image, followed by a further correction. In this manner UAV 320 can be positioned very precisely over Pod Graphic 212. Pod Graphic 212 has been located in such a manner that UAV 320 is in the most appropriate position to Pick up or Deliver a package.

In a first embodiment of LPPS, Unmanned Aerial Vehicle 320 is positioned above the Pod 200 and the top surface of the Pod 200 comprises Pod Graphic 212. In such a case, the top surface will preferably retract or open and expose a package for Pick up or a Pod Receptacle 220 for delivery.

In a second embodiment of LPPS, Pod Graphic 212 may be on any visible surface of Pod 200 and UAV 320 positions itself in alignment with Pod Graphic 212. UAV 320 then unlocks Pod 200, revealing a Pod Receptacle 220 and preferably sliding out a surface. Said surface holds a package for Pick up or if empty, can receive a package.

In a third embodiment of LPPS, there is no pattern on the surface of Pod 200 or UAV 320 is unable to find said surface. However, UAV 320 unlocks Pod 200, revealing a Pod Receptacle 220 and sliding out a surface. The horizontal surface of the drawer comprises Pod Graphic 212. UAV 320 then circumambulates Pod 200 until it finds said pattern. Unmanned Vehicle 320 then moves to position itself over the said pattern.

In one aspect, when applying these embodiments to a PodBank 230, instead of Pod Graphic 212, Sub-Pod Graphic 247 may be used for LPPS so that a Package 101 may be deposited into or picked up from the correct Sub-Pod 240.

It should be noted that although it has been described that Pod Graphic 212 is used for recognizing correct Pod 200, in LPPS, it may be used at any time given sufficient visibility. As an example, Pod Graphic 212 may be recognized from a distance that is normally ascribed to Short Range Positioning System, given sufficient environmental clarity and more powerful Cameras attached to UAV 320.

Manual/Operator Assisted Positioning System

In another embodiment, in case positioning during any of the three previously described positioning systems namely Gross/Global Positioning System, Short Range Positioning System and Local Precision Positioning System fails and UAV 320 is unable to locate Pod 200, UAV 320 can send a Message 110 to an operator, either directly if operator contact information is available or through Server 400, based on which Manual/Operator Assisted Positioning is performed by the Remote Operator 375 using at least one of UAV Camera A 333 and UAV Camera B 334 to view the location of the Unmanned Aerial Vehicle 320, location of the Pod 200 and the environment, said viewing an aid in subsequent control and operation of UAV 320. The operator can then let the Unmanned Aerial Vehicle 320 move to the Pod 200 or use remote controls to move or to assist Unmanned Aerial Vehicle 320. Operator assistance can be used in all of the three previously described positioning systems and control may be passed between the Unmanned Aerial Vehicle 320 and the Operator and back at any time for example by Operator taking or relinquishing control.

Step of Setting Up a Pod

In an aspect, when Pod Owner 250 receives a Pod 200 for the first time, the Pod Owner may need to physically assemble and secure said Pod 200. User connects Pod 200 to an electrical outlet so that it boots i.e. powers up and starts all necessary processes such as Pod Computing System 202 and Pod Computing Application 203. Next, Pod Computing Application 203 and Pod Owner Device Computing Application 253 must be configured in such a manner that Pod Owner 250 can securely control Pod 200 and no one else can, unless authorized by Pod Owner 250. Pod Owner 250 should be able to authorize and de-authorize users, allowing varying degrees of access (described later under Authorization and Delegation). To do this, a link is to be established between Pod Owner Device Computing System 252 and Pod Computing System 202 as described next.

Preferably Pod Communication Module 205, comprises at least Wi-Fi, Bluetooth or equivalent technology to create an Access Point or functionally equivalent resource preferably in conjunction with Pod Computing System 202; then as soon as Pod 200 starts up the first time, it is configured to be in Access Point mode so that Pod Owner Device 251 can connect to it. The ex-factory SSID of the Access Point as well as its password can be set to be the Pod UID 211 so that Pod Owner 250 can easily recognize it and connect to it. This prevents confusion when multiple Pod 200s are within the range of Pod Owner Device 251. Thus, Pod 200 and Pod Owner Device 251 are connected to each other through a Local Network 106. Pod Owner Device 251 has presumably been connected to Pod Owner 250's own home network, for example using a Wi-Fi or LAN connection, now called Local Network 106 which is associated with an Internet connection i.e. External Network 105. Alternately, Pod Owner Device 251 may connect to the public telecommunications network (for example using internet connectivity via GPRS) and thus create an External Network 105. Also, Pod Owner Device 251 may have saved the credentials for connecting to Local Network 106 in Pod Owner Device Data Storage 254. Pod Owner Device 251 can therefore provide these credentials to Pod 200 so that in the future, Pod 200 can connect to the Local Network 106 and hence to an External Network 105 such as the Internet. Pod Owner Device 251 and Pod 200 can be connected to more than one External Networks 105.

If connectivity through a Local Network 106 fails, or if the Pod Owner chooses an option in Pod Owner Device Computing Application 253 that disallows such connections, Pod 200 attempts to connect through the SIM (GPRS) to the Internet, thus creating an External Network 105. Pod Owner Device 251 is also enabled to connect to an External Network 105a which may be the same as External Network 105. Pod Owner 250 may configure Pod 200 so that it remains in Access Point mode, by which is meant it can allow connections from other devices that are enabled and can connect if the SSID and password of Local Network 106 set up on Pod 200 is known, for example when shared by Pod Owner 250 either directly or through, for example a Server 400. Pod Computing System 203 can shut off this Access Point mode when delivery is not expected and may automatically turn on this mode when Pick up or Delivery is expected or turn it on intermittently to check for status changes on Pick up or Delivery. Or Access Point mode may be manually turned on/off as needed by Pod Owner 250. Pod Owner 250 can turn on or turn off Access Point mode (and other features or services on Pod 200) after service is configured and Pod 200 and one or more Pod Owner Device 251 are connected to each other. In an aspect, Pod 200 connects to a general Access Point (for example a home Wi-Fi router) or to an Access Point on another device (for example Pod Owner Device 251).

As taught under System Architecture, Pod 200 has a unique ID which uniquely represents Pod 200, namely Pod UID 211 and is configured in Pod 200 typically before shipping to the customer (e.g. saved in Pod Data Storage 204). Pod UID 211 may also be displayed as Pod Graphic 212 and Pod Owner 250 can read Pod Graphic 212 and enter it into the Pod Owner Device Computing Application 253.

Pod Owner 250 may also scan Pod Graphic 212 if it is a bar code or QR Code or similar code or image using a camera or scanner built into Pod Owner Device 251 to do so. In some cases, manufacturer or supplier of Pod 200 may also send Pod UID 211 electronically, for example by email or SMS to Pod Owner 251. In such a case Pod UID 211 can be read into Pod Owner Device Computing Application 253 by using copy and paste or by an API for the email or SMS program respectively.

As also taught earlier under System Architecture, Message Encryption/Decryption Information 111 saved in Pod 200 contains keys, algorithms and combinations of keys and algorithms that can be used to encrypt and decrypt messages. Message Encryption/Decryption Information 111 has already been programmed into Pod Computing System 202 (and saved in Pod Data Storage 204) previously by manufacturer or supplier of Pod 200, or another entity who has been authorized by manufacturer, supplier or Pod Owner 250 to do so. Manufacturer or supplier of Pod 200 may also send Message Encryption/Decryption Information 111a (or a link to download the said information) that is complementary to Message Encryption/Decryption Information 111 as a Message 110 to Pod Owner 250. Thus, Message 110 may be an email confirming a Pod 200 order as an example, and contains Pod UID 211 and matching Message Encryption/Decryption Information 111a. Message 110 may be sent directly to the Pod Owner Device Computing Application 253 as a proprietary message using any protocol, or Pod Owner Device Computing Application 253 may request such a message from a Server 400 managed, operated or owned for example by Pod 200 manufacturer or supplier. Message 110 may also be sent as an SMS, by file transfer or by any other method, and the method of sending is not limiting in any way.

In a method, Pod Owner Device 251 includes Pod UID 211 as Pod UID 211a in Message 110a that can be sent in a plain unencrypted form. In a second method, Message 110 can be encrypted by Pod Owner Device Computing Application 253 so that it can be decrypted only by using Pod UID 211, preferably as a key. When Pod 200 receives Message 110a and is unable to interpret it, Pod 200 attempts to decrypt said Message using Pod UID 211. In a third method, Pod Owner Device 251 includes Pod UID 211 in Message 110a and encrypts said message using Message Encryption/Decryption Information 111a. When Message 110 is received by Pod 200 it attempts to decrypt said message using Pod UID 211 or Message Encryption/Decryption Information 110. If either is successful it retrieves Pod UID 211a from the decrypted portion of said message and then compares it to Pod UID 211 saved in its own Pod Data Storage 204. If they are the same the two devices are considered authenticated, otherwise Message 110 is discarded and Pod 200 remains unauthenticated to Pod Owner 250. In a fourth method, Pod UID 211 is not included in Message 110 but if at least a portion of Message 110 is encrypted by Pod Owner Device 251 and Pod 200 is capable of decrypting said message, said decryption providing Pod Owner Device 251 information listed above. Again, if said decrypted information is recognized by Pod 200 i.e. it is in the correct format and data can be validated by simple rules (e.g. phone number retrieved is a valid phone number), authentication is considered successful.

If authentication is successful, Pod 200 returns a success Message 110a to Pod Owner Device Computing System 252 and on receipt by Pod Owner Device 251 the two devices are now considered registered to each other. As described under System Architecture, Pod Owner 250 may have a multiplicity of Pod Owner Devices 251, and in this case, Pod Owner Device 251 that has been authenticated may contact other Pod Owner Devices 251a, 251b and so on, using previously configured authentication between these devices to synchronize Pod 200 information. In an aspect, Pod Owner 250 may manually perform the above functions. Further, information about these other devices can be sent to Pod 200 so that they can also be authenticated without having to directly interact with Pod 200 or Pod Owner Device 251, or they may each go through the process described above to be individually authenticated to Pod 200. Additionally, as described under Authorization and Delegation, other devices used for example by one or more Pod User 260 may also be authenticated to Pod 200 by Pod Owner Device 251, but will preferably have different levels of access than Pod Owner Device 251.

In any of the aspects, once a connection has been established and data and preferably encryption information has been exchanged between Pod 200 and Pod Owner Device 251 (as further elaborated below), the connection becomes persistent and in a preferable aspect, each device does not have to exchange passwords or force a login and further it is taught that messages are automatically synchronized as described elsewhere in this disclosure under "Synchronized Communication".

Now described are methods to achieve sending of messages described above. As described, Message 110 and subsequent Messages 110a, 110b and so on as needed can be sent using any technology or protocol that is conducive to sending messages. Taking the example of communication by SMS only, Pod Owner Device 251 initiates communication as described above by sending Message 110. Message 110 has been composed and preferably encrypted by Pod Owner Device Computing Application 253, and may be sent as SMS by Pod Owner Device Computing Application 253 or via a dedicated SMS application present on Pod Owner Device 251. SMS is processed using one of the methods described earlier in this portion of the description and thus the two devices are authenticated when successfully completed and not authenticated in case the methods fail. In case Pod Owner Device 251 does not have the capability to host Pod Owner Device Computing Application 253 (for example said device is not a Smartphone but a Feature Phone), SMS will not be encrypted and will have to be manually composed by Pod Owner 250. In this case Pod Owner 250 may send Message 110 as SMS to Pod 200 and a portion of Message 110 should include Pod UID 211, and if sent as multiple messages, preferably the first message should include Pod UID 211. Pod 200 recognizes Pod Owner Device 251 phone number using, for example, Caller ID. This may be sufficient to authenticate Pod Owner Device 251 with Pod 200, but in additional step, Pod Owner 250 may send an SMS containing at least a portion of Message Encryption/Decryption Information 111a received by Pod Owner 250. Pod 200 may compare said information that matches information in Message Encryption/Decryption Information 111 stored in its own memory i.e. Pod Data Storage 204. If a match is found, the two devices are authenticated.

In the embodiment where Wi-Fi is used to send the Message 110, it is disclosed that Pod Computing Application 203 enables a Device Server 410, such as an FTP server, HTTP server, Messaging Server or any other server capable of receiving messages from devices connected to Pod Communication Module 205 via W-Fi. Using the example of an FTP server, Message 110 may be uploaded as a file to the FTP intake directory which is periodically monitored by another process that is part of Pod Computing Application 203 and when file upload is complete, said process reads the uploaded file and interprets it according to the methods described above. Similarly, an HTTP server can allow upload of a file, but preferably if HTTP is used, Pod Owner Device 251 sends a command such as a GET or POST request, but any other format or method may be used including REST, SOAP, JSON, and so on. Similarly, an FTP or other server forms can be used with Bluetooth, or any other technology. A practitioner of the art will appreciate that any type of server running as part of Pod Computing Application 203 is capable of receiving Message 110 once a connection is established using lower level protocols, whether Wi-Fi, Bluetooth or others, and any generally available application or even a proprietary application is capable of fulfilling the role of the server. Thus, the underlying protocols are not to be taken as limiting to this invention in any manner.

Pod 200 has deciphered and/or decrypted Message 110, and now it parses the information contained in it and saves it in Pod Data Storage 204. In both Pod 200 and Pod Owner Device 251, this information may be stored in a database, XML file or any other format that makes it conducive to easy retrieval. Now that Pod 200 and Pod Owner Device 251 are authenticated, instructions from Pod Owner Device Computing Application 253 will now be performed by Pod Computing System 202, but the same instruction from a different Pod Owner Device Computing Application 253a from a different Pod Owner Device 251a will be ignored. For example, if Pod Owner Device Computing Application 253 were to send a Message 110b to Pod Computing System 202, said Message 110b comprising a request to unlock Pod 200, Pod 200 would be unlocked (preferably without a requirement for authentication), but an identical Message 110c from a different Pod Owner Device 251 will be ignored.

As described above, both devices have, stored in their respective Data Storage, certain algorithms and keys, together used for encrypting and decrypting messages sent between these two devices or to other components of Pick-up and Delivery System 100, and previously named Message Encryption/Decryption Information 111. Pod Owner Device Computing Application 253 may also generate a key or choose from an existing set of stored keys, and then also chooses at least an encryption algorithm from the list of algorithms in the system. Further, keys and algorithms may be obtained from a Server 400 to which the Pod 200 or Pod Owner Device 251 may connect, for example using an External Network 105 and which may be operated by Pod 200 manufacturer, Pod Owner 250, a third-party provider of keys and algorithms or any other entity. Location of at least one such Server 400 saved as a Fully Qualified Domain Name (FQDN) or IP address or other means of identifying and locating a server plus authentication information if required to obtain additional Message Encryption/Decryption Information 111 are also saved in Message Encryption/Decryption Information 111 in Pod 200. Also included in Message Encryption/Decryption Information 111 are means of locating additional such Servers and authentication information if required to obtain additional Message Encryption/Decryption Information 111. At intervals, Pod Owner Device Computing Application 253 transmits the combination of key and algorithm chosen to Pod Computing System 202 as Message 110d. Henceforth, any messages that pass between these two devices may be encrypted with this key/algorithm combination. Later, Pod Owner Device Computing Application 253 transmits a different combination of key and algorithm to Pod Computing System 202 in another Message 110b. Message 110b may be encrypted in the first key/algorithm combination, but can be decrypted by Pod Computing System 202 and includes an instruction to Pod Computing System 202 to use the new key/algorithm combination. Pod Computing System 202 decrypts the message using the first key/algorithm combination and then may acknowledge Message 110b with a Message 110c, the latter being encrypted with the new key/algorithm combination thus making an acknowledgement. At intervals randomly calculated by Pod Owner Device Computing Application 253 based on time, a number of deliveries or any other marker or any combination of these, or when initiated by Pod Owner 250, such new key/algorithm combinations may be sent by Pod Owner Device Computing Application 253 and each combination is used to encrypt and decrypt all communication between devices until it is changed again. Thus, security is considerably enhanced because constantly changing keys and algorithms greatly reduce the possibility of a current combination of keys and algorithms from being discovered and the system therefore effectively secures communication between devices. In another aspect, such new key/algorithm combinations may be sent by and/or initiated by a Server 400.

It is to be noted that Pod Owner 250 may provide minimum information at the time of initial setup, but detailed information such as address, preferences, online eCommerce accounts may be requested later and this can be filled out on Pod Owner Device Computing Application 253 or, for example, on a website using a computer. The detailed information is then associated with Pod Owner's record in a database. The Pod Owner 250 may also use Pod Owner Device Computing Application 253 to "name" the Pod. This name or even the Pod UID 211 can then be visible to devices as the Wi-Fi Access Point SSID or similar network IDs to facilitate visibility by humans or connections by various devices to the correct Pod 200. However as described elsewhere in this document, the network can be hidden to all but those devices that know the network ID.

Information about Pod 200 and/or Pod 200 configuration may be stored in Pod Storage 204 as well as Pod Owner Device Storage 254 and may be changed by Pod Owner 250 or by a person authorized by Pod Owner 250. Pod 200 contacts Pod Owner Device 251 at intervals to synchronize configuration information or Pod Owner Device 251 may send any configuration changes to Pod 200 automatically. For example, Pod 200 may be configured to execute a default command upon receipt of a voice call—for example to unlock the Pod 200 if locked or to lock it if unlocked. The default command may be changed by Pod Owner 250 by sending a Message 110 to Pod 200 or simply through an automatic synchronization process as described elsewhere under.

Figure 2E:
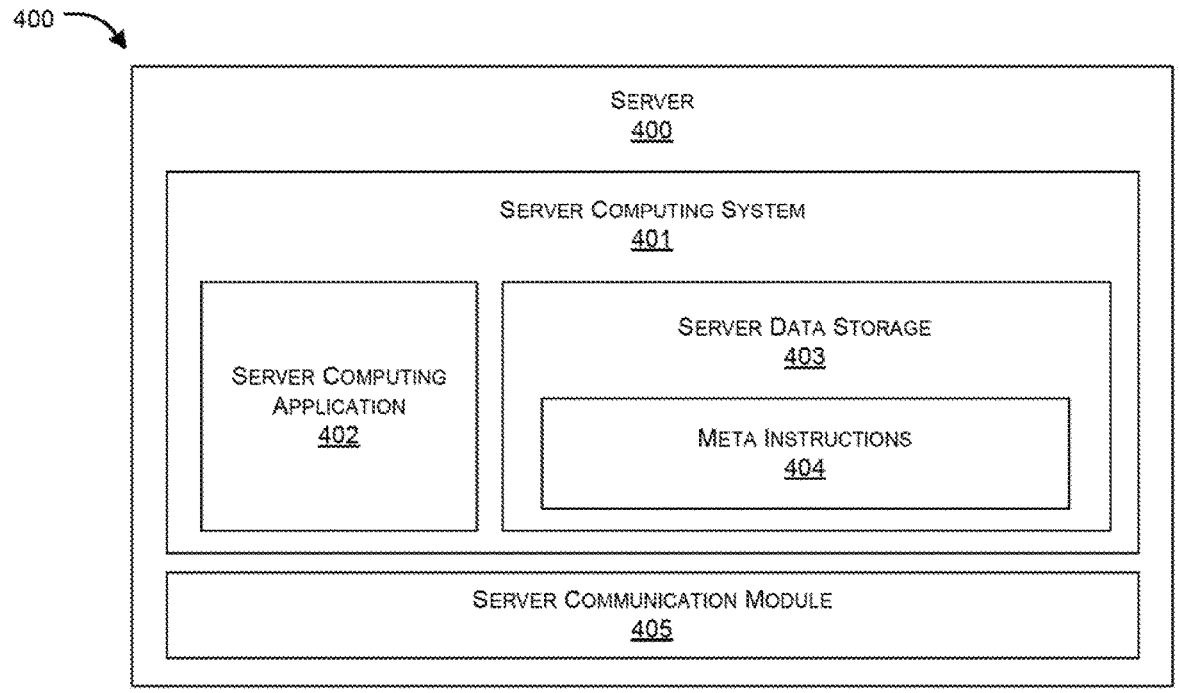
Figure 2F:
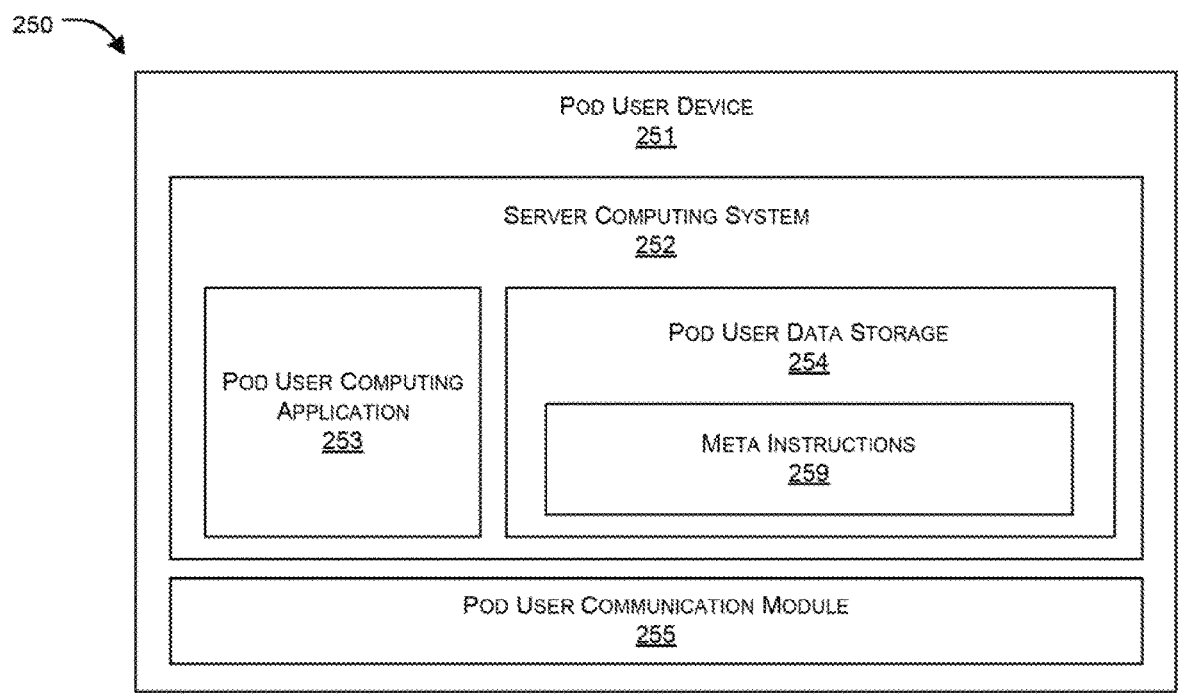
FIGS. 2F and 2G show two versions of Package Architecture
Figure 2G:
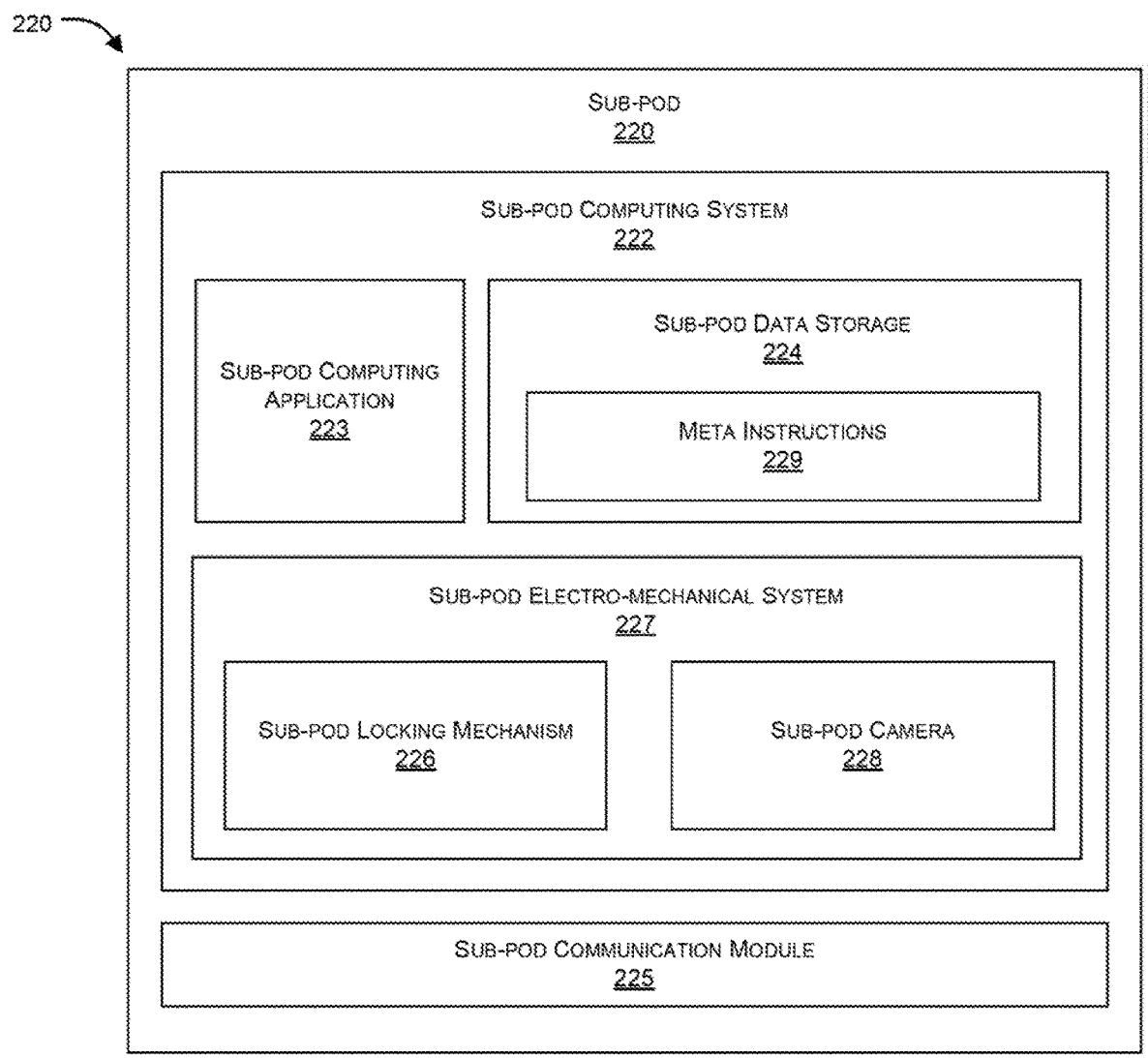

A system of setting up a Pod 200 and a Pod Owner Device 251 has been described wherein relevant information about both of the said devices is stored in respective data storage, i.e. identity information of both devices, Message Encryption/Decryption Information 111 and other information is stored in both Pod Data Storage 204 and Pod Owner Device Data Storage 254. Server 400 may further facilitate communication between the above devices as well as potentially, additional devices by receiving and forwarding messages as well as storing the said data in Server Data Storage 404 (FIG. 2E). During the exchange of information and registration process between the two devices, a copy of each Message 110, 110a, 110b and so on (including but not limited to messages containing keys/algorithms for encryption/decryption) may also be sent to Server 400 over External Network 105. Server 400 receives said messages over Server Communication Module 405 and stores the messages as appropriate in Server Data Storage 404. Before storing said messages, Server Computing System 402 may optionally decrypt the messages and may also interpret or parse them and store the interpreted/parsed information. The information thus saved may for example be associated with other data such as a Pod Owner 250 account and related details such as a delivery address, payment mechanisms and so on.

Information about Pod 200 and/or Pod 200 Configuration may be stored in Server Data Storage 404 and may be changed by Pod Owner 250 or by a person authorized by Pod Owner 250. Pod 200 contacts Server 400 at intervals to download new configuration information or Server 400 may send any configuration changes to Pod 200 automatically. Pod 200 may be configured to execute a default command upon receipt of a voice call—for example to unlock the Pod 200 if locked or to lock it if unlocked. The default command may be changed by Pod Owner 250 by sending a Message 110 to Pod 200 or by configuring an account related to Pod 200 on Server 400.

If successful using either network, i.e. Local Network 106 or External Network 105, Pod 200 registers itself on the server. The registration message(s) includes all relevant information such as its UID, IMEI, phone number, GPS location etc. Again, if a matching record for Pod Owner 250 with the same Pod UID 211 is found in Server Data Storage 404, Pod 200 and Pod Owner 250 are considered registered and authenticated. Now Pod 200 will only accept commands from one or more registered Pod Owner Device 251.

The message(s) may also include configuration information. For example, if it does not have a SIM card, and connectivity is through Wi-Fi, it includes that information in the message as well. If it has SMS connectivity, but not Internet Connectivity, it registers by sending one or more SMS's with the relevant information to an SMS gateway connected to the server. At this time or at a later time, the Pod may also send its GPS coordinates, Model number, size, weight capacity and so on. Example of data that can be sent to the Server 400 is shown below:

UID: 123E-P102-1Z131-2ME9
Number: +14083357664
IMEI: 3294982498202
GPS: Latitude: 43.038903|Longitude: −87.906474|187
Name: Dimding
Model: P16A Once registration is completed, Pod Owner 250 may also use Pod Owner Device Computing Application 253 or some version of it, either on Pod Owner Device 251 or any other capable computing device to allow multiple users (e.g. other family members) to be able to operate Pod 200 thus creating additional Pod Owners 140 or Pod Users 260 as described previously under System Architecture and also in section Authorization and Delegation.

Thus, the two devices Pod 200 and Pod Owner Device 251 are registered and the information about such registration may be saved in a multiplicity of places, including but not limited to Pod Data Storage 204, Pod Owner Device Data Storage 254, Server Data Storage 404, Device Server Data Storage 404, or Pod User Device Data Storage 264 (in an embodiment described elsewhere in this description).

Exemplary Steps in Operating a Pod

Pod 200 and Pod Owner Device 251 have been configured and Pod 200 and Pod Owner 250 have been authenticated and registered to each other as described under "Step of Setting up a Pod". Therefore, Pod Owner 250 is capable of sending messages to operate Pod 200 including, for example requesting information from sensors in Pod 200, operating heating/cooling elements or other features, and locking/unlocking Pod 200 remotely (via External Network 105) or from its vicinity (via Local Network 106) or for any activities related to Pick up, Delivery or Storage of a Package 101. Pod Owner 250 may also delegate certain actions to a Pick-up/Delivery Agent 300 or Pod User 260 or other entities that are capable and have rights to operate the Pod, for example the ability to lock or unlock Pod 200 or operate other features of Pod 200. Therefore, said entities are now capable of communicating with Pod 200 and also operating it like Pod Owner 250 within limitations based on Usage Role 270, Usage Rights 271 and Usage Period 272. If the process is to be applied to a different user such as Pod User 260, appropriate substitutions such as Pod User Device 261 instead of Pod Owner Device 251 should also be made. The examples below, describe unlocking a Pod 200 but are also illustrative of other processes, such as locking a Pod 200, operating Pod Electro-Mechanical System 207 for heating or cooling or other functions and so on. Turning to examples that illustrate the process of operating a Pod for various purposes, various illustrative methods of unlocking a Pod 200 are now taught. The present invention teaches that there are multiple ways to accomplish one or more of these operations, depending on the context of the task and also depending on the configurations available in Pod 200. Further, there are multiple ways of sending and receiving messages required to accomplish these tasks. A practitioner of the art will appreciate that the process can be extended either fully or in part to other entities that have the capability to perform any of the actions taught, and this will also depend on the rights accorded to that entity. For examples of rights available to operator see Section "Authorization and Delegation".

As has been taught elsewhere in the current disclosure, Sub-Pods 240 are functionally and structurally similar to Pod 200 and most operations ascribed to Pod 200 or performed to or with Pod 200 (here as well as elsewhere in this disclosure) can be identically performed with Sub-Pod 200. As explained earlier, Sub-Pod 240, in some cases can be converted into a Pod 200 when removed from PodBank 230. Thus, the current teaching and illustrative examples are assumed to also apply in their entirety to Sub-Pods 240 unless explicitly stated in the disclosure or repugnant to the context based on the understanding of a practitioner versed in the art.

In an example embodiment, Pod Owner 250 gets a Message 110 (via SMS/email/voice call or any other form or protocol) from a Pick-up/Delivery Agent 300 or from Sender 102/Recipient 103 informing Pod Owner 250 of relevant Pick-up/Delivery details including at least an identity information such as a phone number or device ID of the Pick-up/Delivery Agent 300. Message 110 may be received on Pod Owner Device 251 either directly or from a Server 400 operated by Sender 102/Recipient 103 or a third party such as a logistics company. The Pod Owner Device Computing Application 253 allows Pod Owner 250 to enter (including copy-paste) the Pick-up/Delivery Agent 300's identity information such as a phone number or select said identity information from, for example, at least one of a recent call list, SMS, notification, message using a messaging App (e.g. WhatsApp®, Viber®, SnapChat® etc.), a recent email, a file saved on the device, and any API or connector that it is capable of or programmed to interface with other systems such as a retailer's system. Pod Owner 250 can then send the phone number/ID of the Pick-up/Delivery Agent 300 to Pod 200 as a Message 110a including in said message Usage Role 270, Usage Rights 271 and Usage Period 272 if available. In an aspect, Pod 200 already has this information as Usage Role 270a, Usage Rights 271a and Usage Period 272a stored in Pod Data Storage 204 because Pick-up/ Delivery Agent 300 or preferably Server 400 has already sent this information to Pod 200. If information present on Pod 200 matches information in Message 110a, nothing needs to be done. If, however, there is any difference, preferably information sent by Pod Owner 250 replaces that which is locally stored.

Unlocking Example Use Case I—In this Use Case, Pod Communication Module 205 is not enabled with local network capabilities, because it may not have a related module (e.g. Wi-Fi or Bluetooth or other such module) to create a Local Network 106 or a Local Network 106 is unreachable. Alternately, Pod Owner 250 or Pick-up/Delivery Agent 300 or any potential operator of Pod 200 may not be enabled with the ability to use a Local Network 106 (e.g. not possessing a Smartphone or not having more sophisticated technologies such as Wi-Fi, Bluetooth etc. enabled on the phone/device), or may simply prefer not to use a Local Network 106. However, Pod Communication Module 205 may have a SIM card or a functional equivalent and is therefore enabled with access to the public telecommunications network now called External Network 105. Thus, it may be capable to send and receive SMS messages, and even make and receive voice calls. In this use case, Pod Owner 250 may send an SMS or make a voice call using a phone or any device with similar capabilities (including but not limited to a modem connected to a phone line and coupled to a computing device) to Pod 200. The SIM card in Pod Communication Module 205 may be configured for and capable to recognize a caller or SMS sender using for example "Caller ID". Thus, Pod 200 may be configured to only act on receipt of voice call or SMS from a number registered in Pod Data Storage 204 or as registered in an account related to Pod 200 on Server 400. Such a number may include that of one or more Pod Owner Devices 250 or other devices of users who have been granted access in Usage Role 270 or Usage Rights 271 during the time period represented by Usage Period 272. Pod 200 may be configured to execute a default command upon receipt of a voice call—for example to unlock the Pod 200 if locked. If said voice call is from a number not in a list of numbers associated with Usage Rights 270 in Pod Data Storage 204, the call is not answered at all. If the said number of the voice call is recognized however, the call is answered and Pod Computing Application 203 may also have a voice recognition module and can recognize commands spoken in the said voice call. At this time, Pod 200 also uses other logic such as comparisons with Usage Role 270 and Usage Period 272 to determine if Pod 200 will act on instructions associated with sender/caller.

Pod Owner 250 may also send an SMS as Message 110 and Pod 200 recognizes the number again using a form of "Caller ID". Pod 200 may execute said command if the number matches Pod Owner 250's number, but will not do so when the number provided by the Caller ID does not match the Pod Owner 250's number or is not included in a Usage Role 270 for example. Message 110 may contain one or more instructions—for example to unlock Pod 200 or to turn on heating or cooling apparatus in Pod Electro-Mechanical System 207. Message 110 sent by Pod Owner 250 or Server 400, may have been created in a typical SMS application found on most phones or it may be created by appropriate Computing Application. When created by a typical SMS application, it may be unencrypted, and the Pod Computing System 202 is capable to recognize this and not use a decryption method on Message 110 (See above under System Architecture for details on methods for handling encrypted and unencrypted messages).

Pod Owner 250 may also use Pod Owner Device Computing Application 253 to compose the SMS messages and thereby send commands to Pod 200. In this case, the Pod Owner 250 presses some combination of buttons or menu choices which identify a command to be sent to Pod 200. The Pod Owner Device Computing Application 253 then creates an appropriate Message 110 and sends this message as an SMS to Pod 200. When Message 110 is originated by Pod Owner Device Computing Application 253, it may be encrypted or not. If it is encrypted, when Pod 200 receives it, Pod Computing System 202 is capable of recognizing this and uses a decryption method on the message to decrypt it so it can be interpreted and acted on.

Unlocking Example Use Case II—In another use case, Pod 200 is connected to a Local Network 106, for example a home Wi-Fi network, which in turn may be connected to the Internet. Pod Owner 250 may be connected to the same Local Network 106, or to another Local Network 106a which is also connected to the Internet. Local Network 106a may be in another location, for example another city, or even another country. Pod Owner 250, using Pod Owner Device Computing Application 253 can send Message 110 to Pod 200 by connecting to Local Network 106 or Local Network 106a, and Message 110 is transmitted to Pod 200. Message can be sent for example by HTTP, FTP or any appropriate and configured protocol because Pod Computing System 202 has enabled a Device Server 410 (see System Architecture). Message 110 in this case is preferably encrypted with an algorithm and key, which are known to both Pod Computing Application 203 and Pod Owner Device Computing Application 253 as taught previously in this disclosure. Pod 200 therefore receives said message, parses it and acts upon the instructions embedded in it, for example to unlock the Pod 200.

Unlocking Example Use Case III—In this use case, Pick-up/Delivery Agent 300 includes a device that is enabled with a SIM card as part of its communication module. For example, Unmanned Aerial Vehicle 320 travelling to Pod 200 to pick up or deliver Package 101 may include a SIM card as part of UAV Communication Module 325. Pod Owner 250 can provide the phone number associated with the aforesaid SIM of Unmanned Aerial Vehicle 320 to Pod 200 along with parameters that specify a Usage Role 270, Usage Rights 271, Usage Period 272, Pick-up/ Delivery Connection Information 301 and any other relevant information. When UAV 320 is near Pod 200, it sends Message 110 to Pod 200 to unlock so that it can Pick up or Deliver Package 101. Alternately, Pick-up/Delivery Agent 300 (for example UAV 320) can initiate a call to Pod 200, which, as described earlier can also unlock Pod 200, if that is the default command. Thus, the present use case is identical to Unlocking Example Use Case I with one difference, namely, instead of an owner or user unlocking Pod 200, Pod Owner 250 (or a different user with rights to do so) has authorized a Pick-up/Delivery Agent 300 to unlock or operate said Pod 200 by sending Message 110 or voice call with UAV 320 phone number and other parameters to Pod 200 (See Authorization and Delegation for more). In this case, UAV 320 has received Pick-up/Delivery Connection Information 301 as well as Pick up Information or Delivery Information and Pod 200 has received corresponding information, thus allowing communication between the two entities independent of the Pod Owner 250. Note that although we illustrate this use case with UAV 320, it may also be performed by any Pick-up/Delivery Agent 300, including Human Agent 310, UTV 350 and so on in practically an identical process.

Unlocking Example Use Case IV—A potential operator may also use Wi-Fi or Bluetooth or similar technologies to operate Pod 200 and this use case is now illustrated again using Pod Owner 250 as an example. In this case, operator's device and Pod 200 are enabled with one or more technologies such as Wi-Fi and Bluetooth. For example, Pod Owner Device Communication Module 255 and Pod Communications Module 205 both have one or more of said modules. Pod Owner 250 selects a command from Pod Owner device 251 user interface, for example to unlock Pod 200. Pod Owner Device Computing Application 253 creates Message 110 incorporating this command and may also encrypt at least a portion of said message before sending it to Pod 200. If Pod Owner 250 is not in the vicinity of Pod 200 (i.e. within range of an appropriate signal), Pod Owner Device 251 cannot connect directly to Pod 200 and Message 110 is instead sent to a Server 400 operated by Pod Manufacturer/Supplier, Sender 102, Third Party Logistics Provider 104 or any other entity that owns or operates a server capable to perform the necessary tasks. Message 110 contains Pod UID 211 in an unencrypted portion of Message 110. Alternately, Server 400 is capable to decrypt Message 110 to extract Pod UID 211. Thus, Server 400 can determine from Message 110 the addressee of the said message i.e. Pod 200, and can forward it to said Pod 200 or store it in Server Storage 404 so that Pod 200 can retrieve it in its next synchronization. Message 110 may also include additional information and may include multiple commands in a single message. For example, Message 110 may include a command to unlock Pod 200, then turn on heating element of Pod Electro-Mechanical System 207 and may also include a time period for keeping it on and a temperature to be maintained. If Pod Owner 250 is in the vicinity of Pod 200, Pod Owner Device 251 can connect to Server 410 of Pod 200. Pod 200 Network ID (e.g. SSID) is stored in Pod Owner Device Storage 254 and it therefore known to Pod Owner Device 251. As described previously, Pod Communication Module 205 may have configured Wi-Fi or Bluetooth to switch between Access Point mode and Client mode and when Pod Owner Device 251 attempts to connect to Pod 200, latter may not be in Access Point mode, therefore Pod Owner Device 251 reattempts a connection until said connection is established. Once connection is established, Message 110 is transmitted to Pod 200 and decrypted by Pod Computing Application 203. As noted earlier in Section "Step of Setting up a Pod" and in System Architecture, Pod Owner Device 251 and Pod 200 share certain keys and algorithms that allow each to decrypt messages sent by the other. Once Message 110 is decrypted, Pod Computing Application 203 analyses it and executes commands included in said message.

Unlocking Example Use Case V—In this example, an operator such as a Pod Owner 250 calls or sends an SMS to a specific phone number (for example a toll-free number) to unlock Pod 200. Other operations (say turning on heating element of Pod Electro-Mechanical System 207) may be associated with other phone numbers. The receiving phone system can be managed by a Server 400 in which a phone number associated with Pod Owner 250 has been stored. Other operators' phone numbers (for example that of Pick-up/Delivery Agent 300) along with their associated Usage Rights 270 can also be added to said Server Data Storage 404 by Pod Owner 250 using Pod Owner Application 253.

In the case where an operator calls the number associated with unlocking, the receiving number recognizes the incoming number using Caller ID and sends said incoming number to Server Computing Application 403 which then searches Server Data Storage 404 for a matching Pod UID 211 and Usage Rights associated with Caller ID of incoming number. If a match is found, it executes the command to unlock the Pod 200 associated with said Pod UID 211. In another aspect, the SMS may contain a Pod UID 211 so that Pod Owner can specify a specific Pod 200 if said Pod Owner owns more than one Pod 200, Pod 200a and so on. In yet another aspect a single receiving number is envisioned and Server 400 is enabled with an Interactive Voice Response (IVR) system which allows operator to interact with Server 400 through the use of voice and (Dual-Tone Multi-Frequency) DTMF tones input via a keypad. Operator can then choose an operation to be performed (for example unlocking Pod 200) by selecting at least one of a menu of choices.

In the above examples and use cases, any process may be associated with a multiplicity of technologies and with a multiplicity of use cases described above. For example, Pod Owner 250 or Pick-up/Delivery Agent 300 may unlock using SMS but operate Pod Electro-Mechanical System 207 using Wi-Fi. Also, multiple entities may operate Pod 200 to complete a process. For example, Pod Owner 250 may unlock Pod 200 and Pick-up/Delivery Agent 300 may operate Pod Electro-Mechanical System 207 (or vice-versa) in the same delivery. The examples above use Pod Owner 250 to illustrate operations such as locking/unlocking or delegating to Pick-up/Delivery Agent 300 for example. However, all the above described may be performed by other entities such as a Pod User 260, if that Usage Role 270 permits the operation. It should be noted that the above examples are illustrative and show some examples of the working of the invention, and hence should not be seen as limiting the invention or its scope in any way.

Exemplary Sub-Pod Embodiments

As described under System Architecture above, PodBank 230 may include one or more Sub-Pods 240. Sub-Pod 240 can be capable of several operations; many of which are the same as Pod 200. For example, locking/unlocking including adherence to associated rules, such as Usage Roles 270, Usage Rights 271 and Usage Period 272 associated with one or more Pod Owners 250, Pod Users 260, Pick-up/Delivery Agents 300, and other entities. However, at least one additional operation can be performed on Sub-Pod 240, namely removing or detaching Sub-Pod 240 from PodBank 230. When any operation is to be performed on a Sub-Pod 240, a Message 110 must be sent to Sub-Pod 240, either directly, or through one of PodBank 230 and a Server 400.

Taking the example of unlocking Sub-Pod 240, PodBank Computing System 232 can authenticate an entity that has requested access to Sub-Pod 240 in the same manner as Pod Computing System 202 does when access is requested to Pod 200 i.e. as a Message 110. Message 110 may for example be in the form of an SMS sent to separate SIM module, which is part of PodBank Communication Module 235. When Message 110 is sent to PodBank 230, it may also contain a Sub-Pod UID 248 that uniquely identifies the Sub-Pod 240 that is to be operated on. Alternately PodBank Data Storage may hold said Sub-Pod UID 248 linked to an identity associated with that phone number or other identity associated with the device sending the communication. On receipt of a Message 110, PodBank Computing System 232 searches PodBank Data Storage 234 for the identity (for example, from the Caller ID of Message 110) of the sending device and a Usage Role 270 and a Sub-Pod 240 matching the phone number derived. PodBank Computing System 232 also searches for appropriate Message Encryption/Decryption Information 111 comprising at least a key and/or algorithm to decrypt said message. If decryption is successful or if Message 110 was not encrypted in the first place, it performs the command contained in the message or performs the default command associated with the Usage Role 270, for example unlocking Sub-Pod 240 and optionally opening a door, drawer or appropriate element of Sub-Pod 240. If identity information matching a potential user (based on device of sending identity or contents of decrypted message) is not found in PodBank Data Storage 234, PodBank Computing System 232 may reject or ignore said message. Note that if message is not encrypted and PodBank Computing System 232 cannot ascertain identity of sending device (for example through Caller ID), it rejects the Message 110.

In an aspect, the Sub-Pod can be an UAV 320 or a portion of a UAV 320 and can go to the merchant or individual to pick up the package.

Image Comparison for Determining Pod States

At intervals or at the request of a Pod Owner 250, Pod User 260, Pick-up/Delivery Agent 300 or any other entity authorized and capable of requesting the state of a Pod such as for example to determine if a Pod 200 is unoccupied and therefore available to receive a Package 101, Pod Computing Application 203 may be required to make such a determination and can do so using one or more image comparison methods. In these methods, Pod Computing Application 203 compares two images—one stored in Pod Data Storage 204 (Stored Image) and another retrieved by activating Pod Camera 208 and acquiring said image (Current Image) at the time a comparison is needed. In one exemplary embodiment of an image comparison method, the stored image includes at least the Pod Graphic 212 preferably on an inner surface of Pod 200 (including as appropriate on a Pod Receptacle 220 that is part of Pod 200) where said graphic is visible to the Pod Camera 208. As noted earlier, Pod Graphic 212 may include an appropriate image, barcode, QR code or other graphic or even alphanumeric characters. By processing Pod Graphic 212 against a software based QR Code reader (or bar code reader or other image processor as appropriate), Pod Computing Application 203 generates a string or unique ID representing the Pod 200. In some cases, this operation has been previously completed and string has been previously generated and further has been stored in a known location in Pod Data Storage 204. Pod Computing Application 203 then attempts to do the same for Pod Graphic 212 in the Current Image. If the string generated from this operation matches the string generated from the Stored Image, it can be deduced that Pod Graphic 212 is fully visible and that no Package 101 is blocking Pod Graphic 212 and the Pod 200 is empty. In case Pod Graphic 212 is a pure image, Pod Computing Application 203 simply stores the raw image as Stored Image and compares it to Current Image using any one of well-known image comparison techniques such as but not limited to one or more of Histogram comparison (color and texture based), Keypoint matching (based on Scale-Invariant Feature Transform or similar algorithms) and Decision Trees. In a second embodiment of an image comparison method, Pod Graphic is not present, not usable or ignored, but both Stored Image and Current Image are each images of the interior of Pod 200. Pod Computing Application 203 converts each image into vectors using well-known raster-to-vector algorithms. Any Package 101 in the Pod 200 will have its own edges and therefore Pod Computing Application will generate additional vectors from the raster outline of the Package 101. If the number of vectors from Stored Image and Current Image is identical it can again be deduced that the state of the interior of the Pod is unchanged in the two images and therefore the Pod 200 is unoccupied. Conversely if the number of vectors has increased, Pod Computing Application 203 can deduce and therefore report that Pod 200 is occupied. Pod Computing Application 203 can further compare the vectors for equivalence even if the number of vectors remains the same. In this case approximations are used since raster-to-vector conversions may result in minor errors. Vector direction is algebraically calculated and this is compared to the two matching vectors from the two respective images for equivalence. Vectors magnitudes here are rounded to a precision lower than the raster-to-vector conversion error and calculated vector directions are adjusted similarly. Such approximations are sufficient to deduce the presence or absence of a Package 101.

Authorization and Delegation

In an aspect, as can be seen in FIG. 7, Pod Owner 250 may assign various rights to operate Pod 200 to a multiplicity of Pod Owners 250, Pod Users 260, and Recipients 103 and these rights may even overlap. For example, Pod Owner 250 may allow a multiplicity of entities such as Recipient 103, Recipient 103a, Pod User 260, Pod User 260a, Pod User 260b, and so on to use Pod 200 for an interval of time and any conflicts of delivery are managed either manually or automated by software as described below. If, for example, Pod User 260 schedules a delivery during a particular time interval on a particular day, such information can be displayed to Pod Owner 250 who may manually approve such a request or may have configured Pod Owner Device Computing Application 253 to automatically approve such requests from either a specific user or from all users (subject to availability which can again be automatically checked by Pod Owner Device Computing Application 253). Once said request is approved, the Usage Period 272 can also be visible to Pod Users 260a and 260b on their respective devices. In this example, Pod Owner 250 and Pod Users 260a and 260b do not schedule, or are prevented (for example by Device Server 410 on Pod 200) from scheduling a delivery at the time blocked out by Pod User 260.

Assignment of rights i.e. authorization and delegation to use Pod 200 or any of its various features can be provided by negotiating one or more Usage Roles 270, Usage Rights 271 and Usage Periods 272 with Pod Owner 250 by any user interacting with Pod Owner Device Computing Application 253. Once negotiated, as described below, Pod Owner 250 may automatically or manually transmit said rights to Pod 200 where they may be saved, so that specific users who have been granted rights can interact with Pod 200 directly without Pod Owner 250 being present. All such roles, rights and periods may be saved in Pod Data Storage 204 as files, databases or any other format and made available to lookup when needed to allow user specific actions in relation to Pod 200.

Authority can be granted by an authorizer and requested by or granted to a requestor (called requestor even if authorization is initiated by authorizer). In an example, an entity such as an individual requests Pod Owner 250 for use of Pod 200 as Pod User 260. When a certain combination of rights is assigned to said entity, Pod User 260 is created. In this case, Pod Owner 250 is an authorizer and Pod User 260 is a requestor. Authorization of role or rights may be initiated by requestor or by authorizer. If requestor initiates the process and a related application is not used, authorizer may initiate the process of adding roles and rights of requestor. If initiated through a computing application associated with requestor, and this is a first request by the requestor, an identity may be created and sent as part of Message 110 to authorizer. Said identity can include any combination of a phone number, an email address, a user name, a device ID (of user device), an IMEI number, a MAC address or any other unique identification code. Identity can also include a password or other form of personal identification such as a fingerprint, voiceprint, retina scan or any other similar authentication device. If the request is not the first request, identity information may be sent with the message and serves to authenticate requestor. If an application is not used, authentication may use at least one of a phone number (obtained for example using caller id), login (such as user name, email etc.) and password that is sent in a Message 110.

In an example, Pod User 260 desires to use Pod 200 for a certain period of time in order to receive Package 101. Pod User 260 sends a request to Pod Owner 250 using any method including but not limited to email, SMS, voice (e.g. using a phone or face-to-face conversation) or preferably using Pod User Device 261. If such a request is received in a manner not automatically readable by Pod Owner Device 251, Pod Owner 250 must enter the details into Pod Owner Device Computing Application 253 using its interface. The interface may for example allow Pod Owner 250 to select a role or create a new role, optionally name it and then assign rights to that role. If request is created by Pod User Device Computing Application 263, the rights may have been selected already by Pod User 260. The request is received as a Message 110 and because it was created by Pod User Device Computing Application 263, it is conceivably in a format readable directly by Pod Owner Device Computing Application 253, and can therefore be presented to Pod Owner 250 in a format that Pod Owner 250 can validate in a single button press or can modify the role or any of the rights before validating. A similar interface is available in Pod User Computing Application 263 and the same steps can be followed to allow Pod User 260 to add another Pod User 260a and associated Usage Role 270, Usage Rights 271 and Usage Periods 272. Pod Owner 250 and Pod User 260 can use the same or a variant of above interface to modify existing roles and their associated rights.

In a simple exemplary and illustrative aspect, Pod Owner 250 sends a Message 110 in the form of an SMS to Pod 200 in the format "User 9999999999". This informs Pod 200 that a Pod User 260 who owns or operates Pod User Device 261 (which is identified by the phone number "9999999999") is authorized to perform commands associated with role of Pod User. In an aspect just sending the number is sufficient and Pod 200 computes that said number is to be receive default User Role 270. Any other word or symbol can be used in place of the word "User", and more complex commands can be used. For example, "User P 9999999999" can signify that the number is to be understood to be a phone number and "User L DeliveryPerson4" can signify that "DeliveryPerson4" is a login ID. Additionally, a password can be sent or can be generated by Pod 200. As described elsewhere in the present disclosure, Message 110 can be transmitted as a file, a signal, an HTTP request and so on and the present example is illustrative of a very simple use case of authorization/delegation.

A Pod Owner 250 may want to allow others to have equal rights to Pod 200. For example, Pod 200 is purchased for the use of a family and Pod Owner 250 may be a member of a family and configures rights to other members of her family as Pod Owner 250a, Pod Owner 250b and so on. In an exemplary embodiment, Pod Owner 250 gives Pod Owner 250a, Pod User 260 and others authority to accept pick up or delivery of packages to Pod 200, store packages in Pod 200 or pick up packages from Pod 200. The ability to perform such actions and any ordinarily associated actions, or those defined by business rules or practices associated by a business or a Pod Owner 250 have previously been designated Usage Rights 271. Said Usage Rights 271 are preferably authorized for a specific time period that is hereinafter designated as Usage Period 272. In some cases, Pod User 260 can sub-assign all or part of the said authorization to use Pod 200 to another Pod User 260a. For example, Pod User 260, who has received authorization to use Pod 200 for one specified twenty-four-hour period (Usage Period 272), can authorize a second Pod User 260a to use Pod 200 for four of those twenty-four hours.

A comprehensive example embodiment is shown as a table in FIG. 7. Shown therein are five example roles associated with unique rights, namely Create/Edit Pod Owners, Delete Pod Owners, Create/Edit Pod Users, Delete Pod Users created by others, Create/Edit Own Usage Period, Edit/Delete Others Usage Periods, Delegate Locking/Unlocking, and Lock/Unlock Pod. However, other roles, rights and combinations are possible and the example embodiment should not be taken to be limiting. Pod Owner 250, typically the one who performs the first setup as described in "Step of Setting up a Pod" will preferably have all possible rights, including the ability to create other owners, users and agents as well as assign rights to them. The example in FIG. 7 shows an additional role of Pod Owner Delegate which is a role with identical rights as Pod Owner 250 with the exception of the ability to delete other Pod Owners 250. An example of use of such a role is now presented. A Pod Owner 250 may purchase a Pod 200 and rent it to another Pod Owner 250a. Pod Owner 250a desires all rights to use it and create additional Pod Owner 250b, Pod Owner 250c and so on (as in the family example described above). However, at the end of a rental, Pod Owner 250 may want to reclaim Pod 200, and this may not be possible if Pod Owner 250a can delete Pod Owner 250. In some cases, Pod Owner 250 may give all rights that she has including deletion to Pod Owner 250a, and then delete oneself or Pod Owner 250a may delete Pod Owner 250, thus effectively transferring ownership of Pod 200. Pod User 260 is a role created by Pod Owner 250 and allows Pod User 260 to operate Pod 200 including allowing Pick-ups and Deliveries of her Package 101, which by definition preferably includes the ability to unlock Pod 200 to do so. In addition, to allow Pickups and Deliveries Pod User 260 can block a Usage Period 272 for said Pick up or Delivery. Finally, Pod User 260 has the ability to create other Pod Users 260a, 260b and so on and said Pod Users will have the same rights as Pod User 260. Pod Owner 250 can also create Pod Users 260c, Pod User 260d and so on which are independent of Pod Users 260a, 260b etc. created by Pod User 260. The role of Pick-up/Delivery Agent 300 in this context allows only a single right i.e. to lock or unlock Pod 200, but can obtain additional rights such as the ability to operate heating/cooling elements and the like, as explained elsewhere in the present disclosure. Finally, Recipient 103 can have Package 101 delivered or picked up to Pod 200 but cannot unlock Pod 200 to place Package 101 in it or retrieve a delivered Package 101 from Pod 200, but instead relies on a Pod Owner 250 or Pod User 260 to do so.

In an aspect, interactions between authorizer, requestor, various devices and Pod 200 have above been illustrated without reference to a server. In this case, information about Usage Role 270, Usage Rights 271, Usage Period 272 and associated information are stored in a device belonging to an authorizer (for example Pod Owner 250) and is synchronized with Pod 200 and therefore stored in Pod Data Storage 204. However, in some embodiments, at least a part of this information may be stored on a Server 400, either exclusively or in addition to being stored in Pod 200 and Pod Owner Device 251 and at least some of the communication for assignment of Usage Roles 270 or even the actual usage and operation for Pick-up and Delivery may be routed through said Server 400.

As taught above, these are example embodiments and can be configured differently depending on needs. For example, while locking and unlocking Pod 200 is described as a single right, it can be divided into two and a specific role may be granted one of those rights but not the second. Similarly, although creating, editing and deleting Pod User 260 is described as a single right, it may be implemented as a multiplicity of rights, one or more of which may be granted to a specific role. Furthermore, for the sake of simplicity, other potential rights have not been listed but have been described elsewhere in this description. As an example, the ability to operate certain features such as setting a heating or cooling operation to achieve a specific temperature may also be included in the list of rights that are granted or not granted to a particular role. By extension, the number of roles can also increase or decrease depending on the granularity of the rights that need to be granted or controlled. Thus, the different rights and roles envisioned in the present example embodiment should not be construed as a limitation but rather as examples of the present invention.

Payment on Delivery Embodiment

Cash-on-Delivery is a commonly used process, in which payment is made in cash when an item is delivered. In fact, payment may not be in cash, but some delivery companies equip their delivery personnel with card readers so that users can pay by swiping a card, but the process may still be called Cash-on-Delivery or COD. In recent years, electronic wallets have also become popular, the latter enabling a user device such as a Smartphone to access these wallet accounts for payments. Pod 200 can be enabled to accept delivery and enable payment to payee by Pod 200 or any user device that interfaces with Pod 200 such as Pod Owner Device 251, Pod User Device 261 and so on. A recipient of a Package 101 such as a Pod Owner 250 (references henceforth to Pod Owner 250 in the below description may be taken to apply to Pod User 260, Recipient 103 or any entity receiving a Package 101 in Pod 200 and Pod Owner 250 is simply taken as an example) may want to ensure that although she is not present, a payment is made only when delivery of said Package 101 is completed. At the same time, Pick-up/Delivery Agent 300 acting on behalf of a merchant wants to ensure that a payment is made when the parcel is delivered. If Package 101 is placed in Pod 200 and it is then locked, and if Pod Owner 250's payment process fails or an unethical Pod Owner 250 does not make a payment, a merchant or the Pick-up/Delivery Agent 300 can incur a loss. At the same time, Pick-up/Delivery Agent 300 may accept a payment or get confirmation of a payment but fail to place the Package 101 into Pod 200 (for example due to mechanical failure), or an unethical Pick-up/Delivery Agent 300 (or its controlling entity) may deliberately not place Package 101 into Pod 200. In the absence of a mechanism to guarantee payment as well as delivery when one or more of the parties involved are not present, serious issues could result. The present invention solves this problem as follows.

Pick-up/Delivery Agent 300 unlocks the Pod 200 and places Package 101 into an appropriate Sub-Pod 240 or Pod Receptacle 220 of Pod 200 (hereinafter individually and collectively referred to as Pod 200 for this embodiment), following which Pick-up/Delivery Agent 300 closes and locks Pod 200 or it is automatically closed and locked. Now, Pod 200 captures an image or video of Package 101 as delivered and transmits said image/video to Pod Owner 250. Pick-up/Delivery Agent 300 may also initiate capture and transmission of said image/video. Said image/video provides of proof of delivery and Pod Owner 250 therefore makes appropriate payment for Package 101 to Third Party Logistics Provider 104, Sender 102, a third party (such as a payment processor), or any other party authorized to receive payment (now together and severally called "Payee") for said Package 101. A receipt for payment may be sent to at least one of Pod Owner 250, a Server 400 and Payee. Either of these entities may send at least one of, the receipt, at least a portion of said receipt and a copy of said receipt to Pick-up/Delivery Agent 300. Server 400 may be owned operated or managed by Third Party Logistics Provider 104 or Sender 102 (such as a merchant or retailer). Said Server 400 sends a Message 110*b* to Pod 200 containing instructions to disable Usage Rights 271 of Pick-up/Delivery Agent 300 or disables Pod Passcode 213 and Pod 200 proceeds to do so. If Message 110*b* is not received within a certain time interval chosen by Pick-up/Delivery Agent 300 or its managing entity based on business practices of either entities, thus implying that payment has not been made, said Pick-up/Delivery Agent 300 may unlock Pod 200 again and retrieve Package 101 because Usage Rights 271 and/or Unlock Code 213 are still enabled.

Exchange of Goods Embodiment

In a parallel situation to Cash-on-Delivery a Pod Owner 250, Pod User 260 or any other recipient of a Package 101 may want to exchange a first Package 101 for a second Package 101*a*, latter being provided by a Sender 102 (references henceforth to Pod Owner 250 in the below description may be taken to apply to Pod User 260, Recipient 103 or any entity sending and/or receiving a Package 101 in Pod 200 and Pod Owner 250 is simply taken as an example). To enable such an exchange of Packages, two Pods 200, a single Pod 200 with two Receptacles 220, PodBank 23*o* with multiple Sub-Pods 240 or any other appropriate configuration may be used (Pod 200 is henceforth used as an example but the description below may be applied to any configuration). In such a case, it is important that receipt of first Package 101 is confirmed before second Package 101*a* is given. Pod Owner 250 places Package 101 into a Pod 200 for Pick up by Pick-up/Delivery Agent 300 (such as a Human or unmanned vehicle). Pick-up/Delivery Agent 300 places Package 101*a* which is to be exchanged for Package 101 into another Pod 200*a*. Pod 200*a* captures an image or video of Package 101*a* as delivered (preferably after Pod 200*a* is closed and locked and transmits said image/video to Pod Owner 250. Pick-up/Delivery Agent 300 may also initiate capture and transmission of said image/video. Said image/video provides of proof of delivery and Pod Owner 250 therefore unlocks Pod 200 or provides Pick-up/Delivery Agent 300 with unlock code.

Automated Deployment of Pick-Up/Delivery Agent

In the following Description, as an example Direct Sender 140 and Direct Recipient 150 are described, but this invention teaches that the description applies in the same manner to Pod Owner 250, Pod User 260 or any entity that deploys Pick-up/Delivery Agents 300 directly or indirectly for Pick up or Delivery.

In an example, a Server 400 may already have at least a portion of the information relevant to Pick up or Delivery of Sender 102 or Recipient 103, such as when either is an existing customer of the entity that owns or operates Server 400 (e.g. a retailer) or is a sender or recipient of a previous delivery (e.g. by a logistics company). Such information may also be saved in Direct Sender Device Data Storage 144 of Direct Sender Device 141 or correspondingly in Direct Recipient Device Data Storage 154 of Direct Recipient Device 151. If appropriate information is saved, such as at least a portion of Pick up Address 304, Pick up Information 305, Delivery Address 306, Delivery Information 307, or Package and Shipping Information 130, or any other appropriate and useful information, Direct Sender 140/Direct Recipient 150 will have the option of automatically retrieving relevant portions of saved information (e.g. the default address, default Pod UID 211 etc.) from, for example, Data Storage of associated device or from Server Data Storage 404, and sending this information to Pick-up/Delivery Agent 300 or to Server 400 which deploys or controls said Pick-up/Delivery Agents. In some cases, this information may be displayed to Sender 102 or Recipient 103 and confirmation requested or it may be sent automatically. In one example, Sender 102/Recipient 103 may send an update Message 110 and change the information even after it has been sent and Pick-up/Delivery Agent 300 automatically adjusts route, schedule etc. to reflect the updated information.

General

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of this document terms "coupled to" and "coupled with" are also used euphemistically to mean "communicatively coupled with" over a network, where two or more devices are able to exchange data with each other over the network, possibly via one or more intermediary device.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refers to at least one of something selected from the group or a list consisting of A, B, C . . . and N, the text should be interpreted as requiring only one element from the group, not A plus N, or B plus N, etc.

CONCLUSION

Although the present embodiments have been described with reference to specific example embodiments, various modifications and changes can be made to these embodiments without departing from the broader spirit and scope of the various embodiments. For example, the various devices, modules, etc. described herein can be enabled and operated using hardware circuitry, firmware, software or any combination of hardware, firmware, and software (e.g., embodied in a machine-readable medium).

In addition, it will be appreciated that the various operations, processes, and methods disclosed herein can be embodied in a machine-readable medium and/or a machine accessible medium compatible with a data processing system (e.g., a computer system), and can be performed in any order (e.g., including using means for achieving the various operations). Accordingly, the specification and drawings are to be regarded in an illustrative rather than a restrictive sense. In some embodiments, the machine-readable medium can be a non-transitory form of machine-readable medium.

What is claimed is:

1. A device to aid in delivering, storing, and picking up of goods, comprising:
a receptacle;
a computing system;

a camera;
a multiplicity of physical sensors, wherein the multiplicity of physical sensors measure a physical measurement and an environmental measurement, said measurements including:
a temperature measurement,
a weight measurement,
a humidity measurement,
one of any other environmental measure measurement, and
a motion measurement;
a multiplicity of chemical sensors, wherein the multiplicity of chemical sensors detect the presence of a specified chemical; and
wherein a set of inputs from the camera, multiplicity of physical sensors and the multiplicity of chemical sensors creates a record of a:
a picture,
a multiplicity of pictures,
a video,
a multiplicity of videos, and
a data embodying readings from at least a sensor;
and wherein the device is communicatively coupled to one or more other entities through at least one of a local network and an external network, and wherein the one or more other entities comprises at least a pod, wherein the pod comprises a pod computing system a pod networking system:
to perform at least one of the actions of:
transmitting a set of data to the one or more other entities,
receiving the set of data from the one or more other entities,
transmitting a set of commands to the one or more other entities, and
receiving a set of commands from the one or more other entities, and
wherein the one or more entities further comprises at least one of a server, an owner device, a user device, and a device coupled to a pickup/delivery agent,
wherein the device communicates at least a first message to the pod authenticating the device to the pod and the pod responds with at least a message to device authenticating the pod to the device, and wherein the messages causes the pod to unlock and further causes the device to deliver a package to the pod.

2. The device of claim 1 further comprising:
wherein the device:
acts on a command from a second device and not acting on a second command from the second device;
computes that the command is to be acted upon; and
computes the second command cannot be acted upon based on a set of instructions in a local data storage of the device.

3. The device of claim 1, wherein the computing system of the device comprises a set of instructions that override instructions received from an external entity.

4. The device of claim 1 further comprising:
wherein the device:
records set of inputs from the camera, multiplicity of physical sensors and the multiplicity of chemical sensors at pre-determined time intervals;
detects a change to any of the set of inputs as a function of time;
communicates the results of the set of inputs from the camera, multiplicity of physical sensors and the multiplicity of chemical sensors in an electronic message sent to the entities to which the device is communicatively coupled.

5. The device of claim 1, wherein the device when triggered by an event from the list of:
the device computes that a package has been delivered;
the device receives a message that the package has been delivered;
the device computes that the package has been retrieved
the device receives a message that the package has been retrieved;
the device computes that the package is to be delivered within an interval of time;
the device computes that the package is to be retrieved within an interval of time; and
the device computes that an interval of time has elapsed; and
wherein the device creates a unique record, and wherein the unique record is used as proof of an event from the list of:
retrieval of the package,
delivery of the package,
opening of the device,
closing of the device,
opening of the receptacle, and
closing of the receptacle.

6. The device of claim 1,
wherein the device recognizes that the device is occupied, by comparing a stored image, and an image acquired by the at least a camera,
wherein the device determines that the device is occupied when the stored image and the image acquired by the camera are not identical; and
wherein the device determines that the storage device is not occupied when the stored image and the image acquired by the camera are identical.

7. The device of claim 1,
wherein a portion of the image acquired by the camera comprises a label, a display and a graphic, and at least one of a label, a display and a graphic is used to determine that the package occupies the device.

8. The device of claim 7, wherein the label, the display and the graphic comprises a feature of the package and a feature of the physical storage device.

9. The device of claim 8,
wherein a portion of the image acquired by the camera comprises the label and a unique graphic, and wherein a portion the label or the unique graphic is used to determine that the package occupies the device.

10. The device of claim 1,
wherein the device comprises a first electronic lock,
wherein the receptacle comprises a second electronic lock so that the device and the receptacle are unlocked in a combination selected from a list of:
the first electronic lock and the second electronic lock are unlocked with a first electronic code,
the first electronic lock is unlocked with the first electronic code and the second electronic lock is unlocked with the second electronic code, and
the first electronic lock and the second electronic lock is unlocked with the first and second electronic code, but second electronic lock is unlocked only if the first electronic lock is also unlocked.

11. The device of claim 10, wherein the device is unlocked and opened in order to access the receptacle.

12. The device of claim 10, wherein the device does is not unlocked or opened in order to access the receptacle.

13. The device of claim 10, wherein the device is unlocked but is not opened to access the receptacle.

\* \* \* \* \*